United States Patent [19]

Uchida et al.

[11] Patent Number: 4,497,210

[45] Date of Patent: Feb. 5, 1985

[54] PHASED ARRAY ULTRASONIC TESTING APPARATUS AND TESTING METHOD THEREFOR

[75] Inventors: Kuniharu Uchida, Fujisawa; Satoshi Nagai, Yokohama; Ichiroh Komura, Yokohama; Taiji Hirasawa, Yokohama, all of Japan

[73] Assignee: Tokyo Shibaura Denki Kabushiki Kaisha, Kawasaki, Japan

[21] Appl. No.: 510,834

[22] Filed: Jul. 5, 1983

[30] Foreign Application Priority Data

Jul. 5, 1982 [JP] Japan .................................. 57-116435
Dec. 16, 1982 [JP] Japan .................................. 57-220443

[51] Int. Cl.$^3$ ............................................. G01N 29/04
[52] U.S. Cl. ........................................ 73/602; 73/619; 73/628
[58] Field of Search ............... 73/602, 609, 619, 626, 73/628; 128/660

[56] References Cited

U.S. PATENT DOCUMENTS 4,070,642 1/1978 Iinuma et al. .
4,241,610 12/1980 Anderson .
4,446,740 5/1984 Wilson et al. ........................ 73/626
4,458,533 7/1984 Borburgh .............................. 73/626

FOREIGN PATENT DOCUMENTS 57-13820 3/1982 Japan .

OTHER PUBLICATIONS

"Das Phased Array Als Neuer, Elektronisch Steuerbarer Ultraschallwandler In Der Werkstoffprufung" by W. Gebhardt, F. Bonitz, H. Woll.
Materials Evaluation vol. 40-1, "Characterization of Flow Location, Shape, and Dimensions with Alok System"; B. Grohs et al.; Jan. 1982.

*Primary Examiner*—Anthony V. Ciarlante
*Attorney, Agent, or Firm*—Oblon, Fisher, Spivak, McClelland & Maier

[57] ABSTRACT

A phased array ultrasonic testing apparatus includes: an array probe for ultrasonic transmission and reception; a transmitter for sequentially exciting transducers of the probe in a predetermined order; a circuit for preparing a composite signal from reception output from the probe; and a circuit for preparing an image signal indicating an internal flaw of a tested body in synchronism with the composite signal in accordance with a transmission beam index point and a steered angle of an ultrasonic main beam.

29 Claims, 50 Drawing Figures

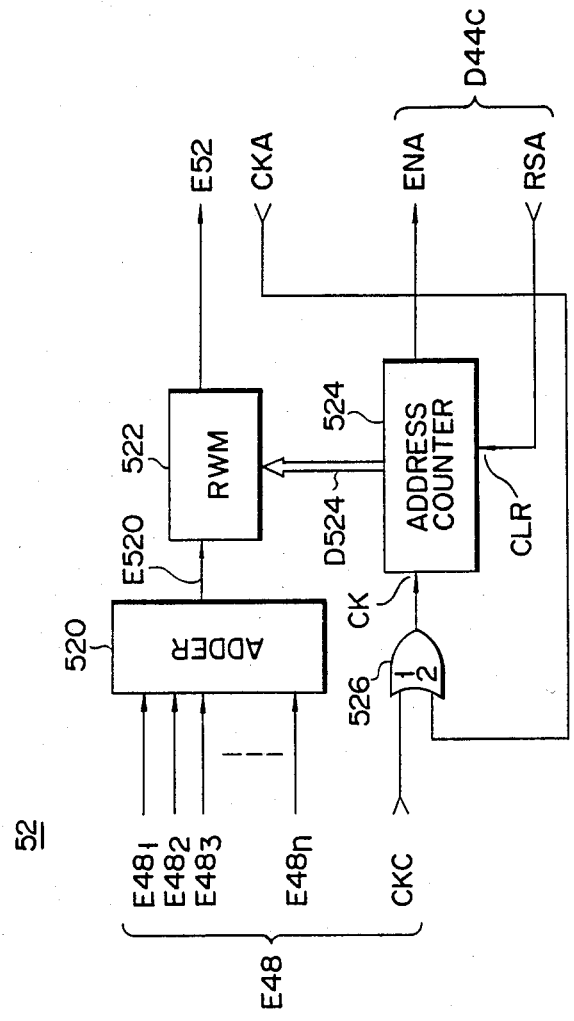
F I G. 15

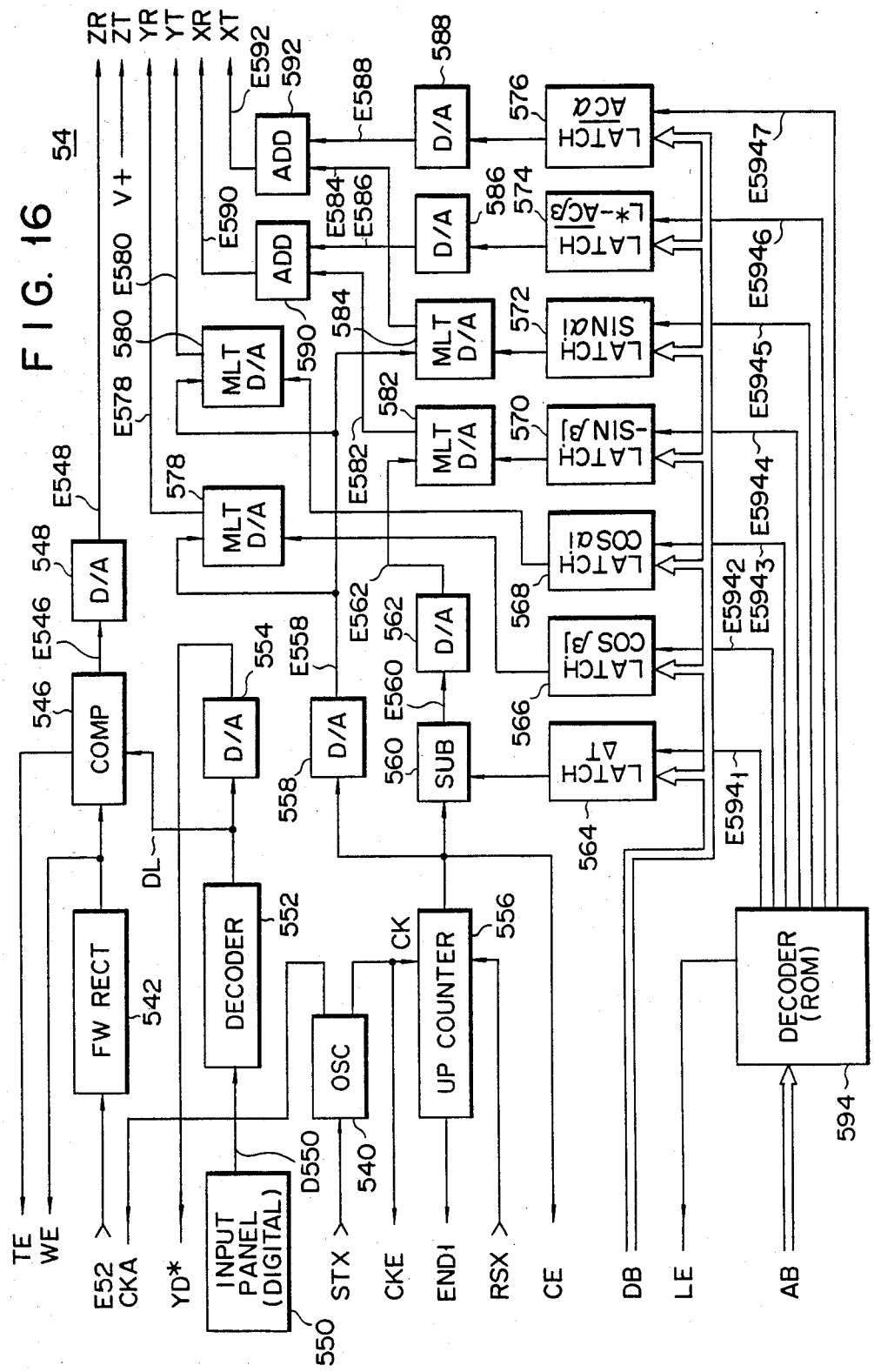
F I G. 16

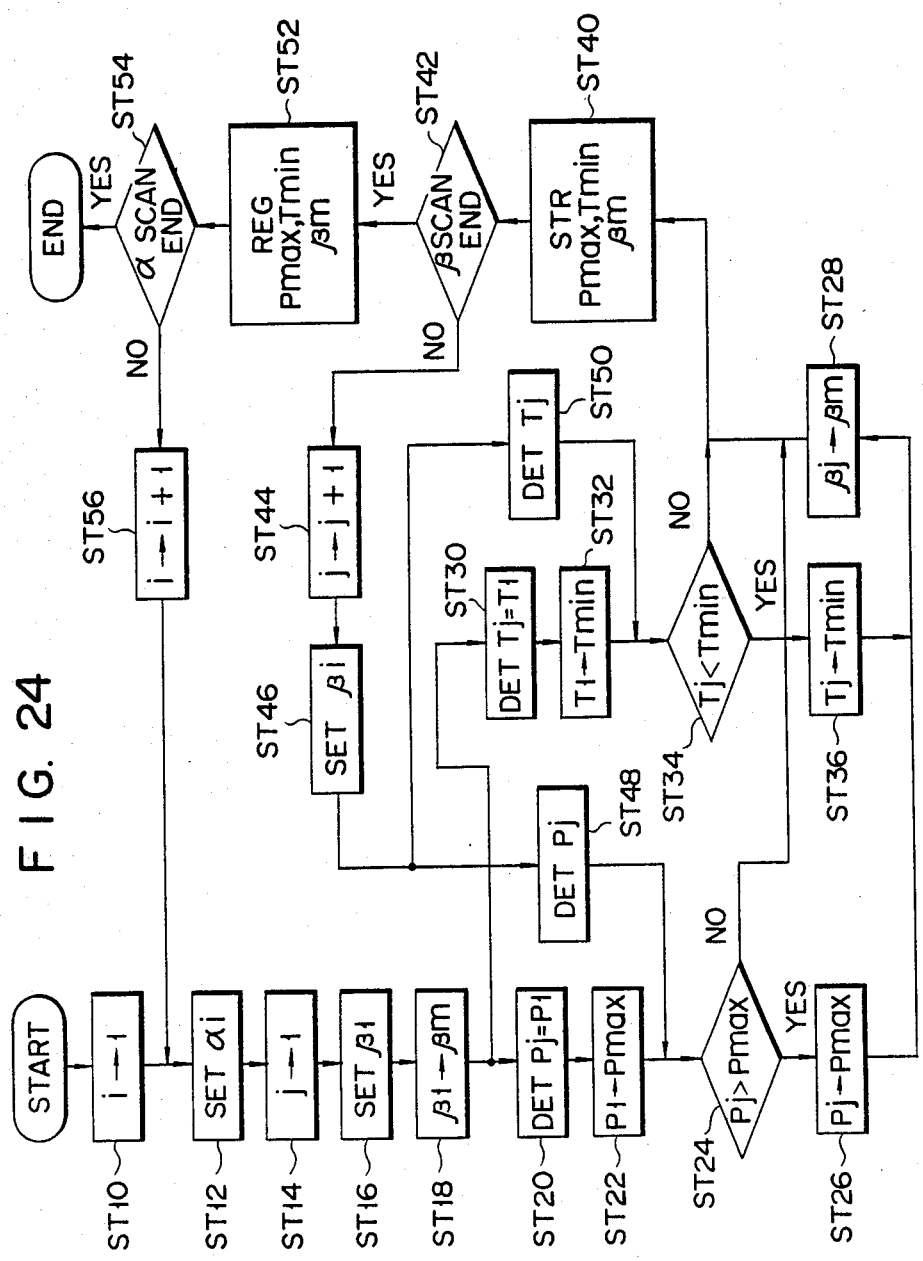
F I G. 24

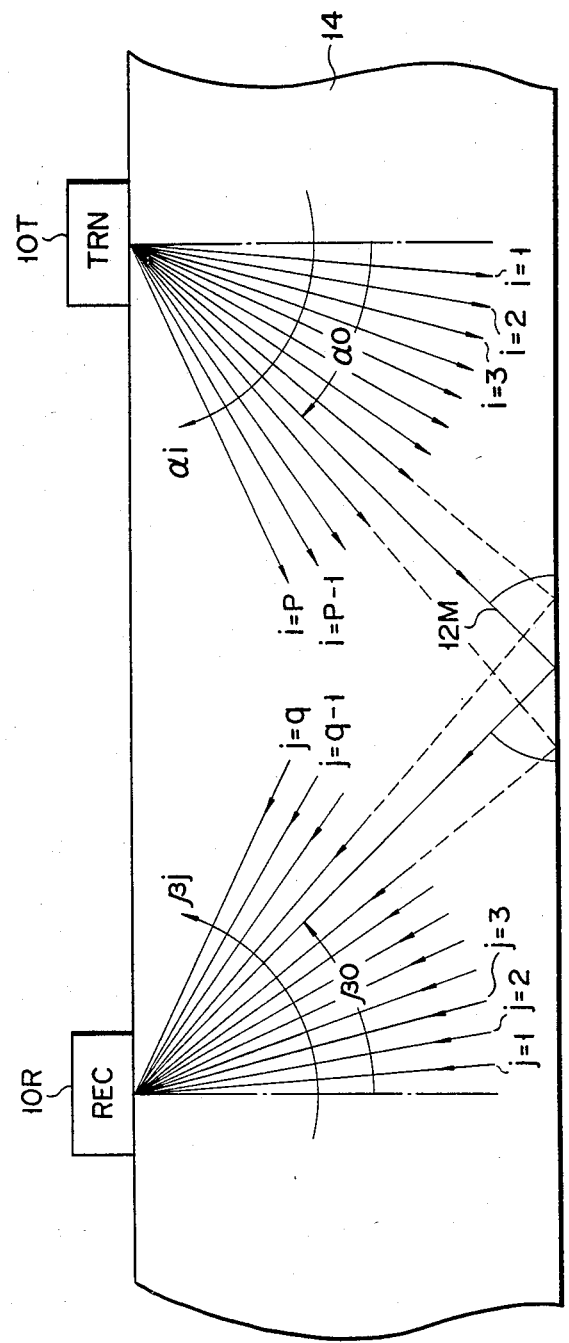

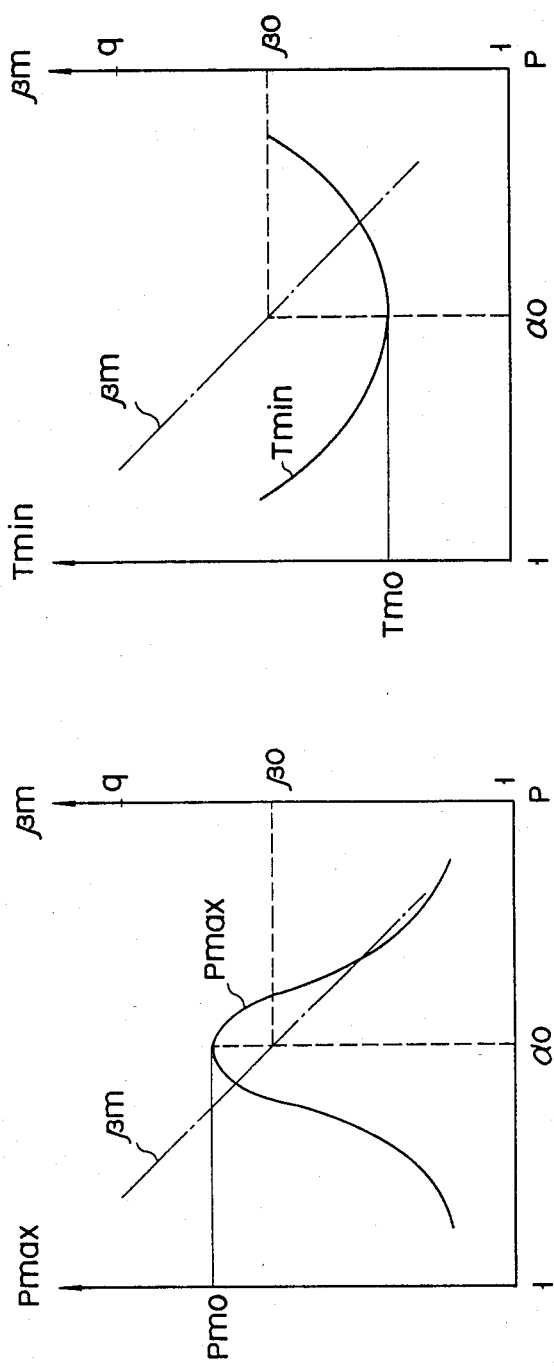

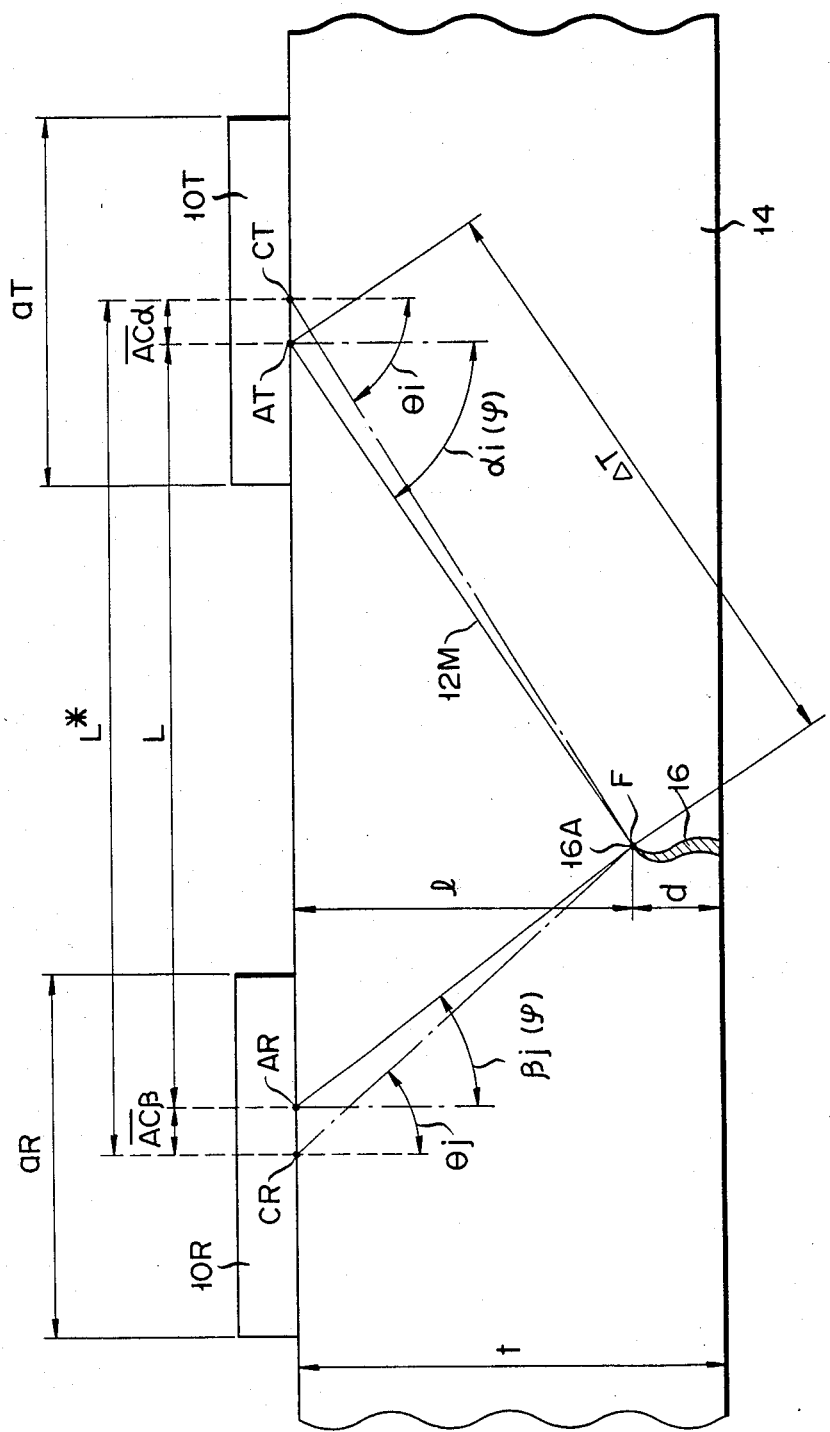
F I G. 37

4,497,210

PHASED ARRAY ULTRASONIC TESTING APPARATUS AND TESTING METHOD THEREFOR

BACKGROUND OF THE INVENTION

The present invention relates to a phased array ultrasonic testing apparatus and testing method therefor for testing for internal flaws in an object made of a metal or nonmetallic material using an ultrasonic wave.

Conventionally, an ultrasonic testing apparatus has been proposed to test for flaws within an object. The apparatus of this type has also been applied to an ultrasonic diagnostic apparatus for examining a patient. The ultrasonic testing apparatus has an array probe comprising a plurality of ultrasonic transmission/reception transducers, and an electronic circuit for controlling the ultrasonic transmission/reception timing of these transducers. The testing apparatus of this type generally employs an electronic scanning system. The electronic scanning system includes linear scanning and sector scanning. Linear scanning is performed such that some of the plurality of transducers of ultrasonic probe are sequentially activated or excited. As shown in FIG. 1, ultrasonic beams 12 then propagate linearly within tested body 14. Flaw portion 16 inside tested body 14 is B-scope displayed as flaw image 20 on CRT display screen 18 (FIG. 2). On the other hand, according to sector scanning, ultrasonic transmission/reception timing of the transducers of ultrasonic probe 10 change sequentially. As shown in FIG. 3, ultrasonic beams 12 are scanned in a sector shape inside tested body 14. This beam scanning allows B-scope display of flaw portion 16 inside tested body 14 as flaw image 20 on CRT display screen 18 (FIG. 4).

In an ultrasonic testing, a tip echo technique is proposed as a technique for evaluating dimensions of a flaw on a surface of and/or inside of tested body 14. According to this technique, a conventional type ultrasonic probe 22 is used in place of an array probe. Now assume that ultrasonic beam 12 from probe 22 is scattered or diffracted at one tip 16A of flaw portion 16, as shown in FIG. 5. In this case, when a wave received by probe 22 is A-scope displayed on CRT display screen 18, diffraction echo component 26A appears in displayed waveform 24 (FIG. 6). Then assume that probe 22 is shifted to the right by predetermined distance X in FIG. 5. Diffraction echo component 26B caused by the other tip 16B of flaw portion 16 is A-scope displayed on CRT display screen 18 (FIG. 6). According to the tip echo technique, a predetermined operation is performed to evaluate the dimensions of flaw portion 16, using shift distance X of probe 22 in FIG. 5 and propagation path lengths of ultrasonic beams corresponding to echo components 26A and 26B.

An ALOK system is proposed as another technique for evaluation of the above flaw dimensions. In this system, a correlation between a shift distance of the probe and propagation path lengths of flaw echoes is computed as precisely as possible. The flow dimensions are evaluated from an obtained correlation. The following reference is available for the ALOK system: B. Grohs et al., "Characterization of Flaw Location, Shape and Dimensions with ALOK system", *Material Evaluation*, vol. 40-1 (Jan. 1982).

Two types of sector scanning methods are available: one wherein a test is made while ultrasonic beams are converged; the other wherein a test is made without converging ultrasonic beams. FIG. 7 shows a case of converged beam sector scanning. Referring to FIG. 7, main beam direction 30 of beams 12 converged by electronic control at single point F geographically differs from main beam direction 32 of beams collimated thereby. Even if a test is made under the condition that a transmission/reception beam index point of the ultrasonic beams is preset at array center C of probe 10, an actual transmission/reception beam index point becomes point A. As a result, a position of the B-scope display image indicating an internal flaw of tested body 14 is misaligned from the actual position. Referring to FIG. 8, flaw portions $16_1$ and $16_2$ exist at angular positions $\theta 1$ and $\theta 2$ with respect to the normal line through the array center or preset main beam transmission/reception beam index point C. Angular positions $\theta 1°$ and $\theta 2°$ of flaw images $20_1$ and $20_2$ displayed on B-scope CRT display screen 18 differ from the actual angular positions $\theta 1$ and $\theta 2$ due to this misalignment, as shown in FIG. 9. For this reason, according to the converged beam testing technique having array center C as the beam transmission/reception beam index point, internal flaw portions 16 in tested body 14 cannot be measured with high precision.

Furthermore, according to the tip echo technique described above, the position of the flaw portion inside the tested body cannot be detected. For this reason, when the tip echo technique is employed, the position of the internal flaw portion must be checked by a cut-and-try procedure. This cut-and-try procedure must be performed while probe 22 is precisely moved to ensure the ultrasonic beam is properly incident on flaw tips 16A and 16B (FIG. 5). Therefore, complicated probe scanning jigs must be used. However, even if a precise cut-and-try procedure is performed using such jigs, a large diffraction echo may not be obtained at a given angle of incidence of an ultrasonic beam on flaw tip 16A or 16B. There is no guarantee of alignment of the diffraction echo propagation direction with a high reception sensitivity direction of probe 22. In order to eliminate the above drawbacks, a plurality of ultrasonic probes having different transmission/reception angles must be prepared. The cut-and-try procedure must be performed in accordance with various combinations of these probes. Otherwise, a highly precise diffraction echo cannot be obtained and flaw dimensions cannot be evaluated.

SUMMARY OF THE INVENTION

It is a first object of the present invention to provide a phased array ultrasonic testing apparatus for testing a position and/or dimensions of a surface or internal flaw of a tested body with high precision.

It is a second object of the present invention to provide a phased array ultrasonic testing method for obtaining the flaw position and/or dimensions with high precision.

In order to achieve the first object, there is provided a phased array ultrasonic testing apparatus comprising:

array probe means having a plurality of ultrasonic transducers for transmitting/receiving an ultrasonic wave;

transmitting means coupled to the probe means for driving the transducers to transmit an ultrasonic main beam in a predetermined direction within a tested body;

synthesizing means coupled to the probe means for synthesizing reception echo signals corresponding to ultrasonic echoes received by the transducers and generating a composite reception signal; and signal processing means coupled to the synthesizing means for generating an image signal synchronous with the composite reception signal in accordance with a beam index point of the ultrasonic main beam and a steered angle thereof.

In order to achieve the second object, there is provided a method for phased array ultrasonic testing in which timings of ultrasonic transmission and reception are electronically controlled by an array probe having a plurality of ultrasonic transducers, comprising the steps of:

(a) determining an actual steered angle of an ultrasonic main beam in accordance with a predetermined convergence path length of the ultrasonic main beam, a predetermined steered angle of the ultrasonic main beam, and a predetermined aperture size of the probe at the time of ultrasonic transmission, the predetermined steered angle being defined with respect to a normal line at a central point of an array of the transducers, and the actual steered angle being defined with respect to a normal line at an actual beam index point of the ultrasonic main beam;

(b) determining a distance between the central point of the array and the actual beam index point in accordance with the actual steered angle, the predetermined convergence path length, and the predetermined aperture size; and (c) determining an image sweep start point and a sweep direction for displaying an ultrasonic echo received by the probe in accordance with the actual steered angle obtained in the step (a) and the distance obtained in the step (b).

BRIEF DESCRIPTION OF THE DRAWINGS

FIG. 15 is a block diagram showing a detailed configuration of add memory 52 shown in FIG. 10;

FIGS. 16 to 19 are block diagrams together showing a detailed configuration of signal processor 54 shown in FIG. 10;

FIG. 24 is a flow chart for explaining the steps of evaluating a flaw dimension;

FIG. 25 shows propagation directions of ultrasonic main beams 12M when tested body 14 having no flaw is tested in accordance with the flow chart in FIG. 24;

FIG. 26 is a graph showing a relationship among data Pmax, $\beta$m, and $\alpha$i obtained when tested body 14 (FIG. 25) is tested in accordance with the flow chart in FIG. 24;

FIG. 27 is a graph showing a relationship among data Tmin, $\beta$m and $\alpha$i obtained when tested body 14 (FIG. 25) is tested in accordance with the flow chart in FIG. 24;

FIG. 37 shows a state wherein ultrasonic main beam 12M transmitted from transmission probe 10T is diffracted or scattered at flaw tip 16A and a diffraction beam is incident on reception probe 10R;

DETAILED DESCRIPTION OF THE PREFERRED EMBODIMENT

Figure 2:
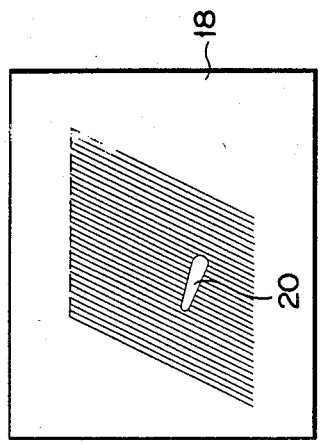
FIG. 2 shows a B-scope display obtained by the scanning technique shown in FIG. 1.
Figure 4:
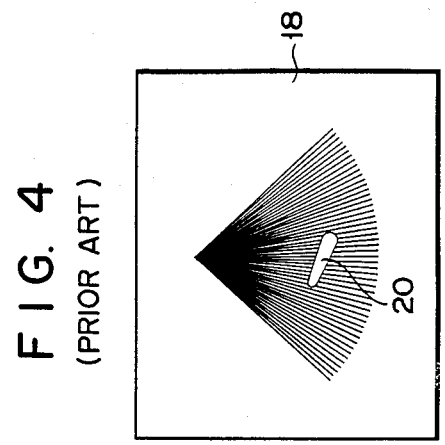
FIG. 4 shows a B-scope display obtained by the scanning technique shown in FIG. 3.
Figure 1:
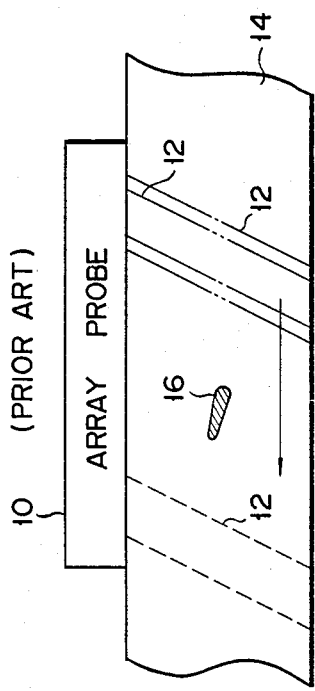
FIG. 1 shows a conventional example of linear scanning with an ultrasonic beam.
Figure 3:
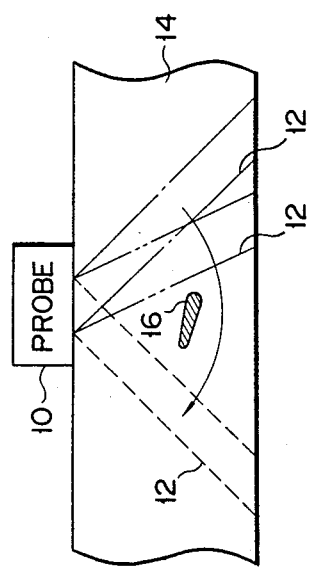
FIG. 3 shows a conventional example of sector scanning with an ultrasonic beam.
Figure 5:
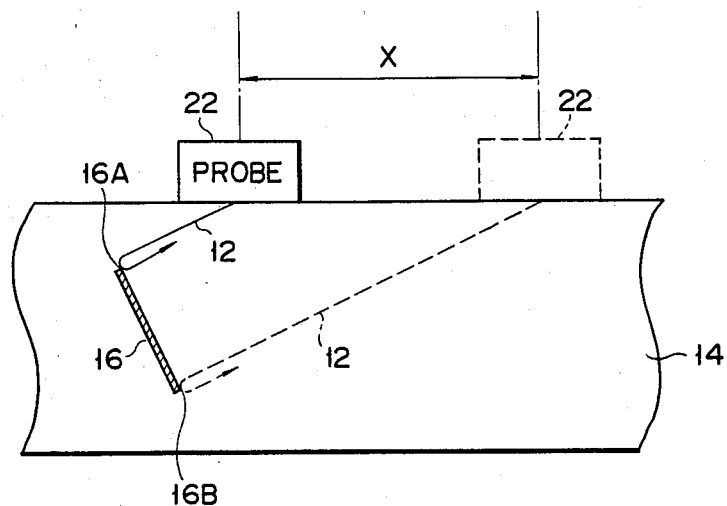
FIG. 5 shows a conventional example for evaluating dimensions of a flaw inside a tested body in accordance with a tip echo technique.
Figure 6:
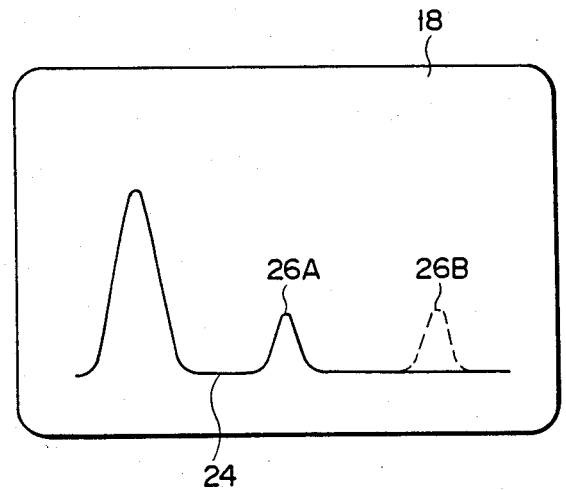
FIG. 6 shows an A-scope display obtained by the tip echo technique shown in FIG. 5.
Figure 7:
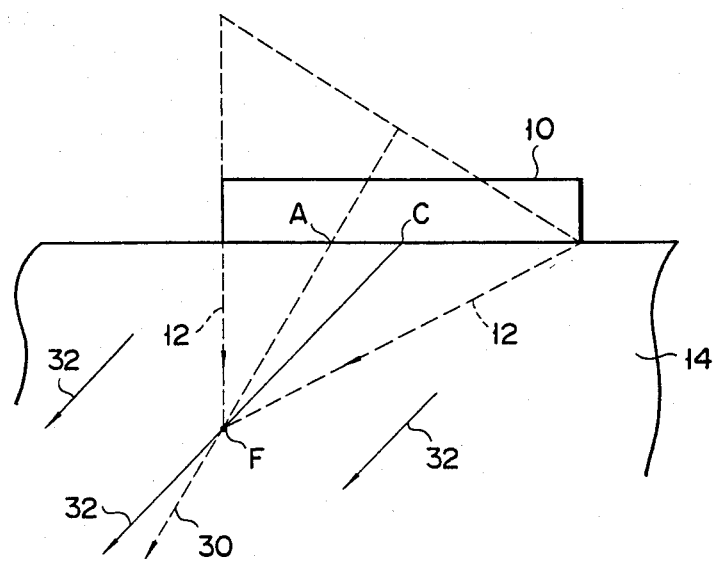
FIG. 7 shows a state wherein transmission/reception beam index point A of the ultrasonic main beam is misaligned from center C of an array probe when converged beam sector scanning is performed.

A preferred embodiment of the present invention will now be described with reference to the accompanying drawings. The same reference numerals denote the same parts throughout the drawings so as to avoid repeated explanation of the same parts.

Figure 10:
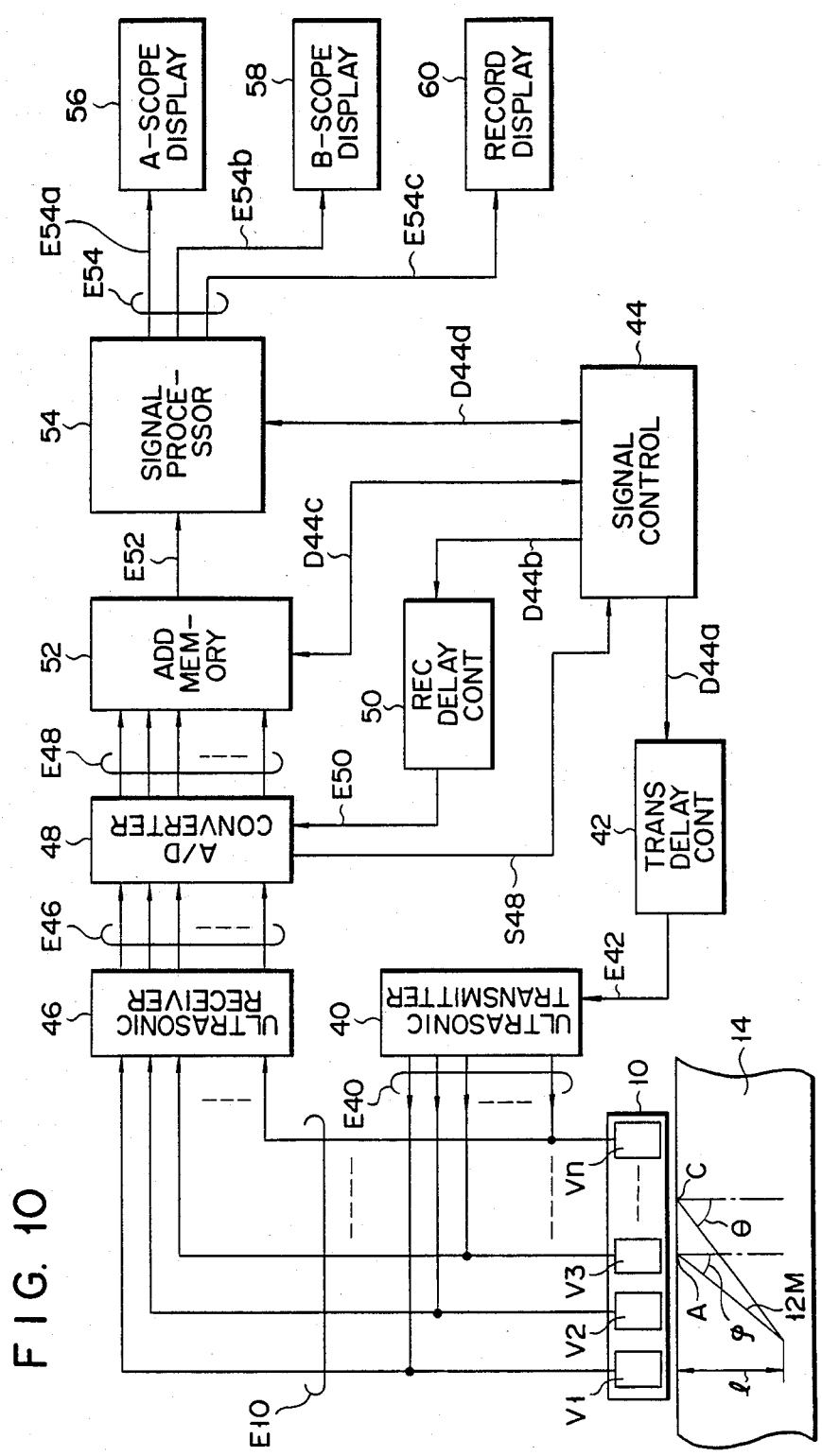
FIG. 10 is a block diagram showing a configuration of a phased array ultrasonic testing apparatus according to the present invention.

FIG. 10 shows a phased array ultrasonic testing apparatus according to an embodiment of the present invention. Probe 10 for testing tested body 14 has n arrayed ultrasonic transducers V1 to Vn. Probe 10 may comprise a conventional probe using a piezoelectric element or the like. Transducers V1 to Vn (some or all) are energized or driven by transmission pulses E40 from ultrasonic transmitter 40 having n transmission amplifiers. Ultrasonic main beam 12M is emitted from probe 10 in a predetermined angular direction $\phi$. The order of energization of transducers V1 to Vn is determined by trigger signals E42 supplied from transmission delay controller 42 to transmitter 40. Transmitter 40 may comprise a conventional transmitter. The detailed configuration of controller 42 will be described later.

Transducers V1 to Vn convert electric signals to mechanical movement and vice versa. Transducers V1 to Vn generate reception echo signals E10. Each of signals E10 has a magnitude corresponding to an intensity of a received ultrasonic echo. Signals E10 are received by ultrasonic receiver 46 having n reception amplifiers. Receiver 46 amplifies signals E10 and generates reception signals E46 respectively corresponding to signals E10. Receiver 46 may comprise a conventional receiver. Signals E46 are analog signals, and these analog reception signals E46 are converted by high-speed A/D converter 48 to digital reception signals E48 in response to trigger signals E50 from reception delay controller 50, respectively. In other words, analog waveforms of signals E46 are synchronous with trigger or timing signals E50 and are converted to digital data, respectively. The operation of A/D converter 48 is controlled in response to timing signals D44b supplied from signal controller 44 through reception delay controller 50. The end of A/D conversion is signalled by signal S48 supplied from A/D converter 48 to signal controller 44.

Signal controller 44 supplies timing signals D44a to transmission delay controller 42 to determine a set of transducers to be used for ultrasonic transmission. Signal controller 44 supplies timing signals D44b to reception delay controller 50 to determine a set of transducers to be used for ultrasonic reception. Signals D44a and D44b determine steered angle $\phi$ of ultrasonic main beam 12M and convergence path length l of the ultrasonic beams. Signal controller 44, A/D converter 48 and delay controller 50 will be described in detail later.

Digital reception signals E48 are added and linked by add memory 52 and are temporarily stored in memory 52. Memory 52 stores digital signals under the control of signal controller 44. In this case, signal controller 44 controls to match the starting points of A/D conversion of signals E46 by A/D converter 48. The storage operation of memory 52 is controlled in response to signals D44c from signal controller 44. The digital data stored in memory 52 is read out as composite reception signal E52 in accordance with an instruction from signal controller 44. The detailed configuration of memory 52 will be described later.

Composite reception signal E52 is supplied to signal processor 54. Processor 54 generates an intensity modulation signal corresponding to a level of signal E52 which exceeds a predetermined level. Processor 54 calculates steered angle $\phi$ and transmission/reception beam index point A of ultrasonic main beam 12M at the time of reception. Processor 54 then determines image sweep start point and a sweep direction on a B-scope CRT. Thereafter, processor 54 supplies to B-scope display 58 a B-scope display signal E54b including the intensity modulation signal. Steered angle $\phi$ and transmission/reception beam index point A are computed using ultrasonic wave convergence path length l, steered angle $\theta$ of ultrasonic waves with respect to array center C of the transducers, and aperture size a of the ultrasonic transducers in accordance with equations (1) and (2) described later on. These three data are collectively known as signal D44d which is supplied from signal controller 44 to processor 54.

In processor 54, a gate is preset in a predetermined range along the time base of signal E52. Processor 54 then detects maximum value Pmax of a received echo waveform amplitude exceeding a predetermined level within the predetermined gate, and also detects minimum beam propagation path length Tmin of the main beam. These numerical data Pmax and Tmin and waveform data of composite reception signal E52 are supplied as signal E54a to A-scope display 56.

Processor 54 further detects reception (transmission) main beam steered angles $\beta m$ (or $\alpha m$) for every transmission (reception) main beam steered angle $\alpha i$ or (or $\beta j$), which depend on the received echo waveform maximum value Pmax and minimum beam propagation path length Tmin. Subsequently, processor 54 detects steered angles $\alpha_T$ (or $\beta_T$) when echo waveform maximum value Pmax and minimum beam propagation path length Tmin become maximal Pm0 and minimal Tm0 for every steered angle $\alpha i$ (or $\beta j$), respectively. Thereafter, using known data (i.e., thickness t of tested body 14 and distance L between the transmission and reception beam index points) and any two of detected data $\alpha_T$, $\beta_T$ and Tm0, processor 54 evaluates flaw dimension d inside tested body 14 in accordance with equation (7), (8) or (9) to be described later. Data Pmax, Tmin, $\beta m$ ($\alpha m$), $\alpha i$ ($\beta j$), Pm0, Tm0, $\alpha_T$($\beta_T$) and d are supplied as record signal E54c to record display 60. Record display 60 records data corresponding to signal E54c and causes a CRT or X-Y plotter to display or plot information.

Figure 11:
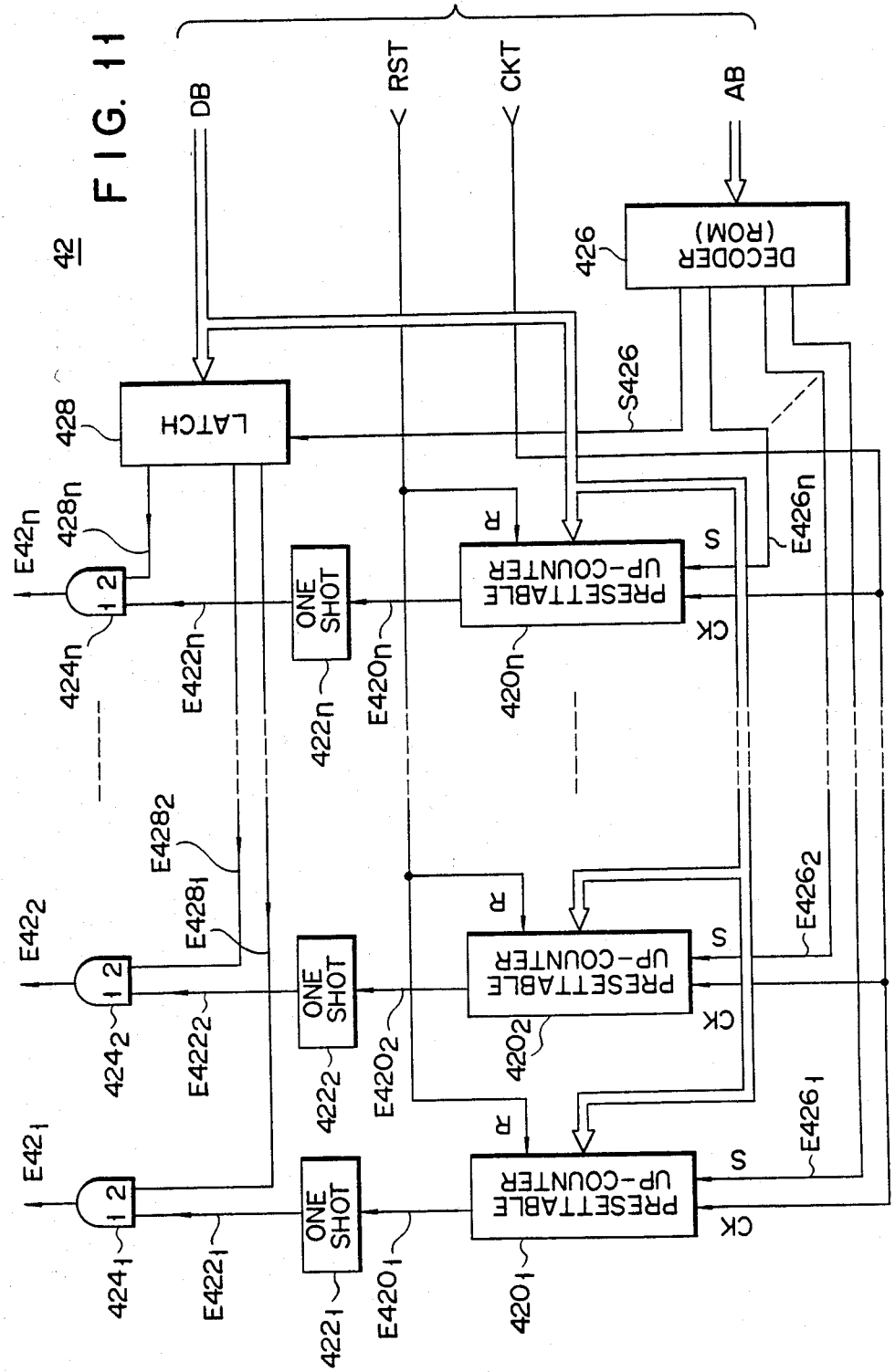
FIG. 11 is a block diagram showing a detailed configuration of transmission delay controller 42 shown in FIG. 10.

FIG. 11 shows the detailed configuration of transmission delay controller 42 show in FIG. 10. Controller 42 has presettable up-counters 420 ($420_1$ to $420_n$) which are equal in number to the n transducers Vn of probe 10. Preset data of counters $420_1$ to $420_n$ are supplied from signal controller 44 (FIG. 10) through data bus DB. Set pulses $E426_1$ to $E426_n$ supplied from decoder 426 to counters $420_1$ to $420_n$ determine which preset data on data bus DB are preset in counters $420_1$ to $420_n$. Decoder 426 comprises a ROM or the like. A readout address of ROM 426 is specified by address data supplied from controller 44 to ROM 426 through address bus AB. Assume that data on address bus AB accesses the first address of ROM 426, and that data on data bus DB indicates 10 (decimal notation). When the first address of ROM 426 is accessed, ROM 426 reads out parallel data $E426_1$ to $E426_n$ (=1000 . . . 0). Only the first bit of this parallel data is set at "1" (high level), and all the remaining bits are set at "0" (low level). In other words, only pulse $E426_1$ is generated, whereas pulses $E426_2$ to $E426_n$ are not generated. Therefore, preset data 10 (decimal notation) on data bus DB is preset by pulse $E426_1$ in counter $420_1$. Similarly, assume that data on address bus AB accesses the nth address of ROM 426, and that data on data bus DB indicates 100 (decimal notation). In this case, data 100 (decimal notation) is preset by pulse $E426_n$ in counter $420_n$.

Clock pulses CKT are supplied from controller 44 to counters $420_1$ to $420_n$. When counter $420_1$ counts 10 pulses CKT, it generates count-up pulse $E420_1$. Similarly, when counter $420_n$ counts 100 pulses CKT, it generates count-up pulse $E420_n$. One-shots $422_1$ to $422_n$ are triggered by pulses $E420_1$ to $E420_n$ from counters $420_1$ to $420_n$, respectively. When one-shots $422_1$ to $422_n$ are triggered by pulses $E420_1$ to $E420_n$, they generate transmission pulses $E422_1$ to $E422_n$, respectively. Each of transmission pulses $E422_1$ to $E422_n$ has a predetermined pulse width. Pulses $E422_1$ to $E422_n$ are supplied to first input terminals of AND gates $424_1$ to $424_n$, respectively. Gate signals $E428_1$ to $E428_n$ are supplied from latch 428 to second input terminals of AND gates $424_1$ to $424_n$. AND output signals $E42_1$ to $E42_n$ from AND gates $424_1$ to $424_n$ serve as trigger signals E42, respectively. Signals $E428_1$ to $E428_n$ correspond to the data on the data bus DB when latch pulse S426 is supplied to latch 428. Latch pulse S426 is generated when the address data on address bus AB specifies the (n+1) th address of ROM 426. In this case, the data on the data bus DB is stored in latch 428.

Data stored in latch 428 determines which one of AND gates $424_1$ to $424_n$ is to be turned on or opened. In other words, the content of latch 428 determines which trigger signals $E42_1$ to $E42_n$ are used (i.e., the content of latch 428 determines which transducers V1 to Vn of probe 10 are used for transmission). Count-up pulses $E420_i$ (i=1, 2, . . . , n) are sequentially generated from counters $420_i$ which sequentially count up the clock pulses. Therefore, the excitation order and timing of transducers V1 to Vn are determined in accordance with preset data of counters $420_1$ to $420_n$. When all counters $420_1$ to $420_n$ complete the count-up operation, these counters are reset by reset pulse RST from controller 44. One ultrasonic transmission by a selected set of transducers among transducers V1 to Vn is completed.

Figure 12:
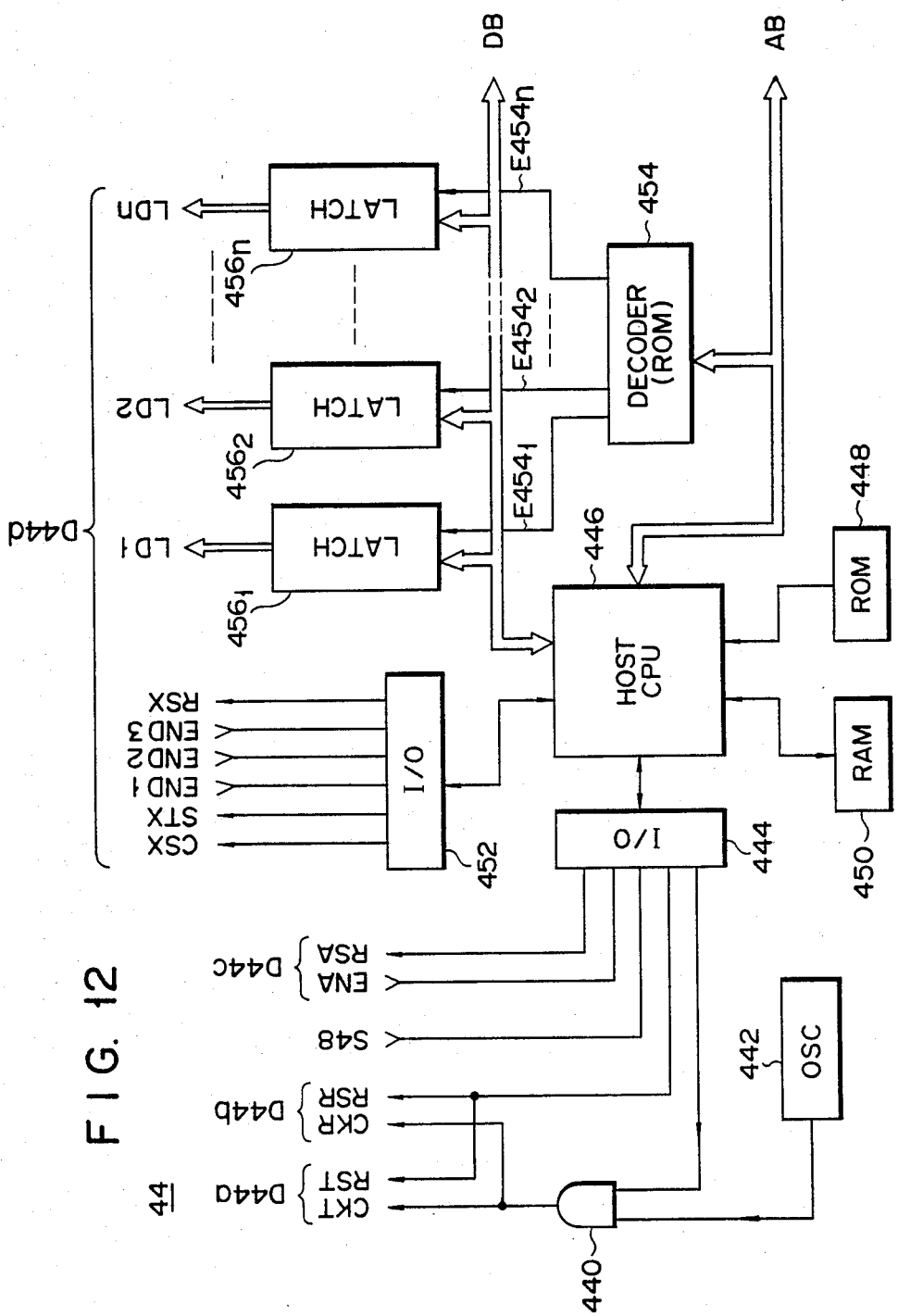
FIG. 12 is a block diagram showing a detailed configuration of signal controller 44 shown in FIG. 10.

FIG. 12 shows a detailed configuration of signal controller 44 shown in FIG. 10. Clock pulses CKT oscillated from oscillator 442 are supplied to counters $420_1$ to $420_n$ (FIG. 11) through AND gate 440. These clock pulses CKT are also used as clock pulses CKR in FIG. 13. AND gate 440 is controlled by host computer 446 through I/O device 444. Host computer 446 may comprise a microcomputer such as a #8048 (Intel Co.) or Z-80 (Zailog Inc.) Reset pulse RST for resetting counters $420_1$ to $420_n$ is generated from I/O 444 in accordance with a command from host computer 446. This reset pulse RST is also used as reset pulse RSR in FIG. 13. Preset data of counters $420_1$ to $420_n$ and latch data of latch 428 in FIG. 11 are generated from host computer 446 through data bus DB. Address data of decoder (ROM) 426 in FIG. 11 is generated from host computer 446 through address bus AB. A microprogram and the like for host computer 446 are stored in ROM 448, whereas a control program and predetermined data which are determined in accordance with the type of probe 10 and tested body 14 are stored in RAM 450. The operation of host computer 446 will be described in detail later with reference to flow charts.

Host computer 446 accesses readout addresses of decoder (ROM) 454 through address bus AB. ROM 454 supplies latch pulses $E454_1$ to $E454_n$ to latches $456_1$ to $456_n$. In latch pulses $E454_1$ to $E454_n$, any one of the pulses is set at logic level "1" (high level), while all the remaining pulses are set at logic level "0" (low level). The high level signal can be determined by the readout address signal on address bus AB. Data to be latched in latches $456_1$ to $456_n$ are supplied from host computer 446 to latches $456_1$ to $456_n$ through data bus DB. When pulse $E454_1$ is set at level "1" in response to the corresponding address data on address bus AB, latch $456_1$ latches data on data bus DB. Similarly, when pulse $E454_n$ is set at level "1" in response to the corresponding address data on address bus AB, latch $456_n$ latches data on data bus DB. Latches $456_1$ to $456_n$ generate latched data LD1 to LDn, respectively. Host computer 446 supplies pulses CSX, STX, RSX and fetches pulses END1 to END3 through I/O device 452. Pulses CSX, STX, RSX, END1 to END3 and data LD1 to LDn are used as signal D44d so as to couple signal controller 44 and signal processor 54 in FIG. 10.

Note that the number of latches $456_1$ to $456_n$ is the same as that of transducers V1 to Vn of probe 10 in FIG. 10. Latched data DL1 to DLn include data used for ultrasonic transmission.

Figure 13:
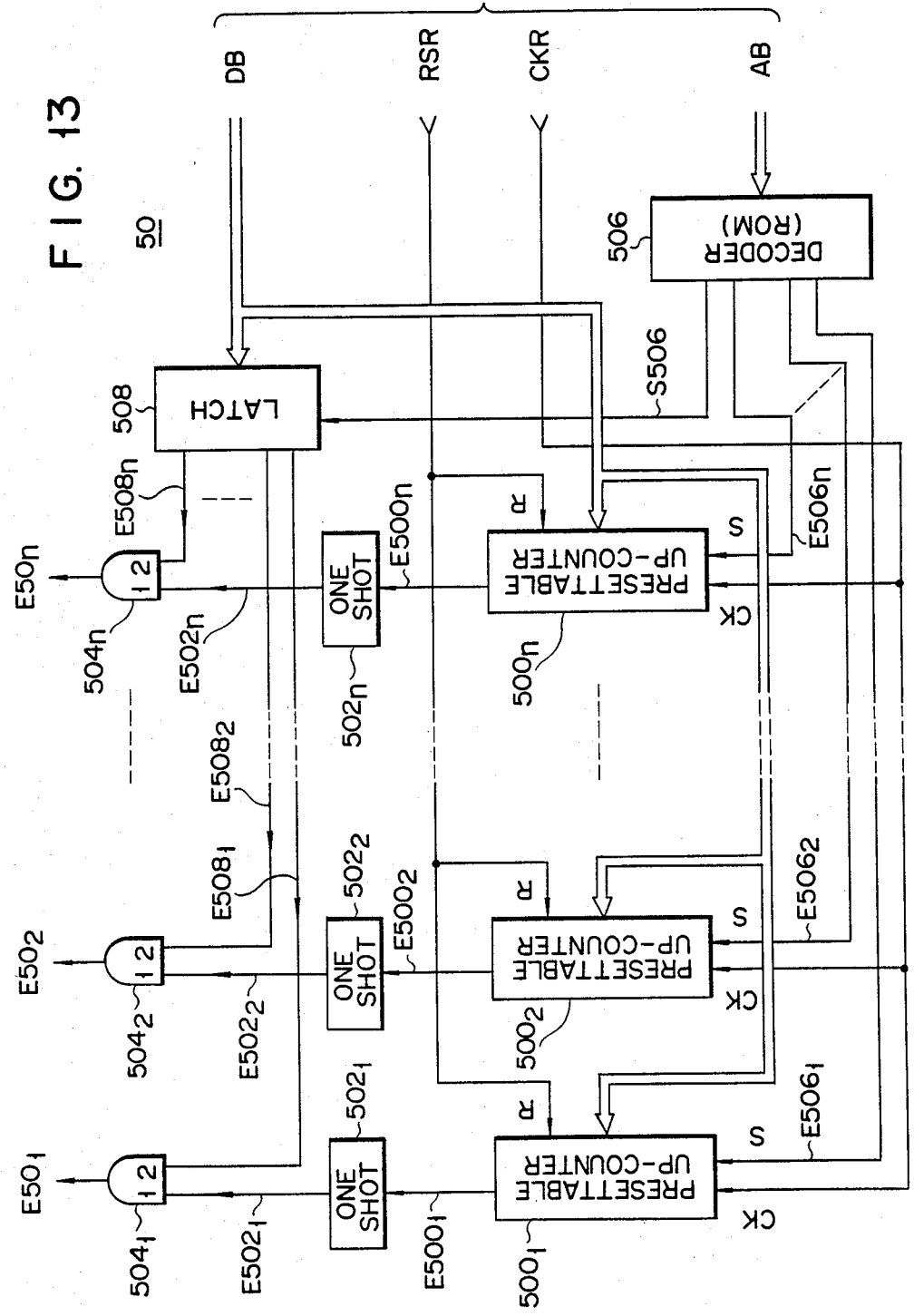
FIG. 13 is a block diagram showing a detailed configuration of reception delay controller 50 shown in FIG. 10.

FIG. 13 shows a detailed configuration of reception delay controller 50 shown in FIG. 10. Controller 50 has presettable up-counters 500 ($500_1$ to $500_n$) which are equal in number to those of controller 42. Preset data of counters $500_1$ to $500_n$ are supplied from signal controller 44 through data bus DB. Set pulses $E506_1$ to $E506_n$ supplied from decoder 506 to counters $500_1$ to $500_n$ determine which one of counters $500_1$ to $500_n$ receive preset data on data bus DB. Decoder 506 comprises a ROM or the like. A readout address of ROM 506 is specified by address data supplied from controller 44 to ROM 506 through address bus AB. Assume that data on address bus AB accesses the first address of ROM 506, and that data on data bus DB indicates 10 (decimal notation). When the first address of ROM 506 is accessed, ROM 506 reads out parallel data $E506_1$ to $E506_n$ ($= 1000 \ldots 0$). Only the first bit of this parallel data is set at "1" (high level), and all remaining bits are set at "0" (low level). In other words, only pulse $E506_1$ is generated, whereas pulses $E506_2$ to $E506_n$ are not generated. Therefore, preset data 10 (decimal notation) on data bus DB is preset by pulse $E506_1$ in counter $500_1$. Similarly, assume that data on address bus AB accesses the nth address of ROM 506, and that data on data bus DB indicates 100 (decimal notation). In this case, data 100 (decimal notation) is preset by pulse $E506_n$ in counter $500_n$.

Clock pulses CKR are supplied from controller 44 to counters $500_1$ to $500_n$. When counter $500_1$ counts 10 pulses CKR, it generates count-up pulse $E500_1$. Similarly, when counter $500_n$ counts 100 pulses CKR, it generates count-up pulse $E500_n$. One-shots $502_1$ to $502_n$ are triggered by pulses $E500_1$ to $E500_n$ from counters $500_1$ to $500_n$, respectively. When one-shots $502_1$ to $502_n$ are triggered by pulses $E500_1$ to $E500_n$, they generate A/D conversion timing pulses $E502_1$ to $E502_n$, respectively. Each of A/D conversion timing pulses $E502_1$ to $E502_n$ has a predetermined pulse width. Pulses $E502_1$ to $E502_n$ are supplied to first input terminals of AND gates $504_1$ to $504_n$, respectively. Gate signals $E508_1$ to $E508_n$ are supplied from latch 508 to second input terminals of AND gates $504_1$ to $504_n$. AND gate output signals $E50_1$ to $E50_n$ from AND gates $504_1$ to $504_n$ serve as trigger signals E50, respectively. Signals $E508_1$ to $E508_n$ correspond to the data on the data bus DB when latch pulse S506 is supplied to latch 508. Latch pulses 506 is generated when the address data on address bus AB specifies the (n+1)th address of ROM 506. In this case, the data on the data bus DB is stored in latch 508.

Data stored in latch 508 determines which one of AND gates $504_1$ to $504_n$ is to be turned on or opened. In other words, the content of latch 508 determines which trigger signals $E50_1$ to $E50_n$ are used (i.e., the content of latch 508 determines which waveforms of output signals from transducers V1 to Vn of probe 10 are used for A/D conversion). Count-up pulses $E500_i$ ($i = 1, 2, \ldots, n$) are sequentially generated from counters $500_i$ which sequentially count up the clock pulses. Therefore, the excitation order and timing of transducers V1 to Vn are determined in accordance with preset data of counters $500_1$ to $500_n$. When all counters $500_1$ to $500_n$ complete the count-up operation, these counters are reset by reset pulse RSR from controller 44. One A/D conversion of reception echo waveforms by a selected set of transducers among transducers V1 to Vn is thus completed.

Figure 14:
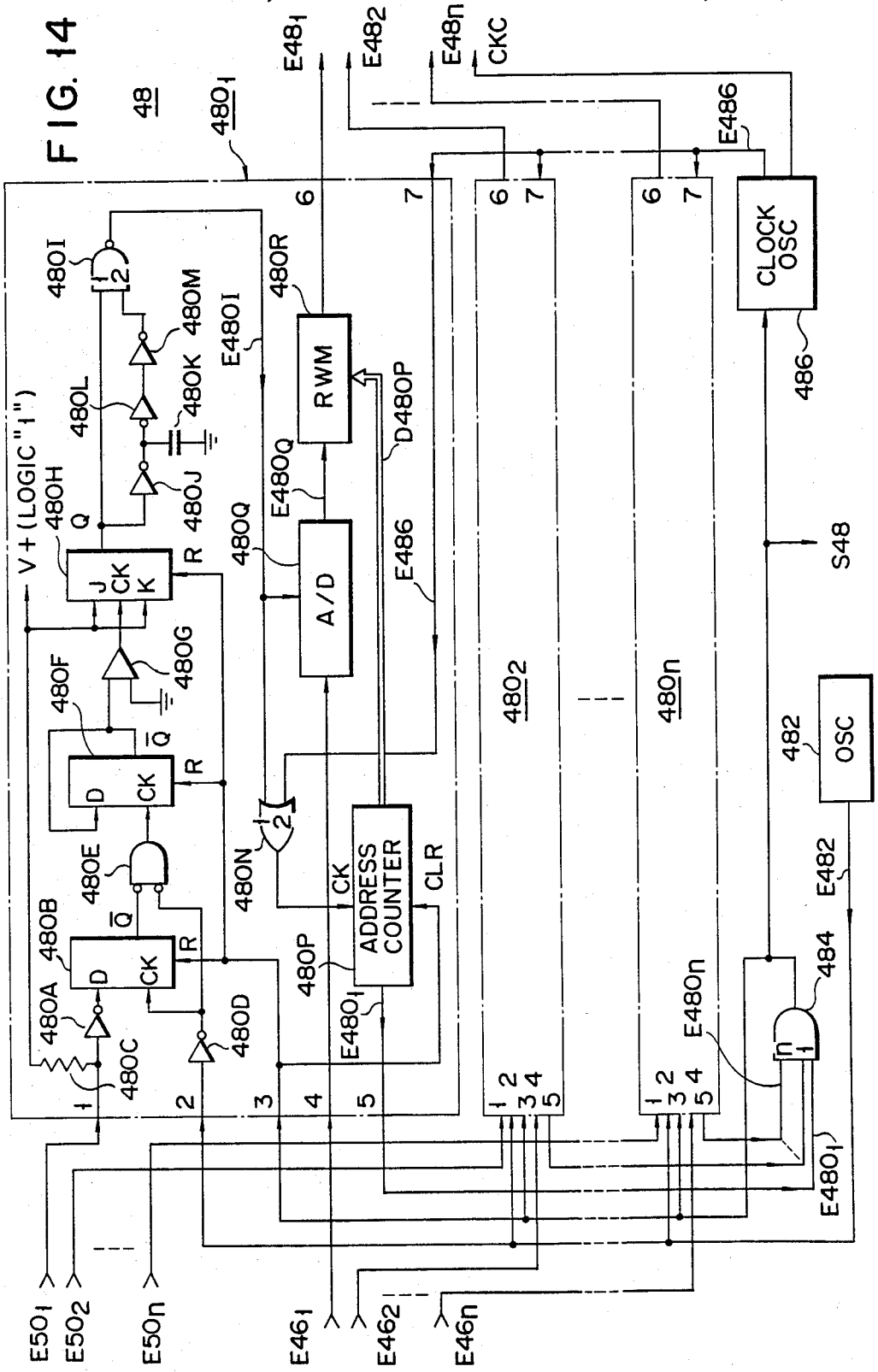
FIG. 14 is a block diagram showing a detailed configuration of A/D converter 48 shown in FIG. 10.

FIG. 14 shows a detailed configuration of A/D converter 48 shown in FIG. 10. Trigger signal $E50_1$ from reception delay controller 50 is supplied to a D input terminal of D flip-flop (D-FF) 480B through inverter 480A. An input terminal of inverter 480A is pulled up through resistor 480C to potential V+ corresponding to logic "1" level. Output pulse E482 is supplied from clock oscillator 482 to clock input terminal CK of D-FF 480B through inverter 480D. A $\overline{Q}$ output signal from D-FF 480B and an output pulse from inverter 480D are supplied to inverting input AND gate 480E. An output pulse from AND gate 480E is supplied to a CK input terminal of D-FF 480F. The $\overline{Q}$ output terminal of D-FF 480F is connected to its D input terminal. The $\overline{Q}$ output signal from D-FF 480F is supplied to the CK input terminal of JK flip-flop (JK-FF) 480H through comparator (operational or op. amplifier) 480G. Signals of logic "1" (V+) are supplied to J and K input terminals of JK-FF 480H, respectively. The Q output signal from JK-FF 480H is supplied to the first input terminal of NAND gate 480I. The Q output signal of JK-FF 480H is also supplied to the second input terminal of NAND gate 480I through inverters 480J, 480L and 480M. An output signal from inverter 480J is bypassed by capacitor 480K to a circuit ground. Therefore, a slight signal delay occurs when the signal is supplied from JK-FF 480H to the second input terminal of NAND gate 480I. Circuit elements 480I to 480M constitute a differentiator having a time constant corresponding to the signal transmission delay. The Q output signal from JK-FF 480H is differentiated and serves as trigger pulse E480I.

Reception signal $E46_1$ is supplied from ultrasonic receiver 46 to A/D converter 480Q. When converter 480Q receives trigger pulse E480I, it converts the corresponding analog signal $E46_1$ to digital signal E480Q. This digital signal E480Q is temporarily stored in read/write memory (RWM) 480R. Address data D480P determines an address for digital signal E480Q. Data D480P corresponds to a count of address counter 480P. Trigger pulse E480I is supplied to clock input terminal CK of counter 480P through the first input terminal of OR gate 480N. Counter 480P is incremented by one every time pulse E480I is supplied thereto, and address data D480P is incremented by one. Digital data E480Q is stored at an address of RWM 480R which corresponds to the count of address counter 480P.

The memory capacity fo RWM 480R corresponds to a maximum count of address counter 480P. For example, when the maximum address of RWM 480R is the 256th address, the largest count of counter 480P is 255. It is thus determined whether or not all the addresses of RWM 480R (256 addresses) are used up in accordance with whether or not counter 480P counts up to the highest count value 255. Counter 480P generates count-up signal $E480_1$ when it compltes the count-up operation.

Circuit elements 480A to 480R constitute first unit $480_1$ among A/D converter units of A/D converter 48. A/D converter 48 also has second to nth units $480_2$ to $480_n$. Each of units $480_2$ to $480_n$ has the same configuration as first unit $480_1$.

Count-up signals $E480_1$ to $E480_n$ of address counters 480P of first to nth units $480_1$ to $480_n$ are supplied to the first to nth input terminals of AND gate 484, respectively. When all address counters 480P have completed the count-up operation, signals $E480_1$ to $E480_n$ are set at logic level "1". Then, AND gate 484 generates signal S48 of logic "1". This signal S48 is used to reset FFs 480B, 480F and 480H and to clear counter 480P. When counter 480P is cleared, signal S48 goes to logic "0", so that the clearing operation of counter 480P is completed.

Signal S48 is not only used as the clear signal but also as the oscillation start/stop signal of clock oscillator 486. When data is written in RWM 480R by trigger pulse E480I, oscillator 486 starts oscillation in response to signal S48. Oscillator output signal E486 from oscillator 486 clocks address counters 480P through the second input terminals of OR gates 480N of first to nth units $480_1$ to $480_n$, respectively. In response to these clocks, the content of address data D480P is incremented by one from 0 to 255. Upon incrementation of address counter 480P, data stored in the RWM 480R of each unit are sequentially read out as signals $E48_1$ to $E48_n$. Data write timings for RWMs 480R of units $480_1$ to $480_n$ differ for the individual units. However, parallel readout operation is performed with respect to each RWM 480R in response to signal E486. Therefore, timings of digital output signals $E48_1$ to $E48_n$ of first to nth units are matched with each other.

When signals are read out from RWMs 480R of all the units $480_1$ to $480_n$ and all the counters 480P have completed the count-up operation, AND gate 484 regenerates signal S48. Signal S48 is used to clear all the counters 480P and to stop oscillator 486. In particular, oscillator 486 oscillates only during a time interval for reading out data from RWM 480R, thereby clocking counter 480P. During this time interval, oscillator 486 generates clock pulse CKC in synchronism with the readout timing of signals E48. AND output signal S48 from AND gate 484 is fetched in host computer 446 through I/O 444 in FIG. 12.

FIG. 15 shows a detailed configuration of add memory 52. Signals $E48_1$ to $E48_n$ are supplied to adder 520. Adder 520 supplied to read/write memory (RWM) 522 an added signal E520 equal to a sum of signals $E48_1$ to $E48_n$. Signal E520 is stored at an address accessed by address data D524. Address data D524 is obtained from the count output of address counter 524. Counter 524 is incremented by clock pulse CKC from osciilllator 486 (FIG. 14) through OR gate 526. One clock pulse CKC is generated every time signals $E48_1$ to $E48_n$ are read out. Thus, address data D524 is incremented by one every time signals $E48_1$ to $E48_n$ are read out. Added signals E520, each comprising a sum of signals $E48_1$ to $E48_n$ read out from RWMs 480R (FIG. 14), are stored in order at a predetermined address of RWM 522 in synchronism with the readout operation of RWMs 480R. Data areas corresponding to all the addresses of RWM 522 are filled by signals E520. At the same time, counter 524 generates count-up pulse ENA.

Pusle ENA is fetched in host computer 446 through I/O 444 (FIG. 12). When host computer 446 receives pulse ENA, it generates reset pulse RSA through I/O 444. Counter 524 (FIG. 15) is cleared in response to pulse RSA, so that a count of counter 524 returns to zero. The first address of RWM 522 is accessed by data D524. Thereafter, when pulse CKA is supplied to the second input terminal of OR gate 526, address data D524 is incremented by one, so that the address contents of RWM 522 which are specified by data D524 are sequentially read out as composite reception signals E52. Pulse CKA is generated in response to start pulse STX produced from host computer 446 through I/O 452 (FIG. 12).

FIGS. 16 to 19 show a detailed configuration of signal processor 54 shown in FIG. 10. Start pulse STX from I/O 452 (FIG. 12) is supplied to clock oscillator 540 (FIG. 16). Oscillator 540 generates clock pulses CKA and CKE have the same frequency and are synchronized with each other. Pulse CKA is supplied to address counter 524 through OR gate 526 so as to clock address counter 524 (FIG. 15). Address data D524 is sequentially incremented. Upon incrementation of address data D524, data (i.e., composite reception signal E52) is read out from RWM 522. Signal E52 is supplied to full-wave rectifier 542 shown in FIG. 16. Rectifier 542 converts negative data components of signal E52 to positive components. The converted components are added to the originally positive components. A conventional rectifier can be used for rectifier 542, and a detailed description thereof will be omitted.

Rectifier 542 supplies rectified output signal WE to comparator 546. The discrimination level DL is supplied to comparator 546. Comparator 546 supplies to D/A converter 548 the discrimination output signal E546 corresponding to a difference (WE−DL) when WE>DL. Comparator 546 generates signal TE of logic "1" when WE>DL or signal E546 is generated. D/A converter 548 converts digital signal E546 corresponding to the difference (WE−DL) to analog signal E548. Signal E548 is used as reception intensity signal ZR for B-scope display 58 (FIG. 10).

The magnitude of discrimination level DL is determined by a key input to input panel 550. Panel 550 supplies to decoder 552 data D550 corresponding to this key input. Discrimination level DL having a predetermined magnitude is produced from decoder 552. This level DL is converted by D/A converter 554 to analog signal YD*. Signal YD* is used as Y-discrimination signal YD of A-scope display 56 in FIG. 10 (cf. FIG. 17).

Clock pulse CKE oscillated from oscillator 540 is supplied to clock input terminal CK of up-counter 556. Clock pulse CKE is synchronous with clock pulse CKA. Clock pulse CKA determines a read rate of RWM 522 shown in FIG. 15. When it is assumed that the frequency of clock pulses CKA and CKE is kept at a predetermined value, the number of pulses CKA or CKE corresponds to the beam propagation path length T. Count output signal CE from up-counter 556 (FIG. 16) becomes data indicating beam propagation path length T. Here note that up-counter 556 is reset by reset pulse RSX from I/O 452 (FIG. 12) and supplies count-up signal END1 to host computer 446 through I/O 452 upon completion of the count-up operation.

Count output signal CE from counter 556 is supplied to subtractor 560. Digital data $\Delta T$ is supplied from latch 564 to subtractor 560 (where $\Delta T$ will be described later on). Subtractor 560 generates signal E560 corresponding to a difference (T−$\Delta T$) of input data. Signal E560 is converted by D/A converter 562 to analog signal E562. Signal E562 is then supplied to multiplier 582. Multiplier 582 also receives digital data −sin$\beta$j from latch 570 (−sin$\beta$j will be described in detail later). Multiplier 582 includes a D/A converter and generates signal E582 corresponding to a product of the analog-converted −sin$\beta$j and analog signal E562 (i.e., (T−$\Delta T$)(−sin$\beta$j)).

Count output signal CE from counter 556 is converted by D/A converter 558 to analog signal E558. Signal E558 is supplied to multipliers 578, 580 and 584. Digital data cos$\beta$j, cos$\alpha$i and sin$\alpha$i are supplied from latches 566, 568 and 572 to multipliers 578, 580 and 584, respectively (cos⊕j, cos$\alpha$i and sin$\alpha$i will be described in detail later). Multipliers 578, 580 and 584 include D/A converters, respectively. Multiplier 578 generates signal E578 corresponding to analog signal produce E558×cos$\beta$j (Tcos$\beta$j); multiplier 580 generates signal E580 corresponding to analog signal product E558×cos$\alpha$i (Tcos$\alpha$i); and multiplier 584 generates signal E584 corresponding to analog signal product E558×sin$\alpha$i (Tsin$\alpha$i).

Analog signal E582 is supplied to adder 590. Adder 590 also receives analog output signal E586 from D/A converter 586. Output signal E586 corresponds to digital data $(L^* - \overline{AC_\beta})$ from latch 574 [$(L^* - \overline{AC_\beta})$ will be described later in detail later]. Adder 590 generates signal sum (E586+E582), i.e., analog signal E590 corresponding to $L^* - \overline{AC_\beta} - (T - \Delta T)\sin\beta j$.

Analog signal E584 is supplied to adder 592. Adder 592 also receives analog output signal E588 from D/A converter 588. This output signal E588 corresponds to digital data $\overline{AC_\alpha}$ from latch 576 ($\overline{AC_\alpha}$ will be described in detail later). Adder 592 generates signal sum (E588+E584), i.e., analog signal E592 corresponding to $\overline{AC_\alpha} + T\sin\alpha i$.

Data $\Delta T$, $\cos\beta j$, $\cos\alpha i$, $-\sin\beta j$, $\sin\alpha i$, $L^* - \overline{AC_\beta}$ and $\overline{AC_\alpha}$ which are latched by latches 564 to 576, respectively, are supplied from slave computer 692 (to be described later with reference to FIG. 19) through data bus DB. These data are latched by latches 564 to 576 at timings determined by latch signals $E594_1$ to $E594_7$ from decoder (ROM) 594. The readout addresses of ROM 594 are accessed by slave computer 692 (FIG. 19) through address bus AB. ROM 594 produces latch signal LE (to be described later) in accordance with specific address data on address bus AB.

Output signal E578 from multiplier 578 is used as Y-reception signal YR of B-scope display 58 (FIG. 10), and output signal E590 from adder 590 is used as X-reception signal XR of B-scope display 58. Similarly, output signal E580 from multiplier 580 is used as Y-transmission signal YT of B-scope display 58, and output signal E592 from adder 592 is used as X-transmission signal XT thereof. Fixed potential V+ is used as transmission intensity signal ZT.

Figure 17:
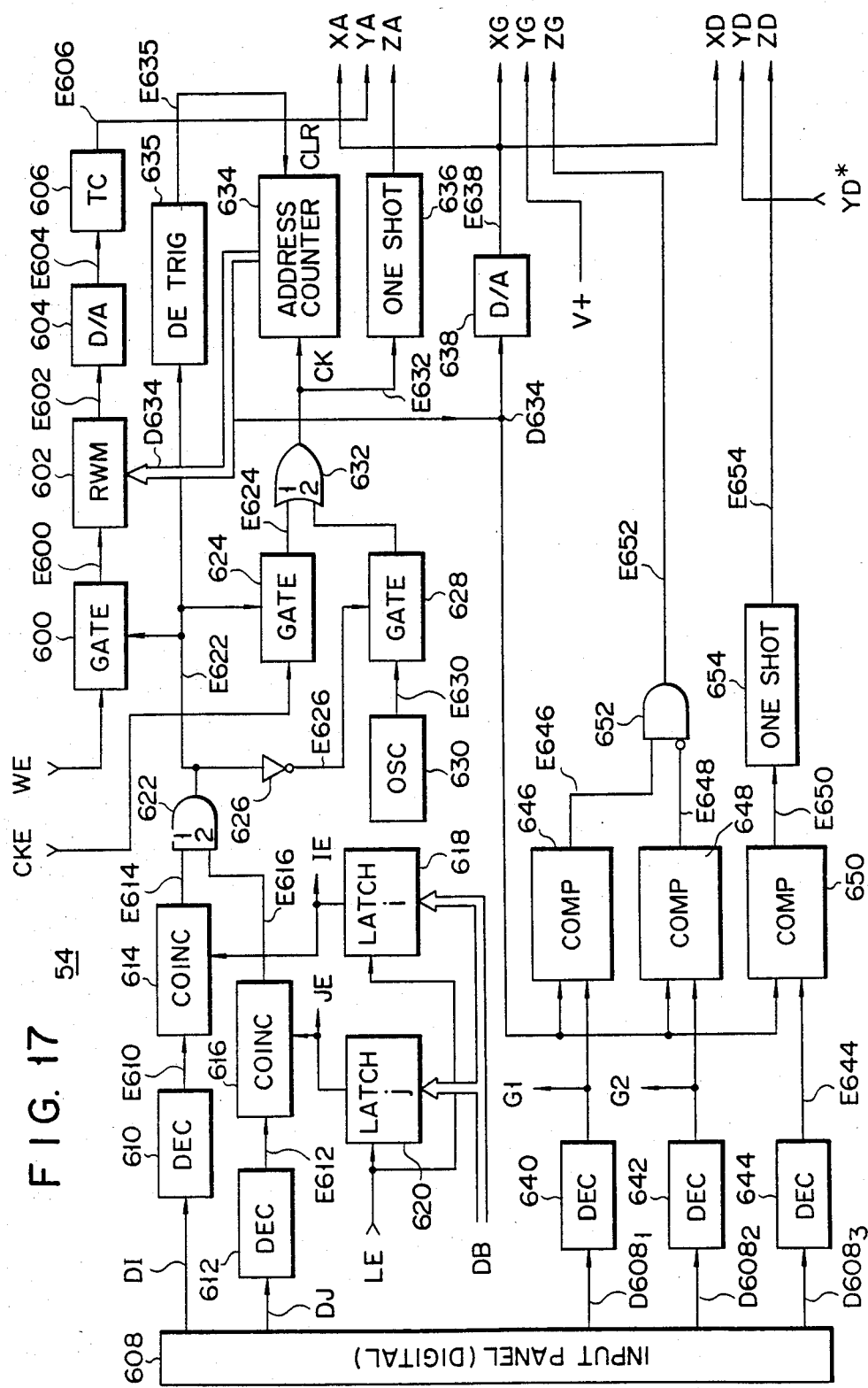

Rectified output WE (FIG. 16) is supplied to gate 600 in FIG. 17. When gate signal E622 is set at logic "1", gate 600 passes rectified output WE and supplies gated output E600 to read/write memory (RWM) 602. Gated output E600 is written at an address of RWM 602 which is accessed by address data D634 supplied from address counter 634. Clock pulse CKE from oscillator 540 (FIG. 16) is used as a write clock for counter 634. When gate signal E622 is set a logic "1", pulse CKE is passed through gate 624 and then becomes gated output E624. Gated output E624 is supplied to the first input terminal of OR gate 632. OR output E632 from OR gate 632 is supplied to clock input terminal CK of counter 634.

Clock pulses CKA and CKE from oscillator 540 in FIG. 16 have the same frequency and are synchronized with each other. Clock pulse CKA determines a read rate of RWM 522 in FIG. 15, whereas clock pulse CKE determines a write rate of RWM 602 in FIG. 17. Composite reception signal E52 read out from RWM 522 in FIG. 15 corresponds to rectified output WE from rectifier 542 in FIG. 16. Therefore, when gates 600 and 624 in FIG. 17 are held open and oscillator 540 in FIG. 16 oscillates, data (E600) corresponding to data (E52) read out from RWM 522 (FIG. 15) is written in RWM 602 (FIG. 17) at the same rate as the read rate.

Data is read out from RWM 602 after gate signal E622 goes to logic "0" and gates 600 and 624 are closed. Signal E622 is inverted to inverted gate signal E626 by inverter 626. This signal E626 is supplied to gate 628. When signal E626 is set at logic "1" (i.e., when signal E622 is set at logic "0"), gate 628 is opened. When gate 628 is opened, clock pulse E630 from clock oscillator 630 is supplied to clock input terminal CK of counter 634 through gate 628 and OR gate 632. In this case, counter 634 is incremented in response to pulse E630, so that the contents of RWM 602 are read out at a rate corresponding to the frequency of pulse E630.

Address counter 634 is cleared by output pulse E635 from double edge trigger circuit 635. Circuit 635 generates a single pulse E635 every time it is triggered at a zero-crossing point (i.e., the leading edge corresponding to a zero-crossing point from logic "0" to logic "1∞", and the trailing edge corresponding to a zero-crossing point from logic "1" to logic "0"). Therefore, counter 634 is cleared immediately after gates 600 and 624 are opened. The count of counter 634 is incremented by one from count "0" in response to each pulse CKE (write mode). Counter 634 is cleared immediately after gates 600 and 624 are closed. Thereafter, the count of counter 634 is incremented by one in response to pulse E630 from count "0" (read mode).

Digital data E602 read out from RWM 602 is converted by D/A converter 604 to analog signal E604. The envelope of signal E604 has an abrupt level change. However, this change can be smoothed by time constant circuit (low-pass filter) 606. Output E606 from circuit 606 is used as Y-waveform signal YA for A-scope display 56 in FIG. 10. X-waveform signal XA therefor is obtained from D/A converter 638 by converting count output D634 from address counter 634 to analog signal E638. A-scope Z-intensity signal ZA therefor is obtained from one-shot 636 triggered by OR output E632.

Gate signal E622 is produced in the following manner. Data DI for specifying steered angle $\alpha i$ of the ultrasonic main beam and data DJ for specifying steered angle $\beta j$ of the ultrasonic main beam are produced at input panel 608. Data DI is decoded by decoder 610 to digital signal E610, while data DJ is decoded by decoder 612 to digital signal E612. Signals E610 and E612 are supplied to coincidence sensors 614 and 616, respectively. Sensor 614 receives digital signal IE from latch 618, while sensor 616 receives digital signal JE from latch 620. When signal IE coincides with signal E610, sensor 614 supplies coicidence output E614 to the first input terminal of AND gate 622. When signal JE coicides with signal E612, sensor 616 supplies coincidence output E616 to the second input terminal of AND gate 622. When coincidence outputs E614 and 616 are simultaneously generated, AND gate 622 generates gate signal E622 of logic "1".

Data i and j respectively latched by latches 618 and 620 are supplied from slave computer 692 (FIG. 19) through data bus DB. When data i and j run on data bus DB, computer 692 supplies address data for generating latch signal LE to ROM 594 (FIG. 16) through address bus AB. Data i and j are respectively stored in latches 618 and 620 in response to latch signal LE from ROM 594.

Data $D608_1$, $D608_2$ and $D608_3$ are entered by key inputs at input panel 608 shown in FIG. 17. Data $608_1$ indicates a start point of a time-base gate. Data $608_2$ indicates an end point of the time-base gate. Data $608_3$ indicates a brightened spot start point (or unblanking release point) of A-scope display 56. Data $D608_1$ is decoded by decoder 640 to digital gate signal G1. Data $D608_2$ is decoded by ecoder 642 to digital gate signal G2. Data $608_3$ is decoded by decoder 644 to brightened spot start signal E644.

Signals G1, G2 and E644 are supplied to comparators 646, 648 and 650, respectively. Comparators 646, 648 and 650 also receive count output D634 of address counter 634. When the count of counter 634 exceeds signal G1 (i.e., G1<D634), comparator 646 supplies comparison output E646 of logic "1" to the noninverting input terminal of AND gate 652. When the count of counter 634 is smaller than signal G2 (i.e., D634<G2), comparator 648 supplies comparison output E648 of logic "0" to the inverting input terminal of AND gate 652. When E646="1" and E648="0", AND gate 652 produces signal E652 of logic "1". E646="1" is obtained if G1<D634. However, E648="0" is obtained if D634<G2. Therefore, if G1<D634<G2, signal E652 is produced. Signal E652 is used as intensity signal ZG of A-scope display 56 (Fig. 10). Fixed potential V+ is used as Y-signal YG of A-scope display 56. Analog output E638 from D/A converter 638 is used as X-signal XG.

When the count of counter 634 exceeds signal E644 (i.e., E644<D634), comparator 650 supplies comparison output E650 of logic "1" to one-shot 654. One-shot 654 generates signal E654 of logic "1" for a predetermined time interval after output E650 goes from logic "0" to logic "1". Signal E654 is used as Z-discrimination signal ZD of A-scope display 56 (FIG. 10). Y-discrimination signal YD of A-scope display 56 is obtained from D/A converter 554 (FIG. 16). Analog output E638 from D/A converter 638 is used as X-discrimination signal XD of A-scope display 56.

Figure 18:
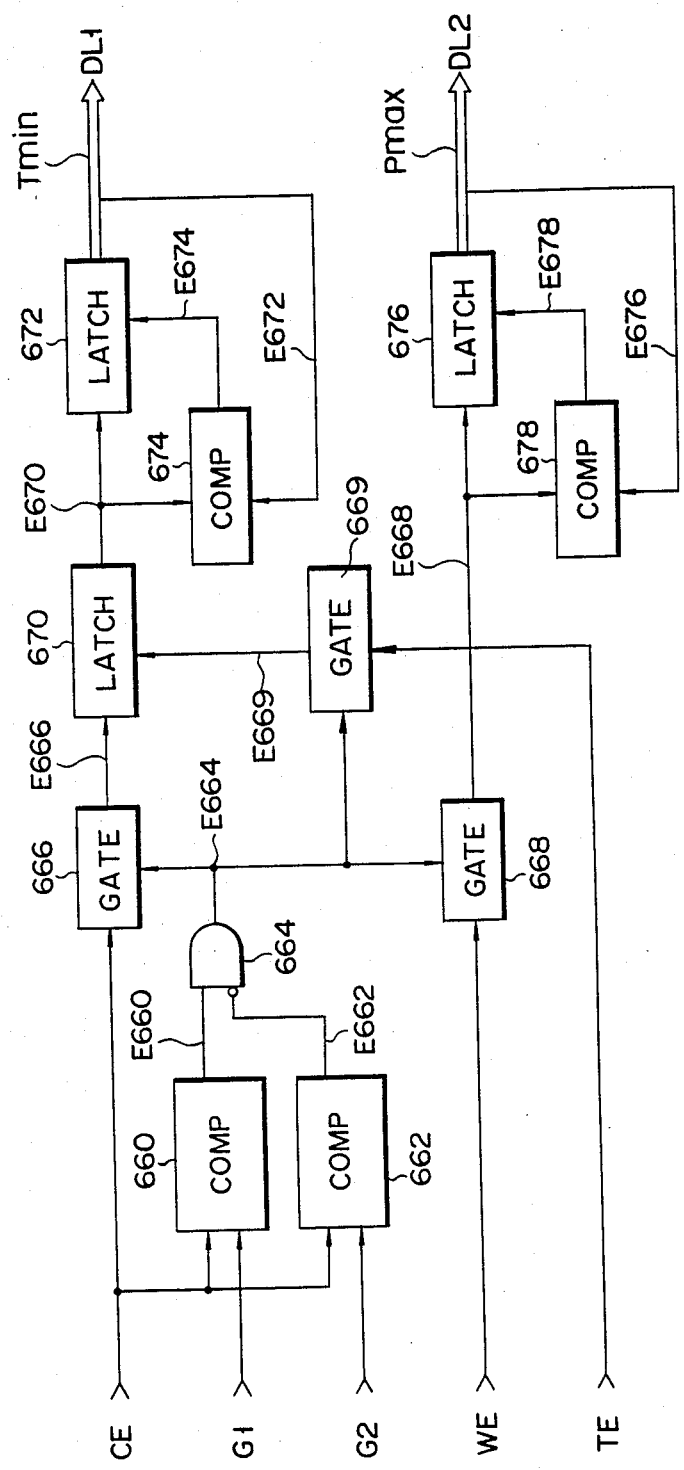

FIG. 18 shows a circuit configuration for presetting a gate range along the time base (X-axis) of rectified output WE corresponding to composite reception signal E52. Count output CE (corresponding to beam propagation path length T) of counter 556 (FIG. 16) is supplied to comparators 660 and 662 and to gate 666. Comparator 660 also receives gate signal G1 from decoder 640 (FIG. 17). When G1<CE, comparator 660 supplies comparison output E660 of logic "1" to the noninverting input terminal of AND gate 664. Gate signal G2 is supplied from decoder 642 (FIG. 17) to comparator 662. When CE<G2, comparator 662 supplies comparison output E662 of logic "0" to the inverting input terminal of AND gate 664. When E660="1" and E662="0", AND gate 644 produces gate signal E664 of logic "1".

Gate signal E664 is supplied to gates 666, 668 and 669. Gate 666 causes count output CE to pass therethrough and gate 669 causes signal TE to pass therethrough, when E664="1". Output CE from gate 666 is supplied to latch 670. In this case, output CE is regarded as signal E666 indicating the beam propagation path length within a given time interval determined by signals G1 and G2. When latch 670 receives signal TE via gate 669 from comparator 546 (FIG. 16), it latches signal E666.

Signal E666 latched by latch 670 is supplied as latched signal E670 to latch 672 and comparator 674. Comparator 674 compares latched signal E672 with signal E670. When E670≧E672, comparator 674 does not produce any output. However, when E670<E672, comparator 674 supplies latch pulse E674 to latch 672. The content of latch 672 changes to a content corresponding to signal E670 smaller than signal E672 (before latching). A minimum value among various values of signal E670 is stored in latch 672. In this manner, latch 672 sends data representing minimum beam propagation path length Tmin within a gate range determined by gate signals G1 and G2 to IN port 694 (FIG. 19) via data line DL1.

Gate 668 also receives rectified output WE from rectifier 542 (FIG. 16). Gate 668 allows rectified output WE to pass therethrough when gate signal E664 is set at logic "1". Output WE passing through gate 668 is supplied as signal E668 to latch 676 and comparator 678. Signal E668 indicates the amplitude component of reception echo signals occurring during the interval given by gate signals G1 and G2. Comparator 678 compares signal E668 with latched signal E676 of latch 676. When E668≧E676, comparator 678 does not produce any output. However, when E668>E676, comparator 678 supplies latch pulse E678 to latch 676. The content of latch 676 is then updated to the content corresponding to signal E668. Signal E668 is larger than signal E676 before latching. A maximum value among various values of signal E668 is stored in latch 676. As a result, latch 676 sends data indicating maximum value Pmax to IN port 694 via data line DL2. Maximum value Pmax is selected from reception echo signals within the range given by signals G1 and G2.

Figure 19:
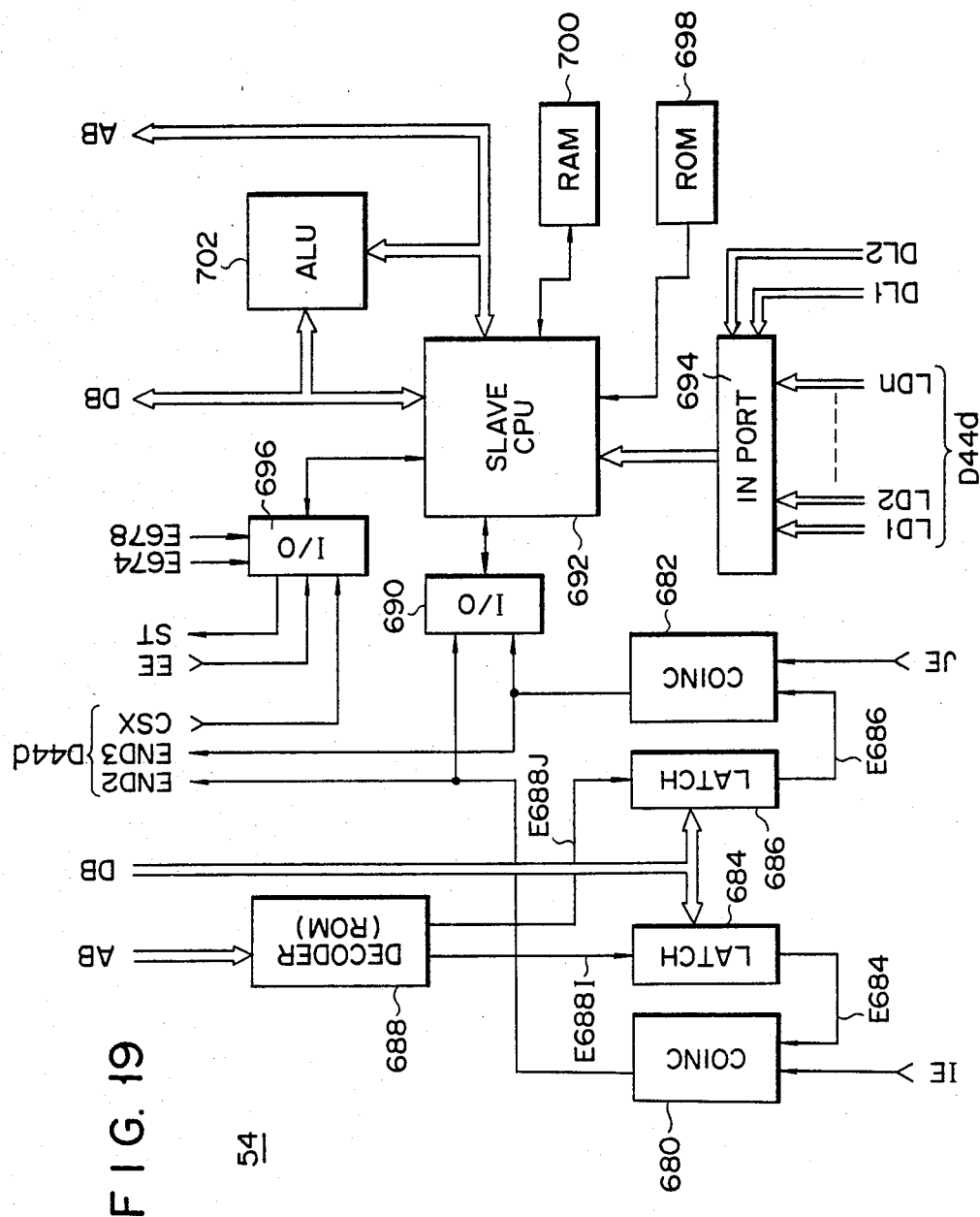

FIG. 19 shows a configuration of a part of a circuit of signal processor 54 (FIG. 10) mainly for controlling arithmetic operation. Coincidence sensor 680 receives digital signal IE from latch 618 (FIG. 17), while coincidence sensor 682 receives digital signal JE from latch 620 (FIG. 17). Concidence sensor 680 also receives signal E684 for specifying the maximum value of parameter i in single transmission scanning. For example, when steered angle αi changes from 0° to 90° in increments of 10°, steered angles are given as follows: $\alpha_1=0°$, $\alpha_2=10°$, ... and $\alpha_{10}=90°$. The maximum value of parameter i is 10 (decimal notation). In this case, signal E684 is data corresponding to decimal 10. Similarly, coincidence sensor 682 also receives signal E686 for specifying the maximum value of parameter j in single reception scanning. When steered angle βj changes from 0° to 90° in increments of 10°, signal E686 is data correponding to decimal 10.

Data to be latched by latches 684 and 686 are supplied from computer 446 (FIG. 12) through data bus DB. The latch timing of data on bus DB is determined by address data supplied from computer 446 to decoder (ROM) 688 through address bus AB. When computer 446 supplies latch data to latches 684 and 686 through data bus DB, computer 446 also supplies predetermined address data to ROM 688 through address bus AB. Latch pulses E688I and E688J are then supplied from ROM 688 to latches 684 and 686, respectively. Thus, data corresponding to signals E684 and E686 are supplied from data bus DB and are respctively latched by latches 684 and 686.

Data IE of parameter i which is latched by latch 618 (FIG. 17) changes from a predetermined minimum value to a predetermind maximum value (corresponding to E684) during transmission scanning. Data JE of parameter j which is latched by latch 620 (FIG. 17) changes from a predetermined minimum value to a predetermined maximum value (corresponding to E686) during reception scanning. When signal IE coicides with signal E684, coincidence sensor 680 in FIG. 19 supplies signal END2 to computer 446 through I/O 452 (FIG. 12). Similarly, when signal JE coincides with signal E686, coincidence sensor 682 (FIG. 19) supplies signal END3 to computer 446 through I/O 452. Host computer 446 determines the transmission scanning end by signal END2 and the reception scanning end by signal END3. Signals END2 and END3 are also supplied to slave computer 692 through I/O 690. Computer 692 fetches latched data LD1 to LDn from latches $456_1$ to $456_n$ (FIG. 12) through IN port 694. These data LD1 to LDn are used to evaluate the flaw dimension d of the tested body. Computer 692 also fetches data Tmin (E672) and Pmax (E676) from latches 672 and 676 (FIG. 18) via IN port 694, and signals E674 and E678 from latches 674 and 678 (FIG. 18) via I/O 696. Computer 692 is informed by signal E674 or E678 that latch 672 or 676 performs the latching operation. Reception steered angles $\beta m$ are detected by computer 692 in accordance with signals E674 and E678.

When host computer 446 (FIG. 12) determines the end of the count of beam propagation path length T in response to signal END1 and the ends of transmission and reception scanning operations in response to signals END2 and END3, respectively, computer 446 supplies control signal CSX to slave computer 692 through I/O 452 (FIG. 12) and I/O 696 (FIG. 19). Computer 692 then causes arithmetic and logic unit (ALU) 702 to execute a predetermined arithmetic operation in accordance with a microprogram, etc. stored in ROM 698 and a predetermined program, etc. stored in RAM 700. This arithmetic operation will be described in detail later. Slave computer 692 and ALU 702 may comprise the same microcomputer (#8048, Z-80 or the like) as host computer 446 (FIG. 12).

Figure 20:
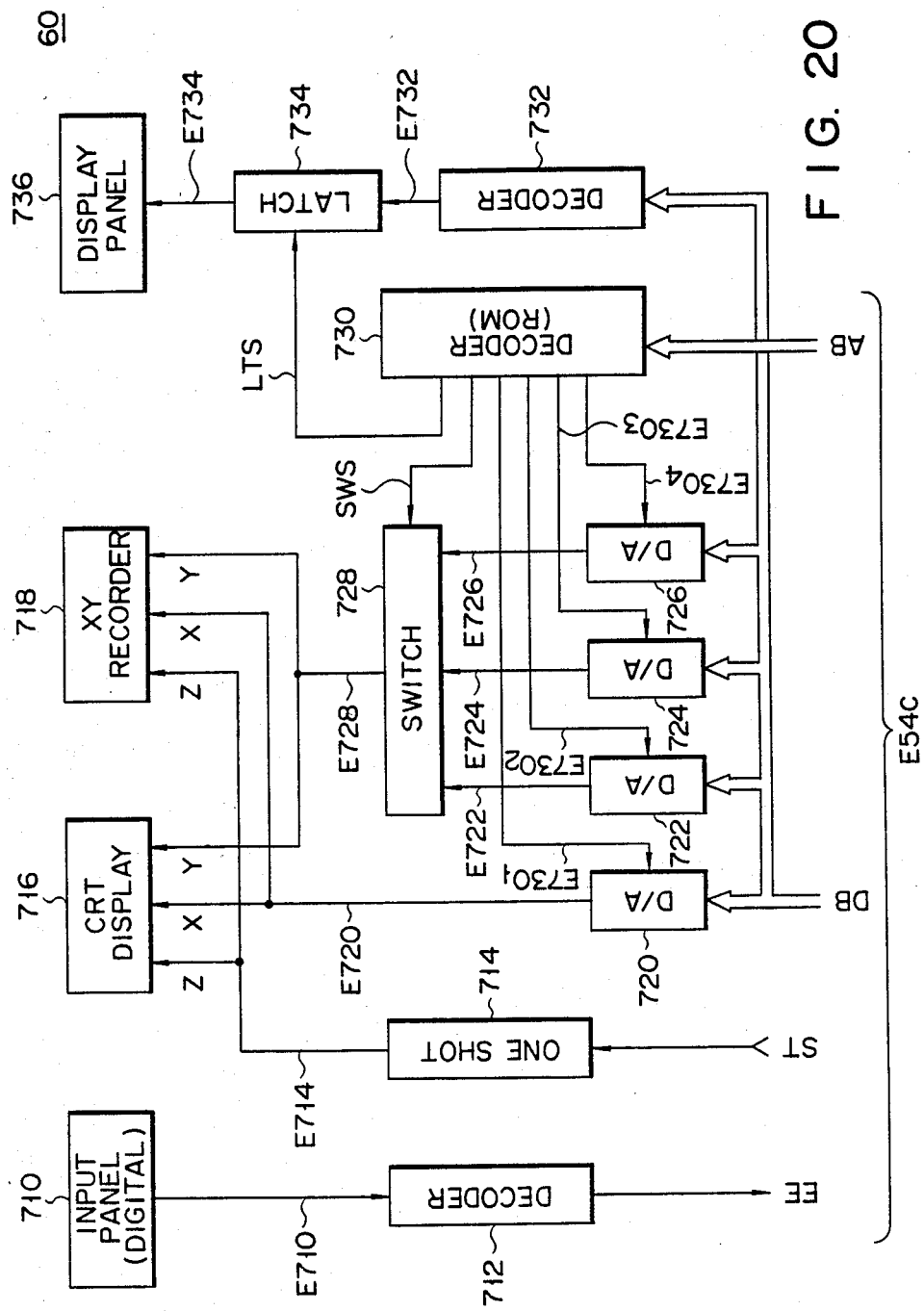
FIG. 20 is a block diagram showing a detailed configuration of record display 60 shown in FIG. 10.

FIG. 20 shows a detailed configuration of record display 60 (FIG. 10). An operator enters data D710 at input panel 710 to perform recording and display at display 60. Data D710 is decoded by decoder 712 to record/display designation signal EE. Signal EE is fetched by computer 692 through I/O 696 (FIG. 19). When computer 692 receives signal EE, it generates start signal ST through I/O 696 immediately after signal END3 is generated. Signal ST is used to trigger one-shot 714 in FIG. 20. When one-shot 714 is triggered, it immediately generates Z-signal E714 for a predetermined time interval. Signal E714 is supplied to Z-input terminals of CRT display 716 and X-Y recorder 718.

Analog X-signal E720 is supplied from D/A converter 720 to X-input terminals of CRT display 716 and X-Y recorder 718. Analog Y-signal E728 is supplied from switching circuit 728 to Y-input terminals of CRT display 716 and X-Y recorder 718. Converted outputs E722, E724 and E726 are respectively supplied from D/A converters 722, 724 and 726 to switching circuit 728. Switching circuit 728 selects as Y-signal E728 one of signals E722 to E726 in accordance with switching instruction signal SWS from decoder (ROM) 730.

Digital data are supplied from computer 692 (FIG. 19) to the respective D/A converters 720 to 726 through data bus DB. The data supplied to D/A converter 726 is latched signal E627 from latch 672 (FIG. 18). Signal E672 indicates a minimum length Tmin among beam propagation path lengths T detected during single reception scanning. Data supplied to D/A converter 724 is latched signal E676 from latch 676 (FIG. 18). Signal E676 indicates maximum amplitude Pmax of signal E52 or WE indicating ultrasonic echo signals detected during single reception scanning. Data supplied to D/A converter 722 indicates steered angles $\beta j$ (i.e. $\beta m$) when data Tmin and Pmax are obtained. Data supplied to converter 720 indicates steered angle $\alpha i$ when data Tmin, Pmax and $\beta m$ are detected.

ROM 730 determines an order of conversion of data $\alpha i$, $\beta m$, Pmax, and Tmin on data bus DB by means of D/A converter 720 to 726. When data $\alpha i$ runs on data bus DB, enable signal $E730_1$ is supplied from ROM 730 to D/A converter 720 in response to address data on address bus AB. Only D/A converter 720 is enabled to supply signal E720 corresponding to data $\alpha i$ to CRT display 716 and X-Y recorder 718. When data $\beta m$ runs on data bus DB, enable signal $E730_2$ is supplied to D/A converter 722 is response to address data on address bus AB. Only D/A converter 722 is enabled to supply signal E722 corresponding to data $\beta m$ to switching circuit 728. When enable signal $E730_2$ is generated, switching instruction signal SWS selects signal E722. Similarly, when data Pmax runs on data bus DB, enable signal $E730_3$ is supplied to D/A converter 724, so that switching circuit 728 selects output E724 from D/A converter 724. When data Tmin runs on data bus DB, enable signal $E730_4$ is supplied to D/A converter 726. In this case, switching circuit 728 selects output E726 from D/A converter 726. Signal E728 (corresponding to one of data $\eta m$, Pmax, and Tmin) selected by switching circuit 728 is supplied to CRT display 716 and X-Y recorder 718. In CRT display 716 and X-Y recorder 718, data $\alpha i$ (E720) is used as an X variable, whereas data $\beta m$ (E722), Pmax (E724) or Tmin (E726) is used as a Y-variable, thereby displaying and recording data on a two-dimensional graphic display screen.

Operation results (e.g., flaw dimension of the tested body) obtained by ALU 702 (FIG. 19) also run on data bus DB. These operation results are decoded by decoder 732 to signal E732. Signal E732 is supplied to latch 734. Latch signal LTS is supplied from ROM 730 to latch 734 in accordance with address data on address bus AB when the operation results run on data bus DB. Latch 734 then latches signal E732. Signal E732 latched by latch 734 is displayed as operation result signal E734 on display panel 736. The flaw dimension and other numeric values are displayed on display panel 736.

The operation of the apparatus shown in FIGS. 10 to 20 will now be described in detail.

Figure 21:
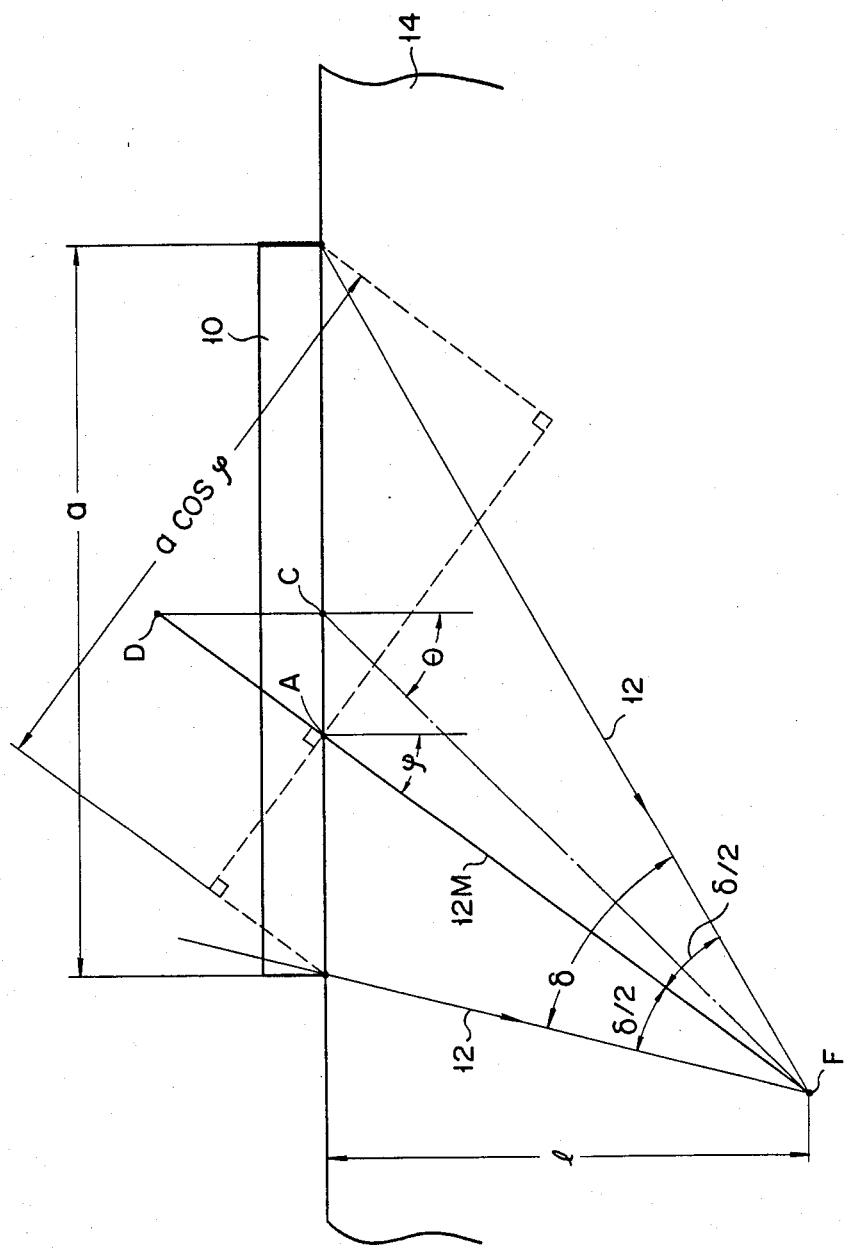
FIG. 21 shows geographical relationships among aperture size a of a set of ultrasonic transducers, ultrasonic steered angle $\theta$ with respect to central point C of the opening, steered angle $\phi$ of main beam 12M with respect to ultrasonic transmission/reception beam index point A, and convergence path length l.

FIG. 21 shows a geometric relationship among aperture size a of the set of ultrasonic transducers, steered angle $\theta$ with respect to the center or central point C of the opening, steered angle $\phi$ of ultrasonic main beam 12M with respect to actual transmission/reception beam index point A, and ultrasonic convergence path length l. In order to conerge ultrasonic beams 12 on focal point F, ultrasonic transmission/reception timings of transducers V1 to Vn of probe 10 are controlled by transmission delay controller 42 and reception delay controller 50 in FIG. 10, in accordance with a predetermined sequence. This control is performed such that the ultrasonic beams propagate in a direction at steered angle $\theta$ with respect to the line normal to central point C. The direction of ultrasonic main beam 12M returning from focal point F to probe 10 coincides with a bisector, which bisects an angle $\sigma$ between two lines connected between the right and left ends of the opening and focal point F to obtain two angles $\sigma/2$. Unless focal point F is located immediately under central point C, return point A of ultrasonic main beam 12M incident again on probe 10 is misaligned from central point C. In other words, actual ultrasonic transmission/reception beam index point A differs from central point C of the opening of probe 10.

Angle $\phi$ formed by maim beam 12M and normal to point A can be obtained from the following equation when length l between the surface of tested body 14 and focal point F, aperture size a, and steered angle $\theta$ from central point C are given:

$$\phi = \tfrac{1}{2}\{\tan^{-1}(\tan\theta + a/2l) + \tan^{-1}(\tan\theta - a/2l)\} \tag{1}$$

When angle $\phi$ is calculated from equation (1), distance $\overline{AC}$ between points A and C is obtained as follows:

$$\overline{AC} = \{(\sqrt{1 + ((a/2l)\sin 2\phi)^2} - 1)/\sin 2\phi\} \times l \quad (2)$$

Figure 8:
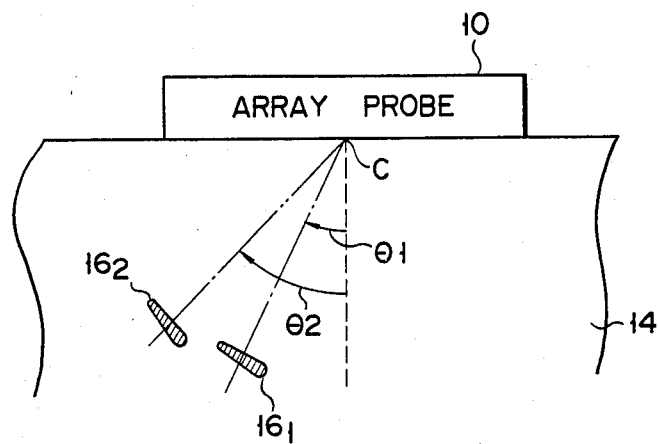
FIG. 8 shows a case in which two internal flaws are searched by sector scanning.
Figure 9:
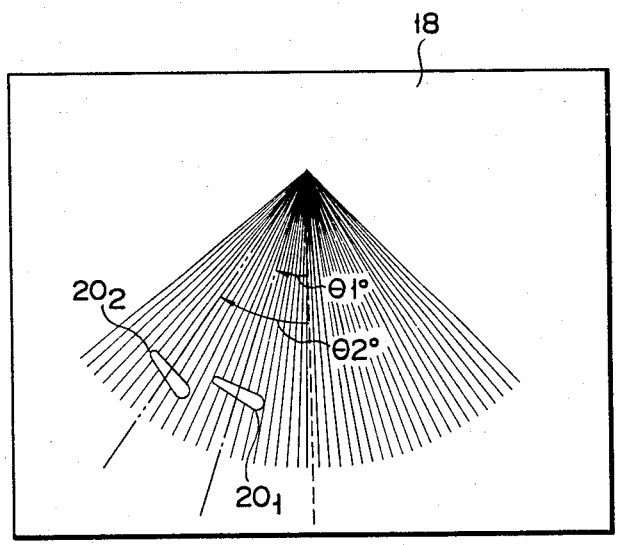
FIG. 9 shows a state wherein angular positions $\theta 1°$ and $\theta 2°$ of flaw images displayed by a B-scope display are not aligned with angular positions $\theta 1$ and $\theta 2$ of flaws shown in FIG. 8.

In this manner, when distance $\overline{AC}$ is obtained, point A can be determined since point C is known. The image sweep start point on the CRT of B-scope display 58 is determined by equation (2), and the sweep direction is determined by equation (1). Image signals E54 (especially signal E54b) are produced in synchronism with composite reception signal E52 from add memory 52 (FIG. 10) in accordance with data indicating transmission/reception beam index point A and data indicating steered angle $\phi$ of ultrasonic main beam 12M. These data are calculated from equations (1) and (2) and are used instead of data indicating point C and angle $\theta$. As a result, the misalignment of detected flaw portion 16 on the CRT display due to misalignment of point A from point C can be prevented. More particularly, angular positions $\theta 1°$ and $\theta 2°$ (FIG. 9) of the B-scope image showing flaw portions $20_1$ and $20_2$ match the actual angular positions $\theta 1$ and $\theta 2$ (FIG. 8) of flaw portions $16_1$ and $16_2$, respectively.

When the aperture size a is much less than a distance twice the convergence distance (i.e., $a/2l < < 1$), equation (2) can be simplified as follows:

$$\overline{AC} \approx (a^2/8l) \cdot 2\phi \quad (3)$$

In particular, when $a/2l < < 1$, equation (3) may be used instead of equation (2) so as to determine transmission/reception beam index point A.

Referring to FIG. 21, an intersection between a line normal to point C and a line connecting points F and A is given as D; distance $\overline{DC}$ between points D and C is given as follows:

$$\overline{DC} = \overline{AC}/\tan\phi = (\tfrac{1}{4}l) (a \cdot \cos\phi)^2 \quad (4)$$

Assume that point D in FIG. 21 is the sweep start point on B-scope display 58, and that term $a \cdot \cos\phi$ is a constant. When tested body 14 is tested under these conditions, start point D is fixed. In this case, a width of spread transmitted beams incident on a plane perpendicular to ultrasonic main beam 12M can be regarded as a constant irrespective of steered angle $\phi$. In this case, a certain change in the testing characteristic concerning the opening size of transducers (i.e., a change in steered angle $\phi$ in the distance-amplitude characteristic curve) need not be considered.

Figure 22:
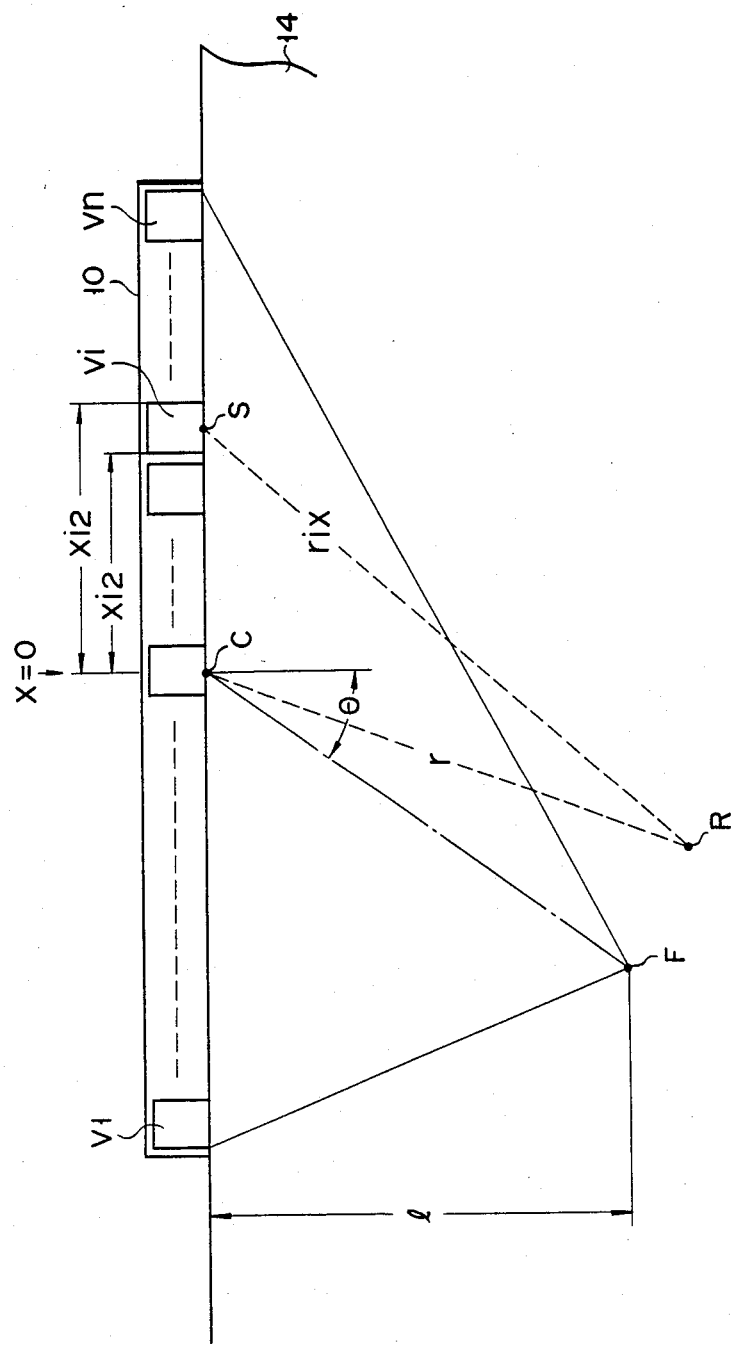
FIG. 22 is a diagram for explaining directivity of an acoustic field in tested body 14.

Referring to FIG. 21, the intensity of ultrasonic main beam 12M incident on point F is decreased when the propagation direction of main beam 12M is misaligned from the line connecting points F and A. The degree of decrease in the incident intensity is increased when distance $\overline{AC}$ of transmission/reception beam index point A from point C is large. When $\overline{AC}$ is increased, the directivity of an acoustic field is intense along main beam 12M. The directivity of an acoustic field of a single transducer among the transducers of probe 10 will be described with reference to FIG. 22. Referring to FIG. 22, a single transducer Vi of probe 10 indicates the ith transducer with respct to central point C. A distance between point C and the right end [(i+1)th transducer side] of transducer Vi is designated by Xi2, and a distance between point C and the left end [(i−1)th transducer side] of transducer Vi is designated by Xi1.

When a point selected for calculating the acoustic characteristic inside tested body 14 is designated as R, a distance between points R and C is designated by r, and a distance between point R and central point S of transducer Vi is designated by $r_{ix}$. In this case, directivity characteristic Ei of the acoustic field of transducer Vi is given as follows:

$$Ei = \left| \int_{xi1}^{xi2} Ai(x) \cdot \{V(t - r/u)/r\} \cdot e^{j(\omega t - kr_{ix})}dx \right| \quad (5)$$

where u is the sonic velocity inside tested body 14, k is $2\pi/\lambda$ ($\lambda$ is the wavelength), $\omega$ is the angular frequency of the ultrasonic wave, t is time, Ai(x) is the sensitivity characteristic of the ith transducer Vi, and V(t) is the pulse waveform of the ultrasonic wave.

Directivity characteristics E of the acoustic field of n transducers V1 to Vn can be given by $$\sum_{i=1}^{n} Ei,$$

so that $$E = \left| \sum_{i=1}^{n} \int_{xi1}^{xi2} Ai(x) \cdot \{V(t - r/u - ti)/r\} \cdot e^{j(\omega t - kr_{ix} - \omega ti)}dx \right| \quad (6)$$

where ti is the time determined by present convergence path length l, preset steered angle $\theta$, sonic velocity u, and the geometric position of transducer Vi, and Ai(x) and V(t) are values obtained by experiment. Data Ai(x) and V(t) at the time of transmission can be dealt with in the same manner as data Ai(x) and V(t) at the time of reception.

Figure 23:
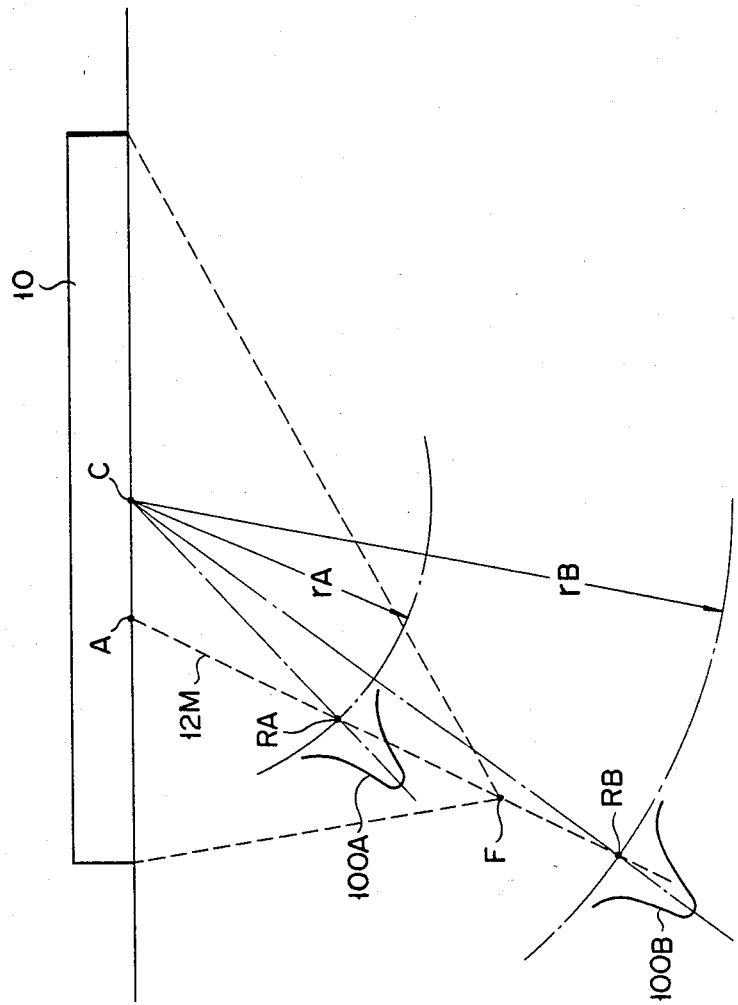
FIG. 23 shows directivity of an acoustic field in tested body 14, the directivity being obtained by calculation.

FIG. 23 shows the directivity of the acoustic field which is calculated by equation (6). When parameter r in equation (6) is given as rA, sound pressure distribution curve 100A of the ultrasonic beam is obtained. Similarly when parameter r is given as rB, sound pressure distribution curve 100B is obtained. A maximum sound pressure for parameter rA occurs at point RA, whereas a maximum sound pressure for parameter rB occurs at point RB. A line connecting maximum sound pressure points RA and RB indicates the direction of ultrasonic main beam 12M. An intersection between this line and probe 10 corresponds to actual transmission/reception beam index point A.

As may be apparent from the above description, a plurality of maximum sound pressure points RA and RB are obtained from directivity characteristic E of the acoustic field. These points RA and RB are used to obtain point A. Therefore, transmission/reception point A can be accurately obtained irrespective of acoustic field characteristics of tested body 14. Furthermore, in equation (6), parameter Ai(x) may be given as a two-variable function Ai(x, $r_{ix}$), and this function can be experimentally obtained, thereby accurately obtaining transmission/reception beam index point A irrespective of the distance-attenuation characteristics of the ultrasonic beam propagating in tested body 14.

In the above embodiment, the direction of the main beam propagating through tested body 14 is displayed as an image. However, it is possible to determine the direction and start point of the ultrasonic main beam by changing the intensities of transmitted waves from the transducers and the amplitudes of ultrasonic echo signals. In this case, the start point of the main beam to be transmitted can be fixed, and at the same time, transmission/reception of the ultrasonic beam can be performed in a desired direction with high precision. For this purpose, a circuit may be used wherein a transmitted pulse voltage and a received wave amplitude are controlled for each transducer.

In the above embodiment, the reception signal waveform of the ultrasonic beams is converted by a high-speed A/D converter to digital signals. The resultant digital signals are added. However, addition may be performed in an analog form, using a CCD (charge-coupled device), a delay line or the like.

The operation of the apparatus after steered angle $\phi$ of the ultrasonic main beam and point A are determined will now be described.

FIG. 24 is a flow chart for explaining the steps of evaluating the flaw dimensions. FIG. 25 shows propagation directions of ultrasonic main beam 12M when tested body 14 with no flaw is tested in accordance with the flow chart of FIG. 24. First, steered angle $\alpha i$ of transmission probe 10T is preset. More particularly, let parameter i be 1 (ST10 in FIG. 24), and transmission angle $\alpha 1$ is set (ST12). Subsequently, steered angle $\beta j$ of reception probe 10R is set; let parameter j be 1 (ST14), and reception angle $\beta 1$ is set (ST16). Data $\beta 1$ is temporarily registered as angles $\beta m$ for Pmax and Tmin (ST18). Data of angle $\beta m$ is stored in RAM 450 (FIG. 12). Reception echo amplitude P1 is detected when transmission and reception angles are given as $\alpha 1$ and $\beta 1$ (ST20). Amplitude P1 is latched as virtual maximum amplitude Pmax by latch 676 in FIG. 18 (ST22). It is then determined whether or not P1>Pmax (ST24). Since Pmax=P1 is given, the answer is determined to be NO in ST24.

While steps ST20 to ST24 are being executed, the following step is executed. Beam propagation path length T1 is detected at transmission and reception angles $\alpha 1$ and $\beta 1$ (ST30). Note that beam propagation path length T1 is obtained from count output signal CE from counter 556 (FIG. 16). Data T1 is stored as minimum propagation path length Tmin by latch 672 in FIG. 18 (ST32). Subsequently, comparator 674 determines whether or not T1<Tmin (ST34). Tmin=T1 is established, so this inequality is not satisfied (NO in ST34). Thus, NO is derived in steps ST24 and ST34; data P1, T1 and $\beta 1$ are then stored as data Pmax, Tmin and $\beta m$ in latches 676 and 672 and RAM 450 (ST 40), respectively.

It is then determined whether or not reception scanning or $\beta$ scanning is completed (ST42). This is performed by computer 446 (FIG. 12) in accordance with output E616 from coincidence sensor 616 (FIG. 17) so as to determine whether or not parameter j is equal to specified maximum value q. In fact, j=1≠q (NO in ST 42), so that parameter j is incremented by one (ST44). Thus, j=2 is given, so $\beta j=\beta 2$ is set (ST46). Subsequently, amplitude P2 at angles $\alpha 1$ and $\alpha 2$ is detected (ST48), and at the same time beam propagation path length T2 is detected (ST50). Data P2 is compared with data Pmax (ST24). In fact, Pmax is equal to P1. If P2>P1 (YES is ST24), P2 is latched as Pmax by latch 676 of FIG. 18 (ST26). Furthermore, data T2 is compared with data Tmin (ST34). If T2<T1 (YES in ST34), data T2 is latched as Tmin by latch 672 of FIG. 18 (ST36). Data $\beta 2$ is stored as $\beta m$ in RAM 450 of FIG. 12 (ST28). Moreover, in this case, a different Pmax, Tmin and $\beta m$ are stored (ST40) than in the case where j=1 is given.

In fact, if j=2≠q (NO in ST42), parameter j is incremented to 3 (ST44), and $\beta 3$ is set (ST46). Amplitude P3 and path length T3 at angles $\alpha 1$ and $\beta 3$ are detected (ST48 and ST50). If P3>Pmax (=P2) (YES in ST24), data P3 is latched as Pmax by latch 676 (ST26). Furthermore, if T3<Tmin (=T2) (YES in ST34), data T3 is latched as Tmin by latch 672 (ST36). Reception angle $\beta 3$ for data P3 and T3 is stored as $\beta m$ (ST28). When P3<Pmax (NO in ST24) and T3>Tmin (NO in ST34), data Pmax, Tmin and $\beta m$ do not change from the values for j=2. In other words, when YES is determined in steps ST24 and ST34, data P3, T3 and $\beta 3$ are stored as Pmax, Tmin and $\beta m$, respectively (ST40). However, when NO is determined in steps ST24 and ST34, data P2, T2, and $\beta 2$ are stored as Pmax, Tmin and $\beta m$, respectively (ST40).

The above operation (loop of steps ST20 to ST50) is repeated until j=q is established. When j=q (YES is ST42), data Pmax, Tmin and $\beta m$ stored in ST40 up to this moment are registered as regular Pmax, Tmin and $\beta m$ in RAM 450 of FIG. 12 (ST52).

It is then determined whether or not transmission scanning or $\alpha$ scanning is completed (ST52). This is performed by computer 446 (FIG. 12) in accordance with output E614 from coincidence sensor 614 (FIG. 17) so as to determine whether or not the specified parameter i is equal to the maximum value p. In this case, i=1≠p (NO in ST54), so that parameter i is incremented by one (ST56). Thus, i=2, and $\alpha i=\alpha 2$ is set (ST12). Subsequently, let j be 1 (ST14) and $\beta i=\beta 1$ is set (ST16). This $\beta 1$ is temporarily registered as $\beta m$ (ST18).

Subsequently, the same operation (loop of steps ST20 to ST50) as in $\alpha i=\alpha 1$ is repeated for j=1 to q. When j=q is established, the latest updated data Pmax, Tmin and $\beta m$ are stored as regular Pmax, Tmin and $\beta m$ in RAM 450 (ST52).

The same operation (loop of steps ST12 to ST56) for angles $\alpha 1$ and $\alpha 2$ is repeated until i=p is established. When i=p (YES in ST54), the flow of FIG. 24 is ended. In this condition, RAM 450 (FIG. 12) stores miximum amplitudes Pmax, minimum beam propagation path lengths Tmin and reception angles $\beta m$ for Pmax and Tmin of a range of transmission angles $\alpha 1$ to $\alpha p$. The obtained data Pmax, Tmin and $\beta m$ are plotted using $\alpha i$ as a parameter, as shown in FIGS. 26 and 27.

FIG. 26 shows changes in maximum amplitude Pmax for every $\alpha i$ as a parameter and changes in reception angle $\beta m$ in accordance with Pmax for each $\alpha i$ as a parameter when tested body 14 in FIG. 25 is tested. FIG. 27 shows changes in minimum beam propagation path length Tmin for every $\alpha i$ as a parameter and changes in reception angle $\beta m$ obtained from Tmin for every $\beta i$ when tested body 14 in FIG. 25 is tested. Referring to FIGS. 26 and 27, and $\alpha i$ changes, Pmax indicates the maximal value Pm0 and Tmin indicates the minimal value Tm0. Values Pm0 and Tm0 are obtained when the transmission angle is $\alpha 0$. In this condition, the reception angle is $\beta 0$. The angles $\alpha 0$ and $\beta 0$ (corresponding to $\alpha_T$ and $\beta_T$, respectively) can be utilized as data for evaluating the dimensions of an internal flaw of the tested body, together with other known data.

The graphs shown in FIGS. 26 and 27 are displayed at CRT display 716 and/or recorded by X-Y recorder 718.

Figure 28:
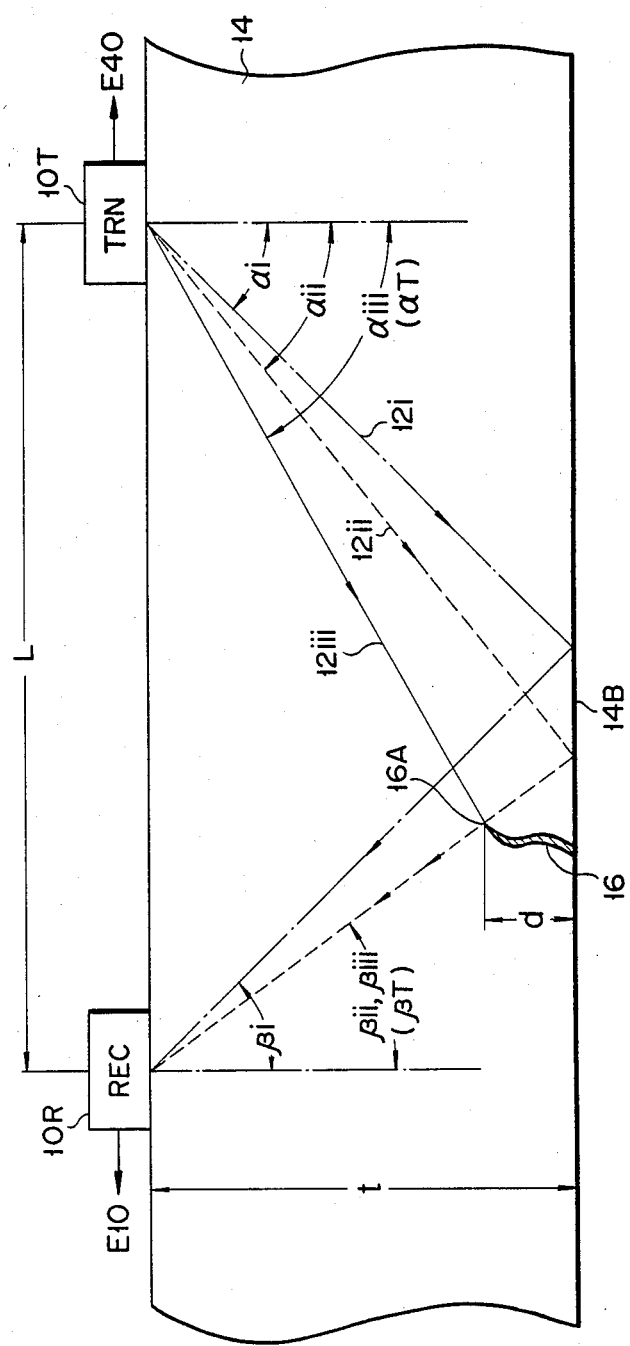
FIG. 28 shows propagation of ultrasonic main beams 12i to 12iii when tested body 14 (FIG. 25) has flaw portion 16.
Figure 29:
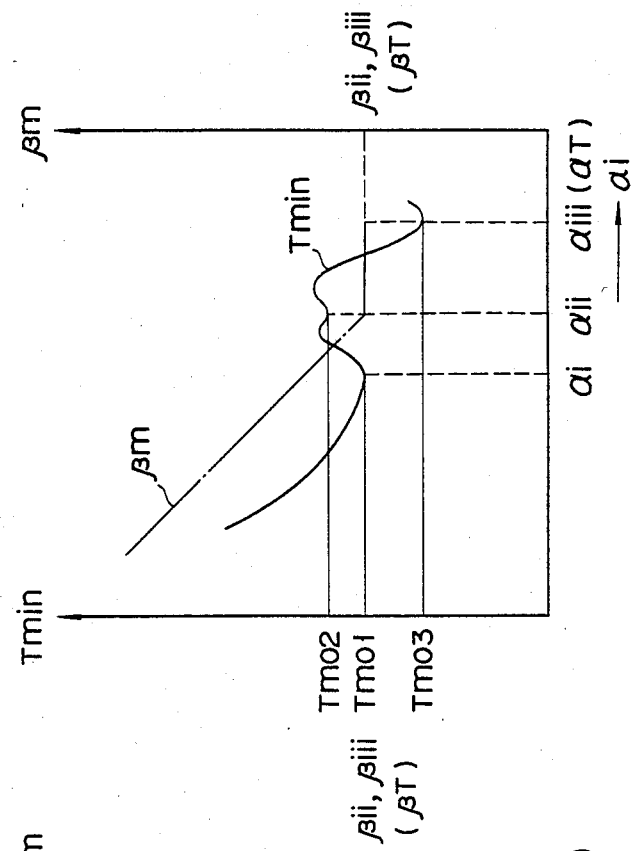
FIG. 29 is a graph showing a relationship among data Pmax, $\beta$m, and $\alpha$i obtained when tested body 14 (FIG. 28) is tested in accordance with the flow chart in FIG. 24.
Figure 30:
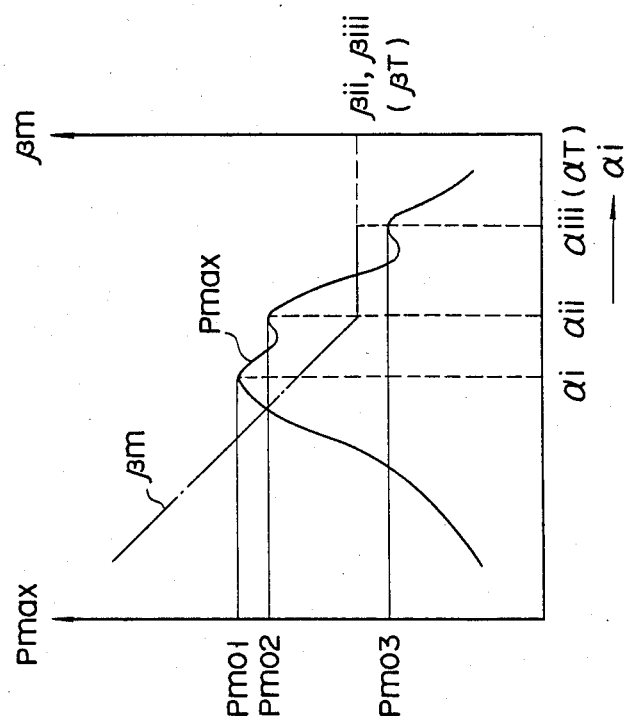
FIG. 30 is a graph showing a relationship among data Tmin, $\beta$m and $\alpha$i obtained when tested body 14 (FIG. 28) is tested in accordance with the flow chart in FIG. 24.

FIG. 28 shows propagation of ultrasonic main beams 12*i*, 12*ii* and 12*iii* when tested body 14 with flaw portion 16 is tested. FIG. 29 shows $\alpha i$ vs Pmax and $\alpha i$ vs $\beta m$ characteristics when tested body 14 shown in FIG. 28 is tested. FIG. 30 shows $\alpha i$ vs Tmin and $\alpha i$ vs $\beta m$ characteristics when the above-mentioned tested body 14 is tested. When flaw portion 16 shown in FIG. 28 is present, three maximal points Pm01 to Pm03 occur corresponding to changes in maximum amplitude Pmax obtained in accordance with the flow chart of FIG. 24 (FIG. 29). Similarly, three minimal points Tm01 to Tm03 occur corresponding to changes in minimum beam propagation path length Tmin (FIG. 30).

The first maximal point Pm01 and the first minimal point Tm01 occur in ultrasonic main beam 12*i* at transmission and reception angles $\alpha i$ and $\beta i$. These maximal and minimal points Pm01 and Tm01 correspond to Pm0 in FIG. 26 and Tm0 in FIG. 27, respectively. The second maximal point Pm02 and the second minimal point Tm02 occur in main beam 12*ii* (at $\alpha ii$ and $\beta ii$). Maximal value Pm02 occurs at transmission angle $\alpha ii$ and reception angle $\beta ii$ when both a diffraction component of main beam 12*ii* at tip 16A of flaw portion 16 and a directly reflected component of main beam 12*ii* reflected at bottom 14B of tested body 14 are incident in a direction at angle $\beta ii$. The third maximal point Pm03 and the third minimal point Tm03 occur in main beam 12*iii* (at $\alpha iii$ and $\beta iii$) when main beam 12*iii* is diffracted at tip 16A of flaw portion 16. In order to obtain dimension d of flaw portion 16, transmission angle $\alpha iii$ and reception angle $\beta iii$ of main beam 12*iii* diffracted at tip 16A must be detected.

The correspondence between a target main beam 12*iii* and data among a plurality of maximal values Pm01 to Pm03 and/or a plurality of minimal values Tm01 to Tm03 is determined as follows.

As may be apparent from FIG. 28, reception angles $\beta ii$ and $\beta iii$ are kept to give a predetermined value $\beta_T$ for every transmission angle $\alpha$ falling within a range between angles $\alpha ii$ and $\alpha iii$. This is indicated by a horizontal portion of $\beta m$ curve in FIG. 29 or 30. When $\alpha j$ does not change even as $\alpha i$ is increased, the target main beam 12*iii* can be obtained by transmitted angle $\alpha iii$ indicating the first detected maximal value Pm03 of Pmax or the first detected minimal value Tm03 of Tmin. Transmission angle $\alpha iii$ and reception angle $\beta iii$ of this main beam 12*iii* become $\alpha_T$ and $\beta_T$ used for evaluaton of flaw dimension d.

Figure 31:
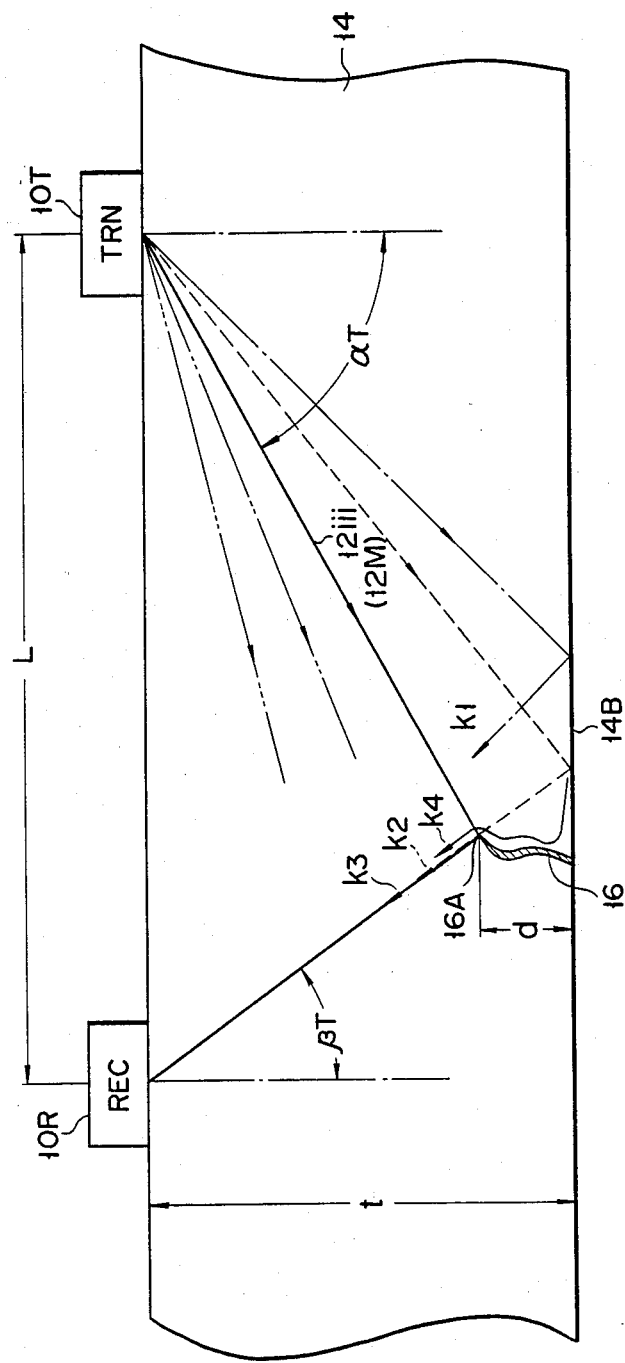
FIG. 31 shows main propagation paths k1 to k4 of ultrasonic main beam 12iii (FIG. 28)

FIG. 31 shows main propagation paths among the possible propagation paths of ultrasonic main beam 12*iii*. Main beam 12*iii* is illustrated as a single line in FIG. 28 for illustrative convenience. However, in fact, beams 12*iii* spread while they propagate in the direction of flaw portion 16. Main beam 12*iii* indicates the highest intensity stream. Therefore, even when angle $\alpha i$ is fixed at $\alpha_T$, there exist many reflected/scattered waves directed toward reception probe 10R. Among these reflected/scattered waves, the major wave passes through the following four propagation paths k1 to k4: path k1 along which the wave is reflected by bottom surface 14B of tested body 14 and directed toward probe 10R; path k2 along which the wave is reflected by bottom surface 14B, scattered at tip 16A of flaw portion 16, and directed toward probe 10R; path k3 along which the wave is scattered by tip 16A and directed toward probe 10R; and path k4 along which the wave is subjected to wave mode transformation at bottom surface 14B, and this wave reaches tip 16A as a surface wave and is directed as a scattered wave toward probe 10R. In this manner, there exist a plurality of propagation paths for the single main beam 12*iii*, so that several peaks appear in an A-scope display image of ultrasonic echoes received by probe 10R.

Figure 32:
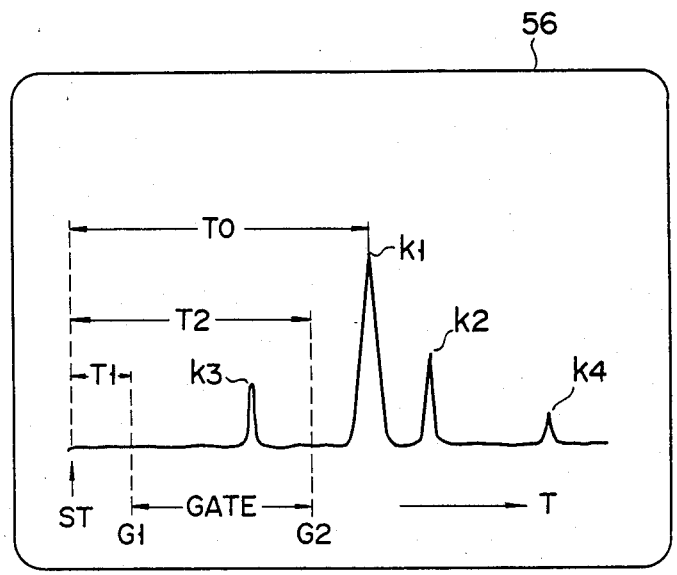
FIG. 32 shows an A-scope displayed image including a plurality of peaks of ultrasonic echoes generated corresponding to propagation paths k1 to k4 shown in FIG. 31.
Figure 33:
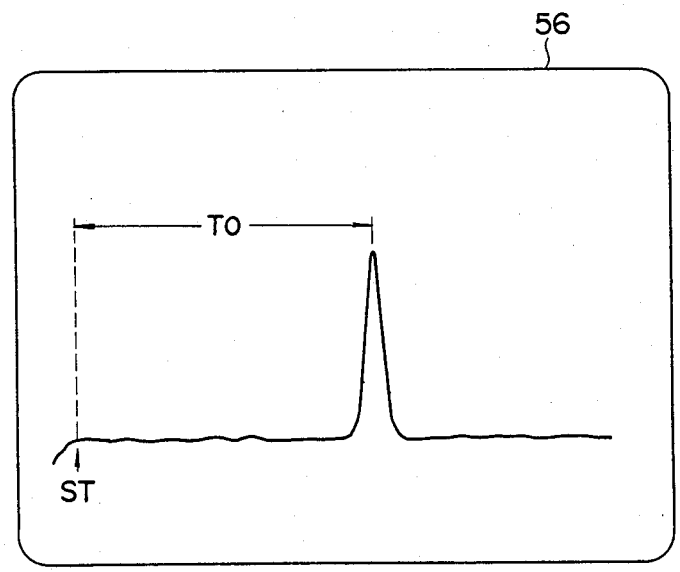
FIG. 33 shows an A-scope display image obtained when tested body 14 having no flaw is tested.

FIG. 32 shows an A-scope display image including peaks of ultrasonic echoes caused by four paths k1 to k4. According to the present invention, only the echo component of path k3 is required, so that echo components in paths k1, k2 and k4 are not necessary. In order to extract only the echo component in path k3, a gate may be set on the beam propagation paths. More particularly, a gate range of T1 to T2 is set within a range of path length T0 from sweep start point ST of the A-scope display to a point at which a peak corresponding to path k1 occurs (FIG. 32). Start point ST can be obtained from count output CE when counter 556 (FIG. 16) is cleared. Path length T0 corresponding to path k1 is obtained from count output CE when a single peak (FIG. 33) occurs. Note that this single peak occurs when a portion having no flaw portion 16 is scanned with the ultrasonic wave at transmission angle $\alpha_T$. Gate start and end point T1 and T2 are given by data G1 and G2 from decoders 640 and 642 in FIG. 17, respectively. Among ultrasonic echoes detected within the gate range, only high amplitude components exceeding a predetermined noise level are used for detection of data Pmax and Tmin. This detection is performed by circuit elements 660 to 670 in FIG. 18.

Maximal amplitude value Pm03 and minimal beam propagation path length Tm03 which correspond to path k3 within gate range T1 to T2 are detected. During this detection, transmission angle $\alpha_T$ and reception angle $\beta_T$ are obtained to evaluate flaw dimension d.

When the thickness of tested body 14 is given as t and the distance between the transmission and reception beam index points is given as L, and data $\alpha_T$ and $\beta_T$ and the corresponding Tm0 ($=$Tm03) are determined, then dimension d of flaw portion 16 can be given by one of equations (7), (8) and (9):

$$d = t - L/(\tan\alpha_T + \tan\beta_T) \qquad (7)$$

$$d = t - \{(Tm0^2 - L^2)/2(Tm0 - L\sin\alpha_T)\}\cos\alpha_T \qquad (8)$$

$$d = t - \{(Tm0^2 - )/2(Tm0 - L\sin\beta_T)\}\cos\beta_T \qquad (9)$$

The obtained dimension d is displayed on displlay panel 736 in FIG. 20. Note that equations (7) to (9) are applied when the sonic velocity in tested body 14 is constant. However, even if the sonic velocity in test body 14 changes, flaw dimension d can be evaluated if changes in sonic velocity are known beforehand.

Operations according to equations (7) to (9) are automatically performed by ALU 702 in accordance with a command from computer 692 in FIG. 19. When variables in equations (7) to (9) are given, a conventional external computer may be used.

Figure 35:
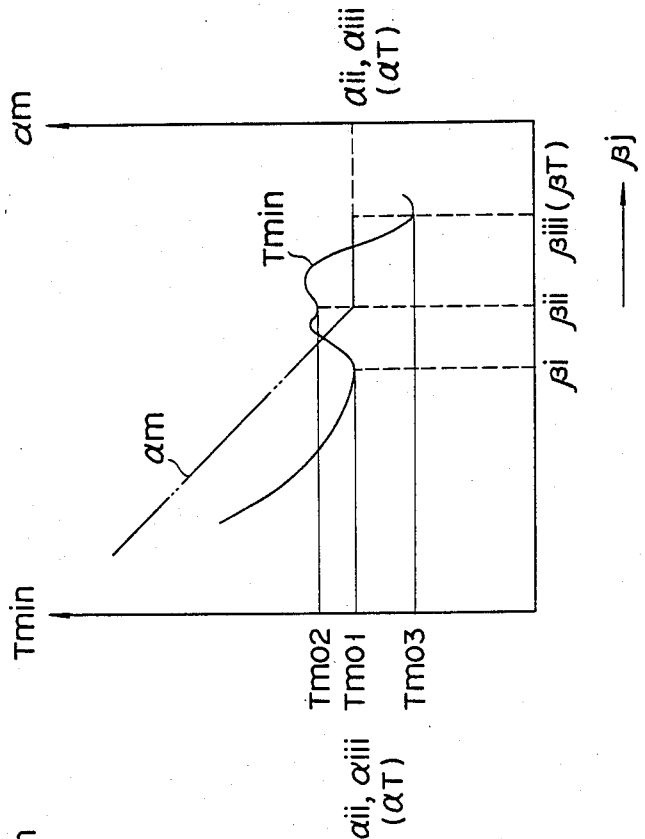
FIG. 35 is a graph for explaining a relationship among data Tmin, $\alpha$m and $\beta$j obtained when parameters $\alpha$ and i are replaced with parameters $\beta$ and j in the flow chart shown in FIG. 24.
Figure 34:
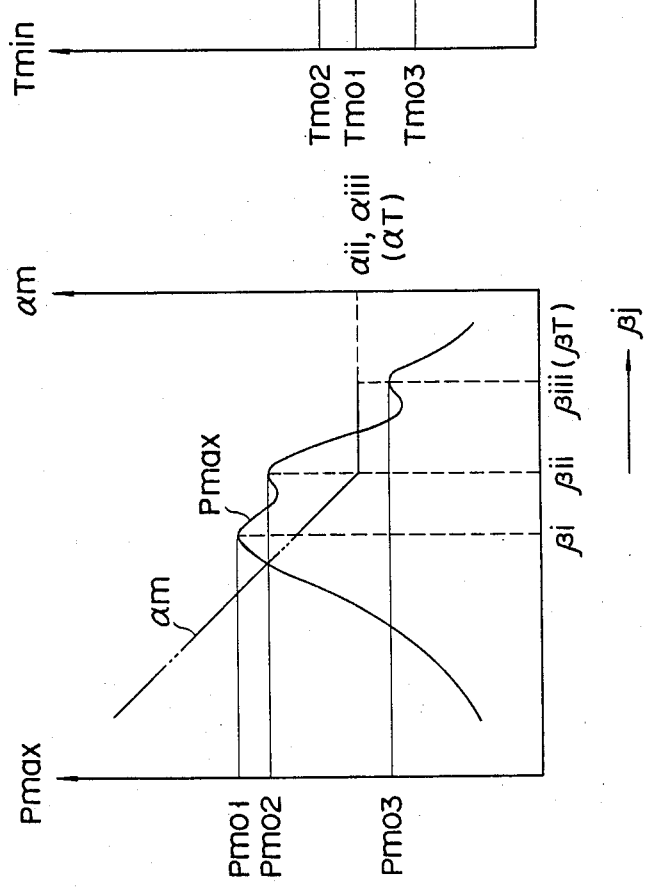
FIG. 34 is a graph for explaining a relationship among data Pmax, $\alpha$m and $\beta$j obtained when parameters $\alpha$ and i are replaced with parameters $\beta$ and j in the flow chart shown in FIG. 24.
Figure 36:
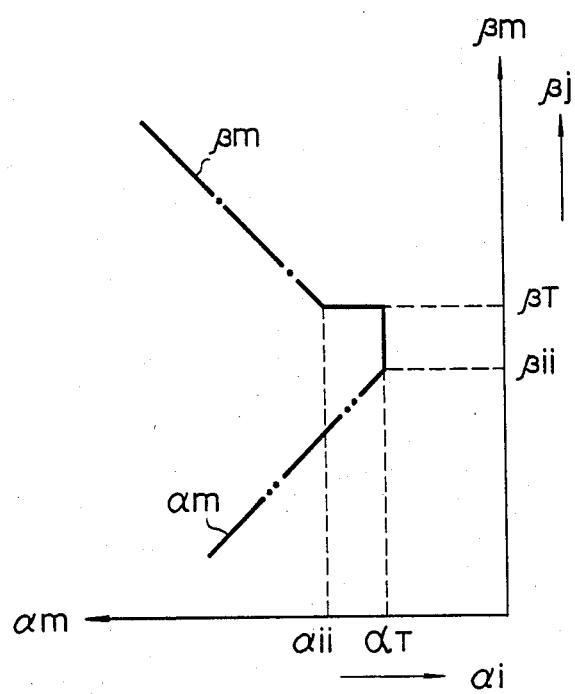
FIG. 36 is a graph for explaining a procedure for obtaining $\beta_T$ and $\alpha_T$ from an intersection between a horizontal portion of a curve of $\beta$m when $\alpha$i is given as a variable and a horizontal portion (vertical portion in FIG. 36) of a curve of αm when βj is given as a variable.

In the above description, angle $\beta m$ is obtained by scanning at reception angle $\beta j$ for every transmission angle $\alpha i$. However, scanning at transmission angle $\alpha i$ may be performed for every reception angle $\beta j$ so as to obtain $\alpha m$ for Pmax or Tmin. In this case, results shown in FIGS. 34 and 35 can be obtained in the same manner as those in FIGS. 29 and 30. Furthermore, the horisontal portions of the curves respectively indicating $\alpha m$ and $\beta m$ may be obtained, and data $\beta_T$ and $\alpha_T$ may be obtained from an intersection between these horizontal portions (FIG. 36). In this case, detection precision of $\beta_T$ and $\alpha_T$ is higher than that in FIGS. 29 and 30 or FIGS. 34 and 35.

Data $\beta_T$ and $\alpha_T$ used in equations (7) to (9) need not be data corresponding exactly to Pm03 and Tm03. More particularly, $\beta m$ (or $\alpha m$) obtained near Pm03 and/or Tm03 and the corresponding $\alpha i$ (or $\beta j$) may be respectively used as $\beta_T$ and $\alpha_T$ so as to evaluate flaw dimension d from one of equations (7) to (9). A plurality of gates may be formed along beam propagation path length T. This is very effective in accurately obtaining each flaw dimension when a plurality of flaw portions exist in tested body 14. Conversely, a plurality of flaw echoes may be detected by a single gate so as to obtain $\alpha_T$ and $\beta_T$ for every flaw echo.

Another method for evaluating flaw dimension d will be described in detail hereinafter.

Figure 38:
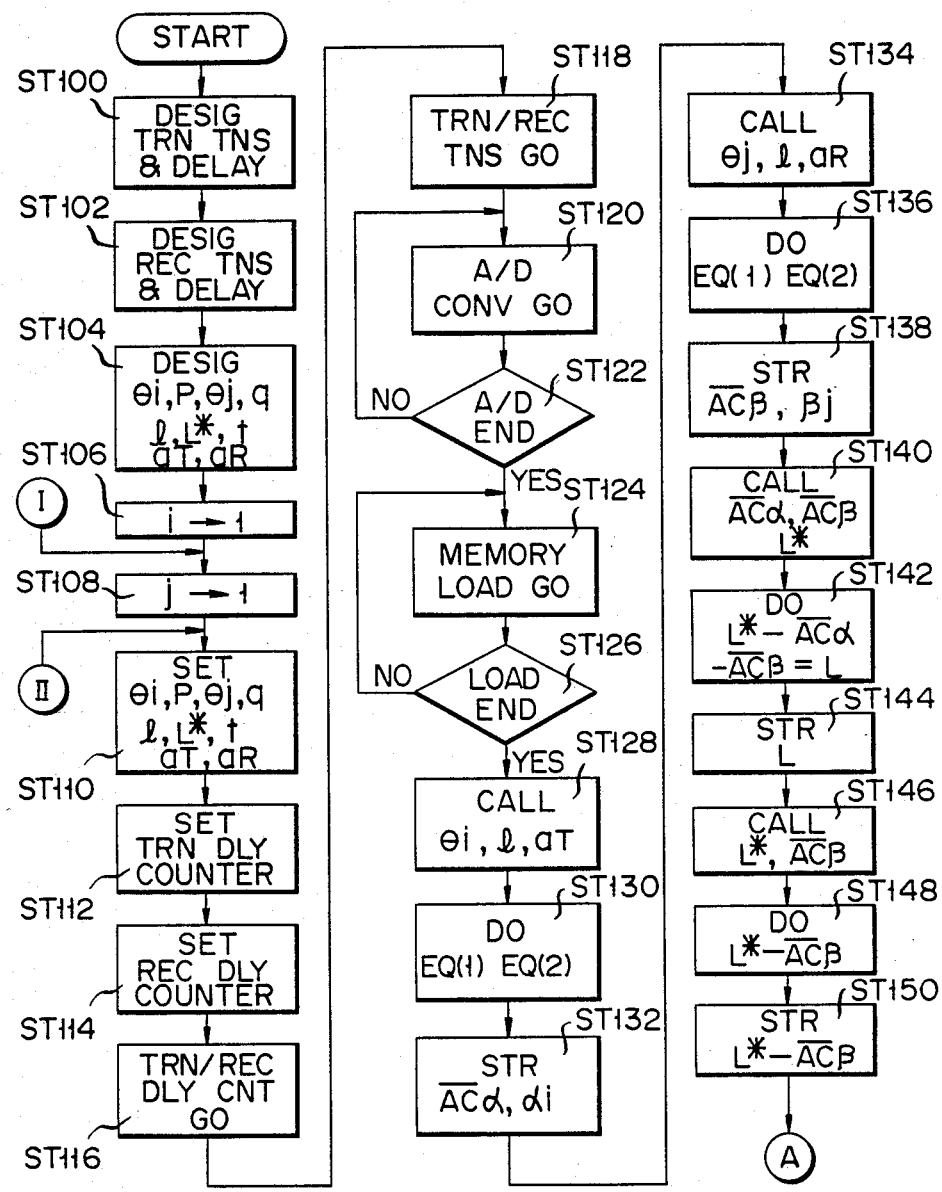
FIGS. 38 to 40 are flow charts for explaining the steps of evaluating flaw dimension d according to the configuration shown in FIG. 37.
Figure 39:
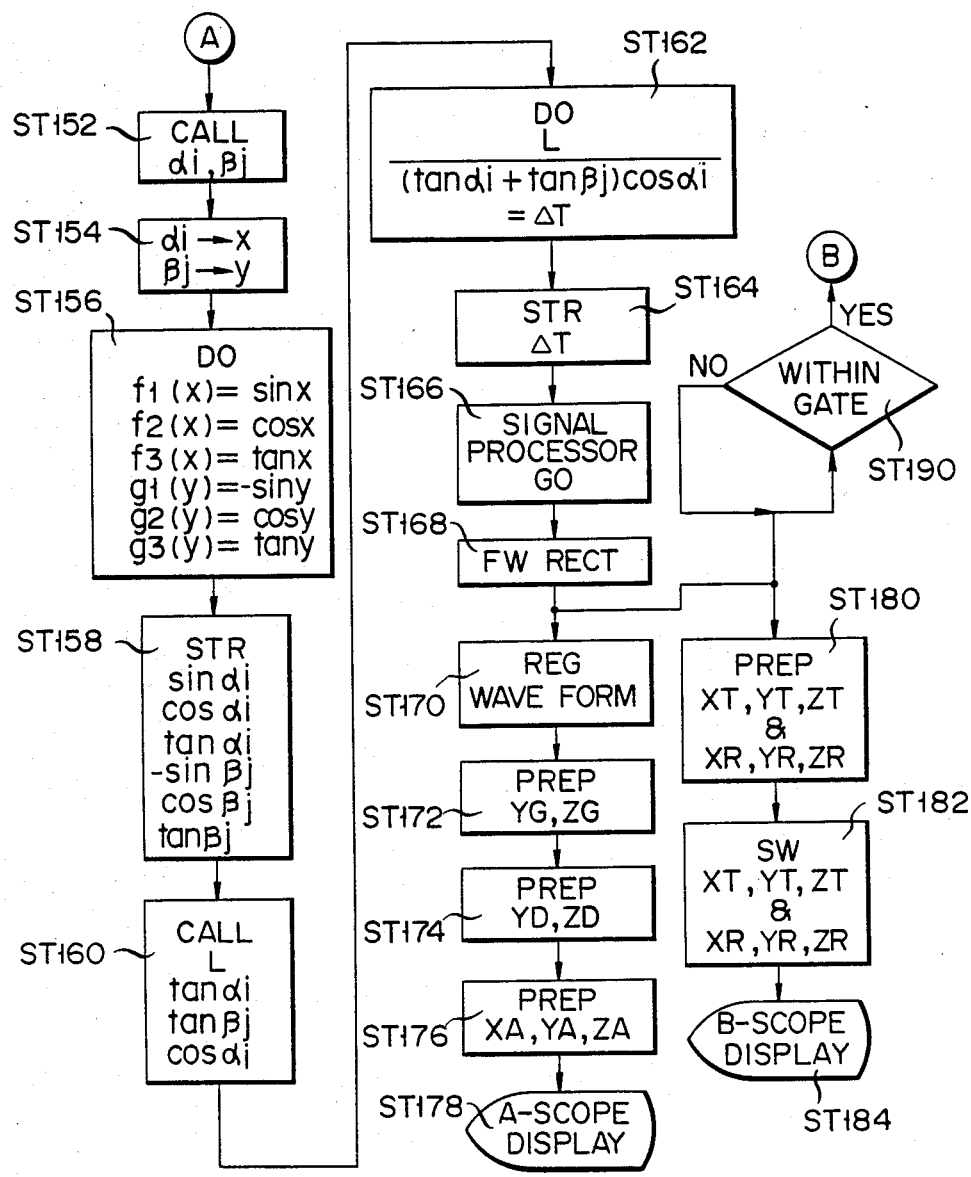
Figure 40:
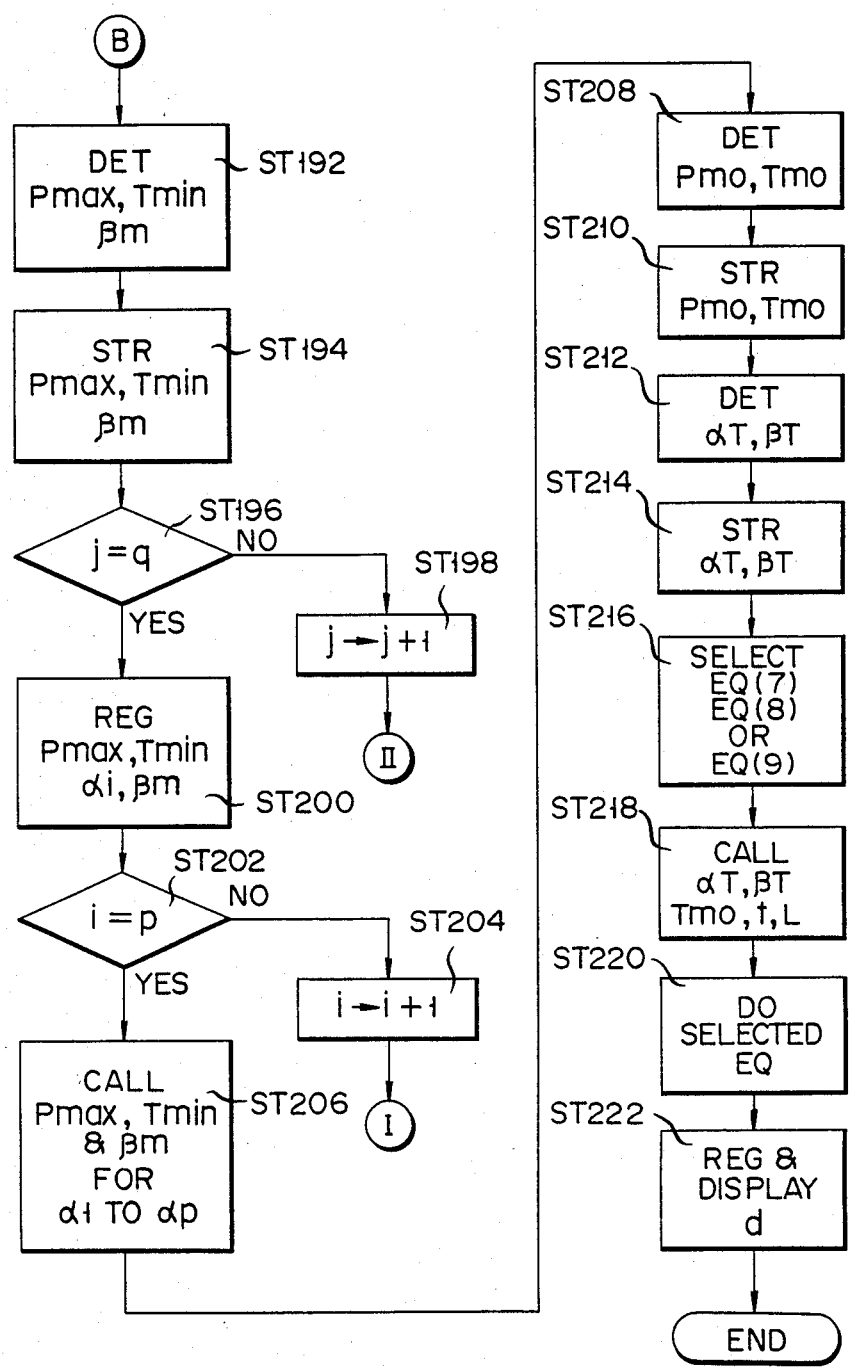

FIG. 37 shows a state wherein ultrasonic main beam 12M transmitted from transmission probe 10T is diffracted or scattered at flwa tip 16A and a diffraction beam is incident on reception probe 10R. FIGS. 38 to 40 are flow charts for explaining the steps of evaluating flaw dimension d by means of the configuration shown in FIG. 37.

In the first place, a combination of transducers among transmission tranducers 10T shown in FIG. 37 is designated (ST100 in FIG. 38). This can be performed by designating preset data for presettable counters $420_1$ to $420_n$ and latch data for latch 428 (FIG. 11). Then, a combination of transducers among reception transducers 10R shown in FIG. 37 is designated (ST102). This can be performed by designating preset data for presettable counters $500_1$ to $500_n$ and latch data for latch 508 (FIG. 13). Subsequently, the following data must be designated: steered or transmission angle $\theta i$ with respect to central point CT of transmission transducers (also referred to as transmission probe or simply probe) 10T; maximum value p of parameter i of transmission angle $\theta i$; reception angle $\theta j$ with respect to central point CR of reception probe 10R; maximum value q of parameter j of steered or reception angle $\theta j$; convergence path length l; distance L* between central points CT and CR; thickness t of tested body 14; aperture size aT of probe 10T; and aperture size aR of probe 10R (ST104). Aperture size aT is determined by a product of the number of selected transmission transducers and a pitch of a transducer array of probe 10T. Similarly, aperture size aR is determined by a product of the number of selected reception transducers and a pitch of a transducer array of probe 10R. All the data designated in step ST104 are regarded as known data hereinafter.

Paramter i is set to be 1 (ST106), and parameter j is set to be 1 (ST108). Subsequently, data designated in steps ST104 to ST108 (i.e., $\theta i = \theta 1$, p, $\theta j = \theta 1$, q, l, L* t, aT and aR) are stored in RAM 450 shown in FIG. 12 (ST110). Computer 446 shown in FIG. 12 presets predetermined transmission data in counters $420_1$ to $420_n$ and latch 428 shown in FIG. 11 (ST112). Computer 446 then presets predetermined reception data in counters $500_1$ to $500_n$ and latch 508 shown in FIG. 13 (ST114). The number of transducers V1 to Vn defining the effective aperture size aT and their order of excitation are designated in step ST112. Similarly, the number of transducers V1 to Vn defining the effective aperture size aR and their order of excitation are designated in step ST114. When transmission and reception delay cotrollers 42 and 50 are set in steps ST112 and ST114, respectively, computer 446 (FIG. 12) start the counters of controllers 42 and 50 (ST116).

When the counters of controller 42 are started, an ultrasonic wave is transmitted from probe 10T in direction $\theta i$ ($= \theta 1$), and probe 10R receives the transmitted ultrasonic wave along the same direction (ST118). The ultrasonic echo received by probe 10R becomes reception echo signals E10. These echo signals are supplied to ultrasonic receiver 46 (FIG. 10). Analog reception signals E46 amplified by receiver 46 are supplied to A/D converter 48 (FIG. 14). Converter 48 performs A/D conversion in accordance with trigger signals E50 from reception delay counter 50 (ST120). Subsequently, it is determined whether or not A/D conversion is completed (ST122). This can be performed in accordance with logic level of output S48 from AND gate 484 in FIG. 14. While S48="0" (NO in ST122), A/D conversion continues in step ST120. However, when signal S48 goes high (i.e., S48="1" or YES in ST122), A/D conversion is completed.

When S48="1", clock oscillator 486 in FIG. 14 starts oscillation. Clock pulse CKC is supplied to address counter 524 in FIG. 15. A/D-converted outputs $E48_1$ to $E48_n$ from converter 48 in FIG. 14 are added by adder 520 (FIG. 15) to each other. Clock pulse CKC clocks counter 524 so that output E520 from adder 520 is loaded in RWM 522 (ST124). The end of data storage is determined when counter 524 generates count-up pulse ENA. However, when pulse ENA is not generated (NO in ST126), storage operation of RWM 522 continues. When pulse ENA is generated, oscillator 486 in FIG. 14 stops oscillation. When pulse ENA is fetched in computer 446 in FIG. 12, computer 446 supplies reset pulse RSA to counter 524 in FIG. 15 so as to clear counter 524. Thus, data storage operation of RWM 522 is completed (YES in ST126).

After computer 446 in FIG. 12 supplies reset pulse RSA to counter 524 in FIG. 15, computer 446 calls data $\theta i = \theta 1$, l, and aT ($=a$) stored in RAM 450 (ST128). These data are fetched in slave computer 692 through latches $456_1$ to $456_n$ (FIG. 12) and IN port 694 (FIG. 19). A program for solving equations (1) and (2) is preloaded in RAM 700 (FIG. 19). When computer 692 receives data $\theta i$, l and aT, computer 692 allows ALU 702 to substitute these data in equatons (1) and (2) (ST130). The program for equations (1) and (2) can be readily programmed using FORTRAN or BASIC, details thereof will be omitted. Transmission angle $\alpha l$ ($=\phi$) of FIG. 37 is obtained by equation (1), and distance $\overline{AC_\alpha}$ between points AT and CT is obtained by equation (2). Obtained data $\overline{AC_\alpha}$, $\alpha l$ are stored in RAM 700 shown in FIG. 19 (ST132).

When data $\overline{AC_\alpha}$ and $\alpha 1$ are stored, computer 446 calls data $\theta j = \theta 1$, l and aR ($=a$) from RAM 450 (ST134). These data are supplied to computer 692 through latches $456_1$ to $456_n$ and IN ports 694. Computer 692 causes ALU 702 to substitute data $\eta j$, l, and aR in equations (1) and (2) (ST136). By this operation, distance $\overline{AC_\beta}$ and reception angle $\beta 1$ shown in FIG. 37 are obtained. Obtained data $\overline{AC_\beta}$ and $\beta 1$ are stored in RAM 700 shown in FIG. 19 (ST138).

Subsequently, data $\overline{AC_\beta}$ and $\overline{AC_\beta}$ are read out from RAM 700 (FIG. 19), and data L* is read out from RAM 450 (FIG. 12). Computer 692 of FIG. 19 performs the following operation to calculate distance L between actual transmission and reception beam index points AT and AR (ST142):

$$L = L^* - \overline{AC}_\alpha - \overline{AC}_\beta \qquad (10)$$

Obtained data L is stored in RAM 700 under the control of computer 692 (ST144). Data L* is read out from RAM 450, and data $\overline{AC}_\beta$ is read out from RAM 700 (ST146). Computer 692 performs the following operation (ST148):

$$L^* - \overline{AC}_\beta \qquad (11)$$

By the above operation, data $(L^* - \overline{AC}_\beta)$ for determining the sweep start point for B-scope display is obtained. This data $(L^* - \overline{AC}_\beta)$ is stored in RAM 700 (ST150).

Data indicating transmission and reception angles $\alpha 1$ and $\beta 1$ are read out from RAM 700 shown in FIG. 19 (ST152 in FIG. 39). These data $\alpha 1$ and $\beta 1$ are registered as variables x and y (ST154). Subsequently, six trigonometric functions are operated as follows (ST156): $f_1(x) = \sin x$, $f_2(x) = \cos x$, $f_3(x)$ $\tan x$, $g_1(y) = -\sin y$, $g_2(y) = \cos y$ and $g_3(y) = \tan y$. These operations are performed by ALU 702, and operation results are stored in RAM 700 (ST158). Data L, tan 1, tan$\beta 1$ and cos$\alpha 1$ are read out from RAM 700 (ST160). Beam propagation path length $\Delta T$ from transmission beam index point AT to focal point F at angles $\alpha(=\alpha 1)$ and $\beta j$ $(=\beta 1)$ is calculated by the following equation (ST162):

$$\Delta T = L / (\tan\alpha i + \tan\beta j) \cos\alpha i \qquad (12)$$

The above operation is performed by ALU 702 shown in FIG. 19. Obtained path length data $\Delta T$ is stored in RAM 700 (ST164). Thereafter, computer 446 shown in FIG. 12 supplies start pulse STX to oscillator 540 shown in FIG. 16. Oscillator 540 then starts oscillation, and clock pulse CKA is supplied to counter 524 in FIG. 15. Composite reception signal E52 or waveform data of digital reception echo signals is read out from RAM 522. Note that one-address length of RWM 522 corresponds to a product of one-clock time in A/D conversion by converter 48 and the sonic velocity of the ultrasonic beam in tested body 14. When the readout operation of signal E52 is started, signal processor 54 shown in FIGS. 16 to 19 is started (ST166).

Signal E52 read out from RWM 522 in FIG. 15 is full-wave rectified by rectifier 542 shown in FIG. 16 (ST158). Rectified output WE from rectifier 542 includes waveform data of the ultrasonic echoes received by probe 10R (FIG. 37). This waveform data (WE) is stored in RWM 602 shown in FIG. 17 (ST170). Subsequently, intensity signal ZG is prepared within an address range of RWM 602 which corresponds to predetermined gate range G1 to G2 (or T1 to T2 in FIG. 32), and Y-signal YG (fixed potential) is prepared (ST172). Signal ZG is formed by circuit elements 646, 648 and 652 (FIG. 17) in response to signals G1, G2 and D634. Signals YG and ZG are used as A-scope gate signals.

Signal YD is prepared from discrimination level DL (ST174). Note that discrimination level DL serves to extract echo signal components exceeding a predetermined noise level from waveform data (WE). Also in step ST174, signal ZD is produced from an address indicating a predetermined intensity start point (or unblanking start point) for a predetermined time interval. Signal YD is the same as signal YD* from D/A converter 554 shown in FIG. 16. Signal ZD is generated from one-shot 654 shown in FIG. 17. Signals YD and ZD are used as A-scope display signals. Subsequently, in step ST176, signal XA is prepared from a read address of RWM 602, and signal YA is prepared from data indicating waveform data (WE) in RWM 602. Also in step ST176, signal ZA is prepared from clock signal E632 of address counter 634 while addresses of RWM 602 are updated. Signal XA is generated by D/A converter 638, signal YA is generated by time constant circuit 606, and signal ZA is generated by one-shot 636 (FIG. 17). Signals XA, YA and ZA are used as A-scope waveform signals. When signals YG, ZG, YD, ZD, XA, YA and ZA are prepared in steps ST172 to ST176, the inside of tested body 14 is A-scope displayed at A-scope display 56 in FIG. 10 (ST178).

While A-scope display is being performed in steps ST170 to ST178, B-scope display is also performed. B-scope display signals XT, YT and ZT respectively corresponding to transmission signals E40 and B-scope display signals XR, YR and ZR respectively corresponding to reception echo signals E10 are prepared (ST180). Signal XT is generated by adder 592 in FIG. 16; signal YT is generated by multiplier 580; and signal ZT is obtained from fixed potential V+. Signal XR is generated by adder 590 shown in FIG. 16; signal YR is generated by multiplier 578; and signal ZR is generated by D/A converter 548. A transmission signal group (XT, YT and ZT) and a reception signal group (XR, YR and ZR) are alternately selected (ST182). The signal groups (XT, YT and ZT) and XR, YR and ZR) are alternately B-scope displayed on the CRT (ST184).

While A-scope display in steps ST170 to ST178 and B-scope display in steps ST180 to ST184 are being performed, it is also determined whether or not address data D634 of RWM 602 (FIG. 17) falls within the predetermined gate range of G1 to G2 (ST190). This can be performed by circuit elements 646, 648 and 652 in FIG. 17. Maximum amplitude Pmax and Minimum propagation path length Tmin of the ultrasonic main beam at transmission angle $\alpha i$ $(=\alpha 1)$ and reception angle $\beta j(=\beta 1)$ are detected. Detected data Pmax and Tmin are stored in latches 676 and 672 in FIG. 18 (ST194).

It is then determined whether or not parameter j of reception angle $\beta j$ is equal to maximum value q (ST196). In fact, $j = 1 < q$ (NO in ST196), so that parameter j is incremented by one (ST198). Thereafter, the flow returns to step ST110 in FIG. 38. In step ST110, the flow including steps ST110 to ST194 is executed for $i = 1$ and $j = 2$, so that data Pmax and Tmin at transmission angle $\alpha i$ $(=\alpha 1)$ and reception angle $\beta j$ $(=\beta 2)$ are obtained and stored (ST194). The flow (steps ST110 to ST194) is repeated until $j = q$. When $j = q$ (YES in ST196), data Pmax and Tmin as well as data $\beta m$ for Pmax and Tmin obtained at trasmission angle $\alpha i$ $(=\alpha 1)$ are registered in RAM (ST200).

It is then determined whether or not parameter i of transmission angle $\alpha i$ is equal to maximum value p (ST202). In fact, $i = 1 < p$ (NO in ST202), so that parameter i is incremented by one (ST204). The flow then returns to step ST108 in FIG. 38. In this step, the flow of steps ST110 to ST194 is performed for $i = 2$ and $j = 1$. Data Pmax and Tmin at transmission angle $\alpha i$ $(=\alpha 2)$ and reception angle $\beta j$ $(=\beta 1)$ are obtained and stored in latches 676 and 672 shown in FIG. 18 (ST194). The flow of steps ST110 to ST194 is repeated until $j = q$. When $j = q$, data Pmax and Tmin as well as data $\beta m$ for Pmax and Tmin obtained at transmission angle $\alpha i$ $(=\alpha 2)$ are stored in RAM 700 (ST200). The flow of steps S108 to ST200 is repeated until $i = p$. When $i = p$ (YES in ST202), data Pmax, Tmin and $\beta m$ for every transmission angle $\alpha 1$ to $\alpha p$ are stored in RAM 700.

Data Pmax, Tmin and $\beta m$ for each of transmission angles $\alpha 1$ to $\alpha p$ are read out from RAM 700 (ST206). These data are supplied to slave computer 692 (FIG. 19). Computer 692 detects the larges Pmax as maximal value PmO among respective data Pmax at transmission angles $\alpha 1$ to $\alpha p$ and smallest Tmin as minimal value Tm0 among respective data Tmin at transmission angles $\alpha 1$ to $\alpha p$ (ST208). Detected data Pm0 and Tm0 are stored in RAM 700 (ST210). Subsequently, transmission angle $\alpha i = \alpha_T$ and reception angle $\beta m = \beta_T$ obtained at the time of calculation of data Pm0 and Tm0 are detected (ST212). Detected data $\alpha_T$ and $\beta_T$ are stored in RAM 700 (ST214).

One of equations (7), (8) and (9) is manually selected (ST216). Data of the selected equation is supplied to computer 692 (FIG. 19). When equation selection is completed, necessary data among data $\alpha_T$, $\beta_T$, Tm0, t and L are read out from RAM 450 (FIG. 12) and RAM 700 (FIG. 19) in step ST218. If equation (7) is selected in step ST216, data t, L, $\alpha_T$ and $\beta_T$ are called in step ST218. However, when equation (8) is selected in step ST216, data t, L, Tm0 and $\alpha_T$ are called; and when equation (9) is selected in step ST216, data t, L, Tmo and $\beta_T$ are called. When equation selection and access of required data are completed, ALU 702 (FIG. 19) executes predetermined operation in accordance with the selected equation. Flaw dimension d obtained by this operation is stored in RAM 700 and is displayed on display panel 736 in FIG. 20 (ST222).

Figure 43:
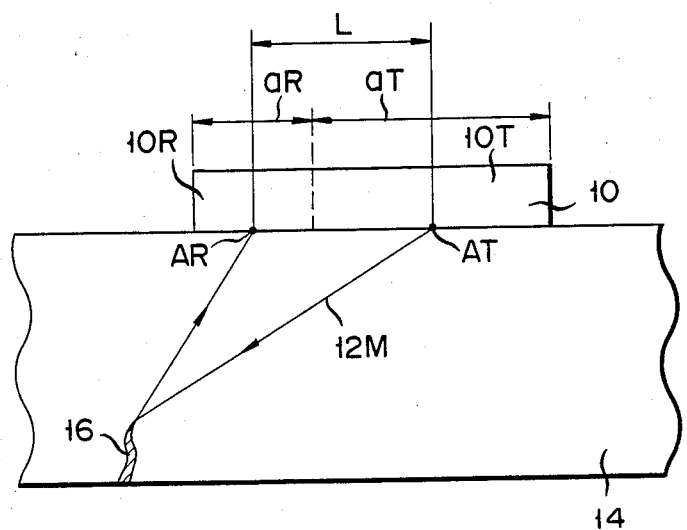
FIG. 43 shows a case wherein single probe 10 is divided into transmission probe 10T of some transmission transducers and reception probe 10R of some reception transducers.
Figure 44:
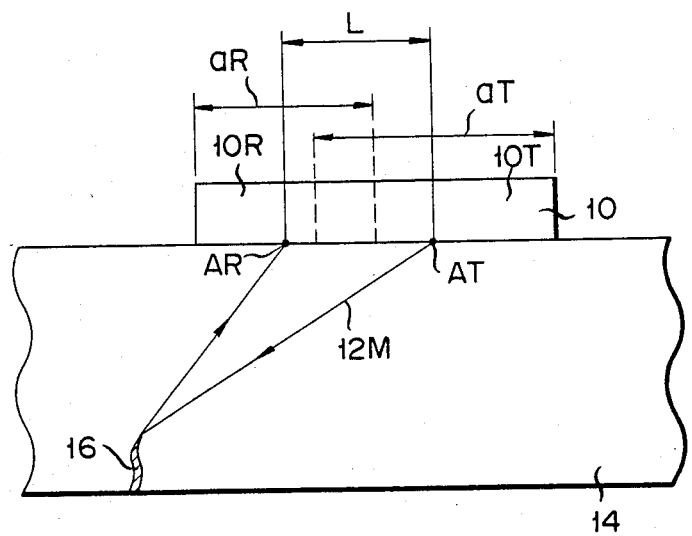
FIG. 44 shows a case where aperture size aT of set 10T overlaps aperture size aR of set 10R when single probe 10 is divided into transmission probe 10T of some transmission transducers and reception probe 10R of some reception transducers.

The value for flaw dimension d obtained by these steps may not have high precision when operation is performed only once. In this case, values are calculated for a plurality of flaw dimensions d in a manner described below so as to obtain a mean value thereof, thereby evaluating flaw dimension d with high precision:

(a) N distances L* (or L) of FIG. 37 are preset to calculate n values of flaw dimension d for each distance L* (or L), and a mean value of n values of flaw dimension d is obtained (cf., FIGS. 45 to 50);

(b) N aperture sizes aT and/or aR of FIG. 37 are preset to calculate n values of flaw dimension d for each aT and/or aR, and a mean value of n values of flaw dimension d is obtained (cf., FIGS. 43 and 44);

(c) Values for flow dimension d respectively obtained by equations (7), (8) and (9) are summed and divided by three to obtain a mean value; and (d) A combination of any of methods (a), (b) and (c) is used to obtain a mean value for flaw dimensions d.

Figure 41:
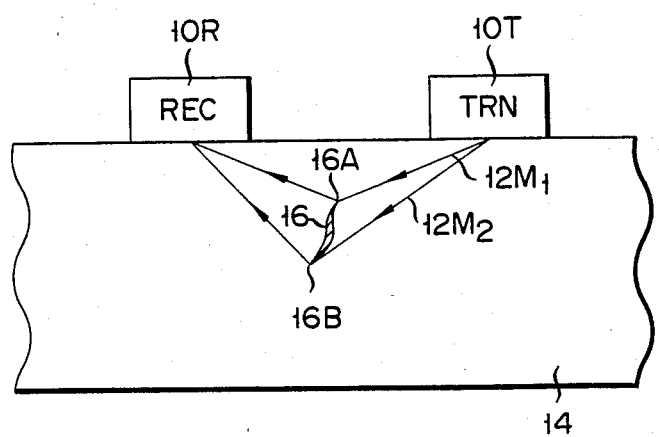
FIG. 41 shows propagation of ultrasonic main beams 12M diffracted by two flaw tips 16A and 16B of flaw portion 16 when flaw portion 16 occurs at a middle portion inside tested body 14.

FIG. 41 shows a case wherein flaw portion 16 occurs at a middle portion inside tested body 14. In this case, the first maximal value Pm01 of data Pmax is obtained by diffraction of main beam $12M_1$ at one tip 16A of flaw portion 16. The second maximal value Pm02 of data Pmax is obtained by diffraction of main beam $12M_2$ at the other tip 16B. The position of tip 16A is determined by data Tm0, $\alpha_T$ and $\beta_T$ in accordance with Pm01. Similarly, the position of tip 16B is determined by data Tm0, $\alpha_T$ and $\beta_T$ in accordance with Pm02. When the positions of tips 16A and 16B are determined, a distance therebetween (i.e., flaw dimension d) is obtained from the following equations (7A) to (9A).

$$d = \{1/(\tan\alpha_{T1}+\tan\beta_{T1}) - 1/\tan\alpha_{T2}+\tan\beta_{T2})\} \tag{7A}$$

$$d = \{\cos\alpha_{T1}/2(Tm0-L\sin\alpha_{T1}) \\ -\cos\alpha_{T2}/2(Tm0-L\sin\alpha_{T2})\} \times (Tm0^2 - L^2) \tag{8A}$$

$$d = \{\cos\beta_{T1}/2(Tm0-L\sin\beta_{T1}) \\ -\cos\beta_{T2}/2(Tm0-L\sin\beta_{T2})\} \times (Tm0^2 - L^2) \tag{9A}$$

The first term within the large bracket of each equation of (7A), (8A) and (9A) is obtained according to main beam $12M_1$ for tip 16A of flaw portion 16, and the second term thereof is obtained according to main beam $12M_2$ for tip 16B of flaw portion 16.

Figure 42:
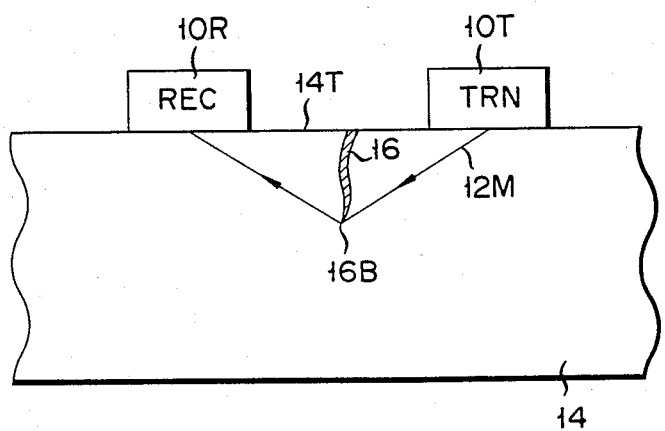
FIG. 42 shows propagation of ultrasonic main beam 12M diffracted by lower flaw tip 16B of flaw portion 16 when flaw portion 16 extends inward from upper surface 14T of tested body 14.

FIG. 42 shows a case wherein flaw portion 16 is formed extending inward from surface 14T In this case, lower tip 16B of flaw portion 16 is detected in the same manner as upper tip 16A of FIG. 37. Flaw dimension d can be evaluated in accordance with detection results.

Dimension d of FIG. 42 can be obtained by deleting the term "t" from equations (7) to (9). Namely, flaw dimension d is represented as:

$$d = L/(\tan\alpha_T + \tan\beta_T) \tag{7B}$$

$$d = \{(Tm0^2 - L^2)/2(Tm0 - L\sin\alpha_T)\} \times \cos\alpha_T \tag{8B}$$

$$d = \{(Tm0^2 - L^2)/2(Tm0 - L\sin\beta_T)\} \times \cos\beta_T \tag{9B}$$

FIG. 43 shows a case wherein a single array probe is divided into transmission probe 10T and reception probe 10R, instead of using two separate probes. FIG. 44 shows a case wherein some of the transducers of probe 10T (FIG. 43) are also used as some of the transducers of probe 10R. In this case, by arbitrarily changing a combination of a set of transmission transducers and a set of reception transducers, aperture sizes aT and aR can be freely changed. The transmission and reception beam index points AT and AR change in accordance with changes in aperture sizes aT and aR. More particularly, even when the probe 10 is stationarily placed on tested body 14, distance L between probes 10T and 10R can be readily changed in accordance with a change in the combination of sets of transmission and reception transducers. Therefore, when distance L is set at various values to obtain a plurality of values for flaw dimension d and a mean value of flaw dimension d is obtained, actual flaw dimension d can be evaluated with high precision.

Figure 45:
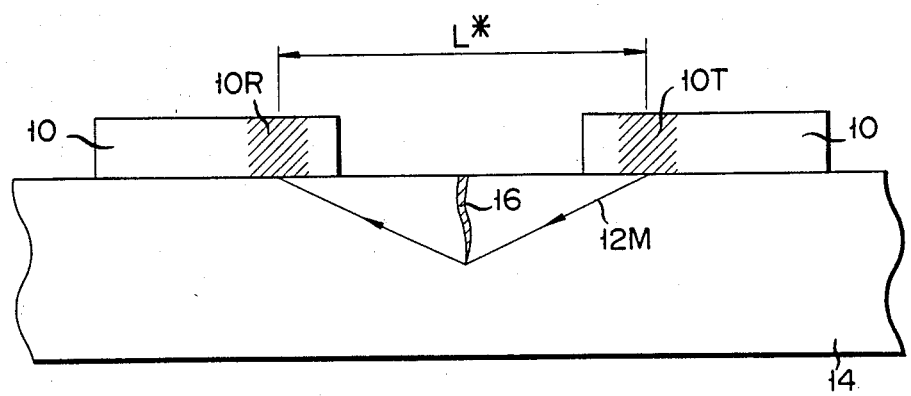
FIGS. 45 to 47 respectively show propagation of ultrasonic main beam 12M for various values of distance L* between the center of transmission portion (10T) and the center of reception portion (10R)
Figure 46:
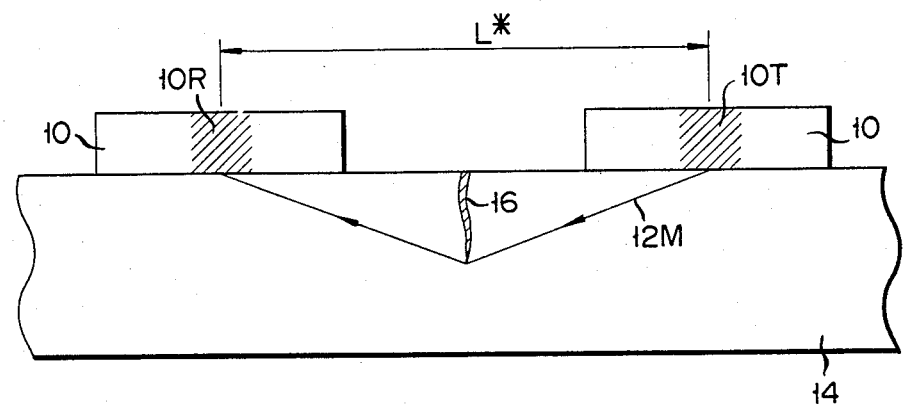
Figure 47:
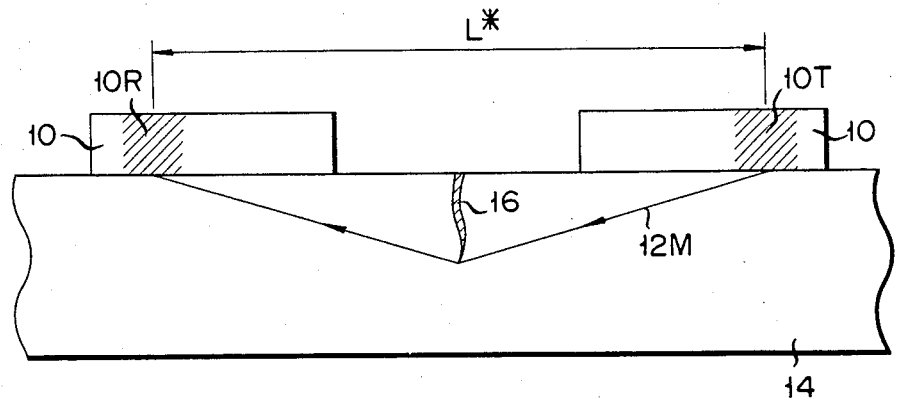
Figure 48:
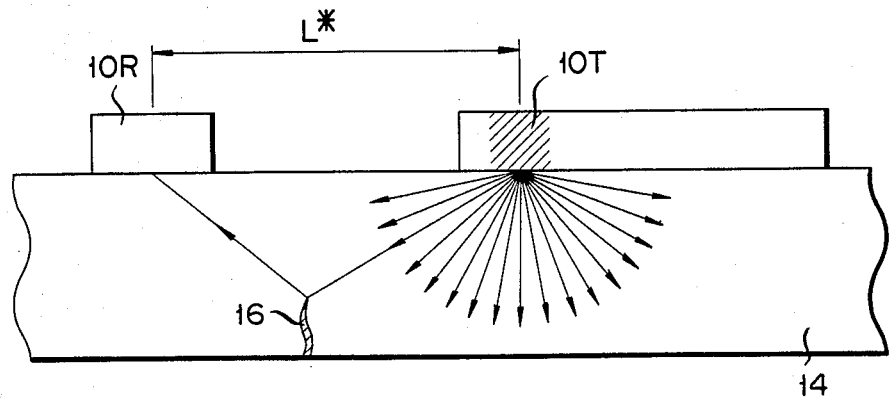
FIGS. 48 to 50 respectively show propagation of ultrasonic beams when transmission portion (10T) is set to be nondirectional for various values of distance L* between the center of nondirectional transducers (10T) and the center of reception transducers (10R).
Figure 49:
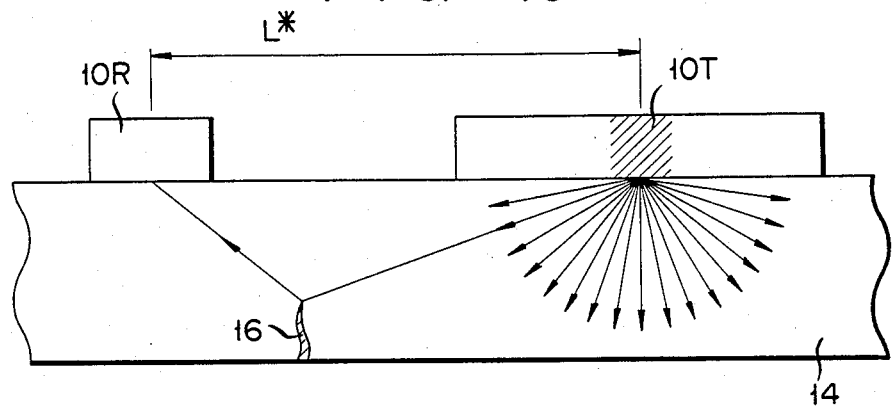
Figure 50:
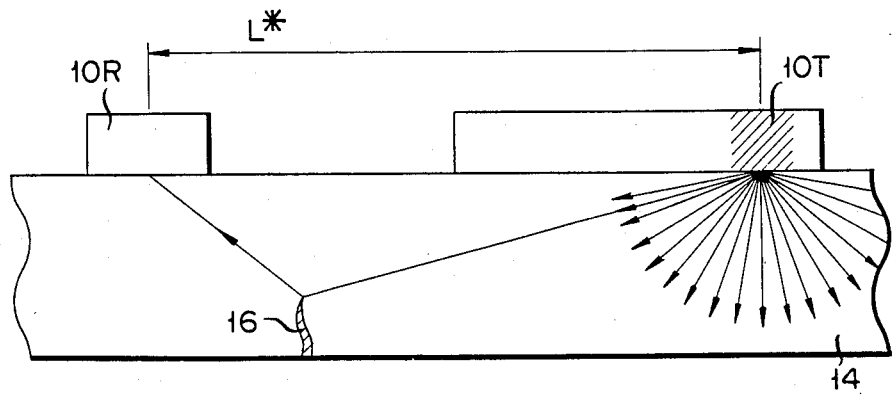

FIGS. 45 to 47 show cases wherein distance L* between the sets (10T and 10R) of selected transducers for transmission and reception takes various values. By this configuration, distance L* can be freely changed while probes 10T and 10R are stationarily placed on tested body 14. Values of flaw dimension d for all distances L* are obtained and their mean value is obtained, thereby evaluating flaw dimension d with high precision FIGS. 48 to 50 show cases wherein transmission transducers (10T) are preset to be nondirectional, and distance L* between the center of nondirectional transmission transducers (10T) and the center of reception transducers (10R) varies. When the transducers (10T) are preset to be nondirectional, transmission angle $\alpha i$ need not be varied. As a result, testing time and evaluation time of flaw dimension d can be decreased. Furthermore, in the same manner as in FIGS. 45 to 47, distance L* may be varied and a mean value for flaw dimension d for all distances L* may be obtained.

Since an electronic scanning ultrasonic testing apparatus is used in the present invention, convergence of ultrasonic beams at the time of transmission and reception can be electronically performed. Since the degree of convergence of beams at a desired position is increased to improve resolution, the position and dimension of the flaw can be evaluated with high precision.

Although the present invention is described with reference to the particular embodiments, various other changes and modifications may be made within the spirit and scope of the present invention.

What is claimed is:

1. A phased array ultrasonic testing apparatus comprising:
    (a) array probe means having a plurality of ultrasonic transducers for transmitting an ultrasonic wave into a body to be tested and for receiving an ultrasonic echo wave;
    (b) transmitting means coupled to said probe means, for driving said transducers to transmit an ultrasonic main beam in a predetermined direction within said body;
    (c) synthesizing means coupled to said probe means, for synthesizing reception echo signals corresponding to ultrasonic echoes received by said transducers and generating synthesized reception echo signals as a composite reception signal; and
    (d) signal processing means coupled to said synthesizing means, for generating an image signal synchronous with said composite reception signal in accordance with a beam index point of said ultrasonic main beam and a steered angle thereof.

2. A phased array ultrasonic testing apparatus comprising:
    (a) a plurality of array probe means at least one of which has a plurality of ultrasonic transducers for transmitting an ultrasonic wave into a body to be tested and for receiving an ultrasonic echo wave;
    (b) transmitting means coupled to one of said probe means, for driving said transducers to transmit an ultrasonic main beam in a predetermined direction within said body;
    (c) synthesizing means coupled to another of said probe means, for synthesizing reception echo signals corresponding to ultrasonic echoes received by said transducers and generating synthesized reception echo signals as a composite reception signal; and
    (d) signal processing means coupled to said synthesizing means, for generating an image signal synchronous with said composite reception signal in accordance with a beam index point of said ultrasonic main beam and a steered angle thereof.

3. An apparatus of claim 1, wherein said synthesizing means includes delaying means for delaying signals respectively corresponding to said reception echo signals at a predetermined order, and adding means for adding ordered signals produced by said delaying means to output said composite reception signal.

4. An apparatus of claim 1, wherein said beam index point and said steered angle of said ultrasonic main beam are determined in accordance with a predetermined ultrasonic main beam convergence path length, a predetermined ultrasonic beam steered angle, and an aperture size of said probe means, said steered angle of said ultrasonic main beam being defined with respect to a normal line at said beam index point and said predetermined ultrasonic beam steered angle being defined with respect to a normal line at a central point of an array of transducers of said probe means.

5. An apparatus of claim 4, wherein said steered angle $\phi$ of said ultrasonic main beam is determined by:

$$\phi = \{\tan^{-1}(\tan\theta + a/2l) + \tan^{-1}(\tan\theta - a/2l)\}/2$$

where a is said aperture size of said probe means, $\theta$ is said predetermined ultrasonic beam steered angle, and l is said predetermined ultrasonic main beam convergence path length.

6. An apparatus of claim 5, wherein a distance e, ovs-/AC/ between said beam index point and said central point of said array of transducers is determined by:

$$\overline{AC} = [\{\sqrt{1 + ((a/2l)\sin 2\phi)^2} - 1\}/\sin 2\phi] \times l$$

where a is said aperture size of said probe means, $\phi$ is said beam steered angle of said ultrasonic main beam, and l is said predetermined ultrasonic main beam convergence path length.

7. An apparatus of claim 6, wherein said distance $\overline{AC}$ can be calculated by an approximation $a^2 \sin 2\phi/8l$ when the term (a/2l) is smaller than 1.

8. An apparatus of claim 1, further comprising:
    (e) displaying means coupled to said signal processing means, for displaying internal information of said body in accordance with said image signal.

9. An apparatus of claim 8, wherein said displaying means has means for B-scope displaying a section of said body in accordance with said image signal.

10. An apparatus of claim 8, wherein said displaying means has means for recording the internal information of said body in accordance with said image signal.

11. An apparatus of claim 1, wherein said displaying means has means for A-scope displaying an inside of said body in accordance with said composite reception signal.

12. An apparatus of claim 1, wherein said signal processing means includes:
    gate means for providing as gated signals composite reception signal components within a predetermined limited range along a time base of said composite reception signal; and
    maximum value detecting means coupled to said gate means, for detecting as a maximum gated signal a maximum signal of said gated signals which fall within said predetermined limited range.

13. An apparatus of claim 12, wherein said signal processing means includes:
    determining means coupled to said maximum value detecting means, for detecting said maximum gated signals for various transmission angles and reception angles and detecting a maximal signal among said maximum gated signals, and for determining transmission and reception steered angles when said maximal signal is obtained, and
    means coupled to said determining means, for evaluating a flaw dimension of a flaw portion in said body in accordance with at least one of said determined transmission and reception steered angles.

14. An apparatus of claim 13, wherein said flaw dimension d is evaluated by $$d = t - L/(\tan\alpha_T + \tan\beta_T)$$

where t is a thickness of said body, L is a distance between transmission and reception beam index points of said ultrasonic main beam, $\alpha_T$ is an angle formed between the transmitted main beam and the normal line at said transmission beam index point of said main beam, and $\beta T$ is an angle formed between the received main beam and the normal line at said reception beam index point of said main beam.

15. An apparatus of claim 13, wherein said flaw dimension d is evaluated by:

$$d = \{1/(\tan \alpha_{T1} + \tan \beta_{T1}) - 1/(\tan \alpha_{T2} + \tan \beta_{T2})\}L$$

where L is a distance between transmission and reception beam index points of said ultrasonic main beam, $\alpha_{T1}$ is an angle formed between a first transmitted main beam and the normal line at a first transmission beam index point of said main beam, $\beta_{T1}$ is an angle formed between a first received main beam and the normal line at a first reception beam index point of said main beam, $\alpha_{T2}$ is an angle formed between a second transmitted main beam and the normal line at a second transmission beam index point of said main beam, and $\beta_{T2}$ is an angle formed between a second received main beam and the normal line at a second reception beam index point of said main beam.

16. An apparatus of claim 13, wherein said flaw dimension d is evaluated by:

$$d = L/(\tan \alpha_T + \tan \beta_T)$$

where L is a distance between transmission and reception beam index points of said ultrasonic main beam, $\alpha_T$ is an angle formed between the transmitted main beam and the normal line at said transmission beam index point of said main beam, and $\beta_T$ is an angle formed between the received main beam and the normal line at said reception beam index point of said main beam.

17. An apparatus of claim 1, wherein said signal processing means includes:
second gate means coupled to said gate means, for providing second gated signals respectively indicating beam propagation path lengths of said ultrasonic main beam; and
minimum value detecting means coupled to said second gate means, for detecting as a minimum beam propagation path length signal a minimum signal of said second gated signals.

18. An apparatus of claim 17, wherein said signal processing means includes:
determining means coupled to said minimum value detecting means, for detecting said minimum beam propagation path length signals for various transmission steered angles and reception steered angles and detecting a minimal signal among said minimum beam propagation path length signals, and for determining transmission and reception steered angles when said minimal signal is obtained, and
means coupled to said determining means, for evaluating a dimension of a flaw portion in said body in accordance with at least one of said determined transmission and reception steered angles.

19. An apparatus of claim 18, wherein said flaw dimension d is evaluated by:

$$d = t - L/(\tan \alpha_T + \tan \beta_T)$$

where t is a thickness of said body, L is a distance between transmission and reception beam index points of said ultrasonic main beam, $\alpha_T$ is an angle formed between the transmitted main beam and the normal line at said transmission beam index point of said main beam, and $\beta_T$ is an angle formed between the received main beam and the normal line at said reception beam index point of said main beam.

20. An apparatus of claim 18, wherein said flaw dimension d is evaluated by:

$$d = t - \{(Tm0^2 - L^2)/2(Tm0 - L \sin \alpha_T)\} \cos \alpha_T$$

where t is a thickness of said body, L is a distance between transmission and reception beam index points of said ultrasonic main beam, $\alpha_T$ is an angle formed between the transmitted main beam and the normal line at said transmission beam index point of said main beam, and Tm0 is a beam propagation path length corresponding to said minimal signal.

21. An apparatus of claim 18, wherein said flaw dimension d is evaluated by:

$$d = t - \{(Tm0^2 - L^2)/2(Tm0 - L \sin \beta_T)\} \cos \beta_T$$

where t is a thickness of said body, L is a distance between transmission and reception beam index points of said ultrasonic main beam, $\beta_T$ is an angle formed between the received main beam and the normal line at said reception beam index point of said main beam, and Tm0 is a beam propagation path length corresponding to said minimal signal.

22. An apparatus of claim 18, wherein said flaw dimension d is evaluated by:

$$d = \{1/(\tan \alpha_{T1} + \tan \beta_{T1}) - 1/(\tan \alpha_{T2} + \tan \beta_{T2})\}L$$

where L is a distance between transmission and reception beam index points of said ultrasonic main beam, $\alpha_{T1}$ is an angle formed between a first transmitted main beam and the normal line at a first transmission beam index point of said main beam, $\beta_{T1}$ is an angle formed between a first received main beam and the normal line at a first reception beam index point of said main beam, $\alpha_{T2}$ is an angle formed between a second transmitted main beam and the normal line at a second transmission beam index point of said main beam, and $\beta_{T2}$ is an angle formed between a second received main beam and the normal line at a second reception beam index point of said main beam.

23. An apparatus of claim 18, wherein said flaw dimension d is evaluated by:

$$d = L/(\tan \alpha_T + \tan \beta_T)$$

where L is a distance between transmission and reception beam index points of said ultrasonic main beam, $\alpha_T$ is an angle formed between the transmitted main beam and the normal line at said transmission beam index point of said main beam, and $\beta_T$ is an angle formed between the received main beam and the normal line at said reception beam index point of said main beam.

24. An apparatus of claim 18, wherein said flaw dimension d is evaluated by:

$$d = \{\cos \alpha_{T1}/2(Tm0 - L \sin \alpha_{T1}) - \cos \alpha_{T2}/2(Tm0 - L \sin \alpha_{T2})\} \times (Tm0^2 - L^2)$$

where L is a distance between transmission and reception beam index points of said ultrasonic main beam, $\alpha_{T1}$ is an angle formed between a first transmitted main beam and the normal line at a first transmission beam index point of said main beam, $\alpha_{T2}$ is an angle formed between a second transmitted main beam and the normal line at a second transmission beam index point of said main beam, and Tm0 is a beam propagation path length corresponding to said minimal signal.

25. An apparatus of claim 18, wherein said flaw dimension d is evaluated by:

$$d = \{(Tm^2 - L^2)/2(Tm0 - L \sin \alpha_T)\} \cos \alpha_T$$

where L is a distance between transmission and reception beam index points of said ultrasonic main beam, $\alpha_T$ is an angle formed between the transmitted main beam and the normal line at said transmission beam index point of said main beam, and Tm0 is a beam propagation path length corresponding to said minimal signal.

26. An apparatus of claim 18, wherein said flaw dimension d is evaluated by:

$$d = \{\cos \beta_{T1}/2(Tm0 - L \sin \beta_{T1}) - \cos \beta_{T2}/2(Tm0 - L \sin \beta_{T2})\} \times (Tm0^2 - L^2)$$

where L is a distance between transmission and reception beam index points of said ultrasonic main beam, $\beta_{T1}$ is an angle formed between a first received main beam and the normal line at a first reception beam index point of said main beam, $\beta_{T2}$ is an angle formed between a second received main beam and the normal line at a second reception beam index point of said main beam, and Tm0 is a beam propagation path length corresponding to said minimal signal.

27. An apparatus of claim 18, wherein said flaw dimension d is evaluated by:

$$d = \{(Tm0^2 - L^2)/2(Tm0 - L \sin \beta_T)\} \cos \beta_T$$

where L is a distance between transmission and reception beam index points of said ultrasonic main beam, $\beta_T$ is an angle formed between the received main beam and the normal line at said reception beam index point of said main beam, and Tm0 is a beam propagation path length corresponding to said minimal signal.

28. A method for phased array ultrasonic testing in which timings of ultrasonic transmission and reception are electronically controlled by an array probe having a plurality of ultrasonic transducers, comprising the steps of:
  (a) determining an actual steered angle of an ultrasonic main beam in accordance with a predetermined convergence path length of said ultrasonic main beam, a predetermined steered angle of said ultrasonic main beam, and an aperture size of said probe at the time of ultrasonic transmission, said predetermined steered angle being defined with respect to a normal line at a central point of an array of said transducers, and said actual steered angle being defined with respect to a normal line at an actual beam index point of said ultrasonic main beam;
  (b) determining a distance between said central point of said array and said actual beam index point in accordance with said actual steered angle, said predetermined convergence path length, and said aperture size; and
  (c) determining an image sweep start point and a sweep direction for displaying an ultrasonic echo received by said probe in accordance with said actual steered angle obtained in the step (a) and said distance obtained in the step (b).

29. A method for phased array ultrasonic testing in which timings of ultrasonic transmission and reception are electronically controlled by an array probe having a plurality of ultrasonic transducers, comprising the steps of:
  (a) determining an actual steered angle of an ultrasonic main beam in accordance with a predetermined convergence path length of said ultrasonic main beam, a predetermined steered angle of said ultrasonic main beam, and an aperture size of said probe at the time of ultrasonic transmission, said predetermined steered angle being defined with respect to a normal line at a central point of an array of said transucers, and said actual steered angle being defined with respect to a normal line at an actual beam index point of said ultrasonic main beam; and
  (b) B-scope displaying said ultrasonic echo received by said probe when a point is defined as an image sweep start point which is separated from said central point by a predetermined distance $\overline{DC}$ along the normal line at said central point of said array, said predetermined distance $\overline{DC}$ being given by $$\overline{DC} = a^2 \cos^2 \phi / 4l$$

where a is said aperture size, l is said predetermined convergence path length, and $\phi$ is said actual steered angle obtained in the step (a).

* * * * *